US007393842B2

(12) United States Patent
Makriyannis et al.

(10) Patent No.: US 7,393,842 B2
(45) Date of Patent: Jul. 1, 2008

(54) PYRAZOLE ANALOGS ACTING ON CANNABINOID RECEPTORS

(75) Inventors: Alexandros Makriyannis, Mystic, CT (US); Qian Liu, Malden, MA (US); Rajesh Thotapally, Willimantic, CT (US)

(73) Assignee: University of Connecticut, Farmington, CT (US)

( * ) Notice: Subject to any disclaimer, the term of this patent is extended or adjusted under 35 U.S.C. 154(b) by 304 days.

(21) Appl. No.: 10/790,498

(22) Filed: Mar. 1, 2004

(65) Prior Publication Data

US 2004/0192667 A1 Sep. 30, 2004

Related U.S. Application Data

(63) Continuation-in-part of application No. PCT/US02/27644, filed on Aug. 29, 2002.

(60) Provisional application No. 60/316,515, filed on Aug. 31, 2001.

(51) Int. Cl.
*A61K 31/55* (2006.01)
*A61K 31/454* (2006.01)
*A61K 31/416* (2006.01)
*A61K 31/4152* (2006.01)

(52) U.S. Cl. .............. 514/210.2; 514/217.08; 514/326; 514/406; 540/603; 546/211; 548/364.1

(58) Field of Classification Search .......... 514/210.2, 514/326; 540/603; 546/211; 548/364.1
See application file for complete search history.

(56) References Cited

U.S. PATENT DOCUMENTS

| | | | |
|---|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |

(Continued)

FOREIGN PATENT DOCUMENTS

| | | |
|---|---|---|
| EP | 0276732 | 8/1988 |
| EP | 0444451 | 9/1991 |
| EP | 0471609 | 6/1993 |
| EP | 0 576 357 | 12/1993 |

(Continued)

OTHER PUBLICATIONS

Meschler, J. P., Kraichely, D. M., Wilken, G. H., Howlett, A. C.; "Inverse Agonist Properties of N-(Piperidine-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoid Receptor"; Biochemical Pharmacology; (2000); vol. 60; No. 9; 1315-1322.

Jbilo, O., Derocq, J., Sequi, M., Le Fur, G., Casellas, P.; "Stimulation of peripheral cannabinoid receptor CB2 induces MCP-1 and IL-8 gene expression in human promyelocytic cell line HL60"; FEBS Letters; (1999); vol. 448; No. 21848; 273-277.

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

(Continued)

*Primary Examiner*—Kamal A Saeed
(74) *Attorney, Agent, or Firm*—Alix, Yale & Ristas, LLP

(57) ABSTRACT

One aspect of the invention is concerned with cannabimimetic pyrazole analogs. Another aspect of the invention is concerned with new and improved pyrazole analogs having high affinities and/or selectivities for the CB1 cannabinoid receptor. A further aspect of the invention is concerned with pharmaceutical preparations employing the inventive analogs and methods of administering therapeutically effective amounts of the inventive analogs to provide a physiological effect.

18 Claims, 1 Drawing Sheet

U.S. PATENT DOCUMENTS

| | | | |
|---|---|---|---|
| 5,462,960 A | 10/1995 | Barth et al. | |
| 5,489,580 A | 2/1996 | Makriyannis et al. | |
| 5,521,215 A | 5/1996 | Mechoulam | |
| 5,532,237 A | 7/1996 | Gallant et al. | |
| 5,538,993 A | 7/1996 | Mechoulam | |
| 5,576,436 A | 11/1996 | McCabe et al. | |
| 5,605,906 A | 2/1997 | Lau | |
| 5,607,933 A | 3/1997 | D'Ambra et al. | |
| 5,618,955 A | 4/1997 | Mechoulam et al. | |
| 5,624,941 A | 4/1997 | Barth et al. | |
| 5,631,297 A | 5/1997 | Pate et al. | |
| 5,635,530 A | 6/1997 | Mechoulam | |
| 5,688,825 A | 11/1997 | Makriyannis et al. | |
| 5,744,459 A | 4/1998 | Makriyannis et al. | |
| 5,747,524 A | 5/1998 | Cullinan et al. | |
| 5,804,601 A | 9/1998 | Kato et al. | |
| 5,817,651 A | 10/1998 | D'Ambra et al. | |
| 5,872,148 A | 2/1999 | Makriyannis et al. | |
| 5,874,459 A | 2/1999 | Makriyannis et al. | |
| 5,925,628 A | 7/1999 | Lee et al. | |
| 5,925,768 A | 7/1999 | Barth et al. | |
| 5,932,610 A | 8/1999 | Shohami et al. | |
| 5,939,429 A | 8/1999 | Kunos et al. | |
| 5,948,777 A | 9/1999 | Bender et al. | |
| 6,013,648 A | 1/2000 | Rinaldi et al. | |
| 6,028,084 A | 2/2000 | Barth et al. | |
| 6,096,740 A | 8/2000 | Mechoulam et al. | |
| 6,127,399 A | 10/2000 | Yuan | |
| 6,166,066 A | 12/2000 | Makriyannis et al. | |
| 6,284,788 B1 | 9/2001 | Mittendorf et al. | |
| 6,391,909 B1 | 5/2002 | Makriyannis et al. | |
| 6,579,900 B2 | 6/2003 | Makriyannis et al. | |
| 6,610,737 B1 | 8/2003 | Garzon et al. | |
| 7,119,108 B1 * | 10/2006 | Makriyannis et al. | 514/341 |
| 2002/0119972 A1 | 8/2002 | Leftheris et al. | |
| 2002/0173528 A1 | 11/2002 | Fride et al. | |
| 2003/0120094 A1 | 6/2003 | Makriyannis et al. | |
| 2003/0149082 A1 | 8/2003 | Makriyannis et al. | |
| 2004/0077649 A1 | 4/2004 | Makriyannis et al. | |
| 2004/0077851 A1 | 4/2004 | Makriyannis et al. | |
| 2004/0087590 A1 | 5/2004 | Makriyannis et al. | |
| 2004/0192667 A1 | 9/2004 | Makriyannis et al. | |
| 2004/0236101 A1 | 11/2004 | Makriyannis et al. | |
| 2004/0236116 A1 | 11/2004 | Makriyannis et al. | |

FOREIGN PATENT DOCUMENTS

| | | |
|---|---|---|
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| WO | WO 94/12466 | 6/1994 |
| WO | WO 97/00860 | 1/1997 |
| WO | WO 97/21682 | 6/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/058636 | 8/2002 |
| WO | WO 02/060447 | 8/2002 |
| WO | WO 03/005960 | 1/2003 |
| WO | WO 03/035005 | 5/2003 |
| WO | WO 03/063758 | 8/2003 |
| WO | WO 03/064359 | 8/2003 |

OTHER PUBLICATIONS

Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

Supplementary Partial European Search Report for application No. 02 76 8751, pp. 1-2.

U.S. Appl. No. 09/600,786, filed Nov. 24, 1999, Makriyannis et al.
U.S. Appl. No. 09/698,071, filed Oct. 30, 2000, Fride et al.
U.S. Appl. No. 09/701,989, filed Jun. 9, 1999, Makriyannis et al.
U.S. Appl. No. 10/110,865, filed Oct. 18, 2000, Makriyannis et al.
U.S. Appl. No. 10/110,830, filed Oct. 18, 2000, Makriyannis et al.
U.S. Appl. No. 10/110,812, filed Oct. 18, 2000, Makriyannis et al.
U.S. Appl. No. 10/110,862, filed Oct. 18, 2000, Makriyannis et al.
U.S. Appl. No. 10/111,059, filed Oct. 18, 2000, Makriyannis et al.
U.S. Appl. No. 10/647,544, filed Aug. 25, 2003, Makriyannis et al.
U.S. Appl. No. 10/899,191, filed Jul. 26, 2004, Makriyannis et al.

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; 1994; CODEN: JMCMAR; ISSN: 0022-2623; XP002040932.

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenated Dibenzo[b,d]pyran-6-ones Related to Ellagic Acid, J. Org. Chem. 1991, 56, 3763-3768.

Archer et al; "cannabinoids, synthesis approaches to 9-ketocannabinoids."; J. Org. Chem.; vol. 42, No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Barnett-Norris et al; "Exploration of biologically relevant conformations of anandamide, . . . "; J. Med. Chem.; vol. 41; 4861-4872; 1998.

Beak, P.; and Brown, R A., The Tertiary Amide as an Effective Director of Ortho Lithiation, J. Org. Chem. 1982, 47, 34-36.

Belgaonkar et al; "synthesius of isocoumarins"; Indian J. Chem; vol. 13; No. 4; 336-338; 1975 (abstract only).

Beltramo M., Stella N., Calignano A., Lin S. Y., Makriyannis A., Piomelli D; "Functional Role of High-Affinity Anandamide Transport, as Revealed by Selective Inhibition"; Science; vol. 277; 1094-1097; 1997.

Beltramo M., Stella N., Calignano A., Lin S. Y., Makriyannis A., Piomelli D; "Identification and Functional Role of High Affinity Anandamide Transport"; The Neurosciences Institute (1 page).

Beltramo M., Piomelli D; "Anandamide Transport Inhibition by the Vanilloide Agonist Olvanil"; Europeean J. of Pharmacology; (1999); 364(1); 75-78 (abstract only).

Berdyshev EV, Cannabinoid receptors and the regulation of immune response. Chem Phys Lipids. Nov. 2000; 108(1-2):169-90.

Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998).

Bodner, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Bracey, M et al, Structural Adaptions in a Membrane Enzyme That Terminates Encocannabinoid Signaling. Science 2002; 298(5599): 1793-1796.

Brenneisen R, Pgli A, Elsohly MA, Henn V. Spiess Y: The effect of orally and rectally administered Δ9—tetrahydrocannabinol on spasticity, a pilot study with 2 patients. Int. Clin Pharmacol Ther. (1996) 34:446-452. (abstract only).

Brotchie JM: Adjuncts to dopamine replacement a pragmatic approach to reducing the problem of dyskinesia in Parkinson's disease. Mov. Disord. (1998)13:871-876. (abstract only).

Brown et al; "Synthesis and hydroboration of (-)-2-phenylapopinene, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).

Buckley NE, McCoy KI, Mpzey E et al, "Immunomodulation by cannabinoids is absent in mice deficient for the cannabionoid CB2 receptor"; Eur. J Pharmacol (2000) 396:141-149.

Burstein et al; "detection of cannabinoid receptors . . . "; Biochem. Biophys. Res. Commun.; vol 176(1); 492-497; 1991 (abstract only).

Busch-Peterson et al; "Unsaturated side chain beta-11-hydroxyhexahydrocannabinol analogs"; J. Med. Chem.; 39; 3790-3796; (1996).

Calignano A, La Rana G. Diuffrida A, Piomelli D; "Control of pain initiation by endogenous cannabinoids"; Nature (1998) 394:277-291. (abstract only).

Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.

Campbell FA et al; "Are cannabinoids an effective and safe treatment option in the management of pain? A qualitative systematic review"; BMJ. 2001 Jul. 7;323(7303):13-6.

Charalambous A. et al; "5'-azido Δ8-THC: A Novel Photoaffinity Label for the Cannabinoid Receptor"; J. Med. Chem., 35, 3076-3079 (1992).

Charalambous A. et al; "Pharmacological evaluation of halogenated . . . "; Pharmacol. Biochem. Behav.; vol. 40, No. 3; 509-512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).

Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.

Cherest M., Lusinchi X.; "A novel electrophilic N-amidation via electron deficient complexes: action of ferric chloride on N-acetyloxyamides"; Tetrahedron Letters; 30(6); 715-718; 1989.

Colombo G, Agabio R, Diaz G. et al; "Appetite suppression and weight loss after the cannabinoid antagonist SR141716"; Life Sci. (1998) 63-PL13-PL117. (abstract only).

Compton D.R. et al; "Pharmacological Profile Of A Series Of Bicyclic Cannabinoid Analogs: Classification as Cannabimimetic Agents"; J. Pharmacol. Exp. Ther.; 260; 201-209; 1992. (abstract only).

Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.

Consroe P, Musty R, Rein J, Tillery W, Pertwee R; "The perceived effects of smoked cannabis on patents with multiple sclerosis"; Eur. Neurol. (1997) 38-44-48. (abstract only).

Coxon et al; "Derivatives of nopinone"; Aust. J. Chem.; 23; 1069-1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.

D'Ambra et al; "C-attached aminoalkylindoles: potent cannabinoid mimetics"; Bioorg. & Med. Chem. Lett., 1996, 6(1), 17-22.

D'Amour F.E. et al; "A Method For Determining Loss of Pain Sensation"; J. Pharmacol. Exp. Ther.; 72; 74-79;1941.

Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.

DePetrocellis L, Melck D, Palmisano A. et al; "The endogenous cannabinoid anandamide inhibits human breast cancer cell proliferation"; Proc. Natl. Acad. Sci USA (Jul. 1998) 95:8375-8380.

Desarnaud F., Cadas H., Piomelli D.; "Anandamide amidohydrolase activity in rat brain microsomes"; J. Biol. Chem.; 270; 6030-6035; (1995).

Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.

Deutsch D.G., Chin S.A.; "Enzymatic synthesis and degration of anandamide, a cannabinoid receptor agonist "; Biochemical Pharmacology; 46(5); 791-796; 1993.

Devane, W.A. et al; "Determination and Characterization of a Cannabinoid Receptor in a Rat Brain"; Mol. Pharmacol., 34, 605-613 (1988). (abstract only).

Di Marzo, V., Melck D., Bisogno, T., Depetrocellis, L.; "Endocannabinoids: endogenous cannabinoid receptor ligands with neuromodulatory action"; Trends Neurisci. (1998) 21:521-528.

Di Marzo, V., Bisogno, T., Melck, D., Ross, R., Brockie, H., Stevenson, L., Pertwee, R., Depetrocellis, L., "Interactions between synthetic vanilloids and the endogenous cannabinoid system"; FEBS Letters; (1998); 437(3): 449-454. (abstract only).

Dodd, P.R. et al, A Rapid Method for Preparing Synaptosomes: Comparison with Alternative Procedures, Brain Res., 226, 107-118 (1981). (abstract only).

Dominiami et al; "Synthesis of 5-(tert-Alkyl)resorcinols"; J. Org. Chem. 42(2); 344-346; (1977).

Drake et al, "classical/nonclassical hybrid cannabinoids"; J. Med. Chem.; vol. 41(19); 3596-3608 (1998).

Edery et al; "Activity of novel aminocannabinoids in baboons"; J. Med. Chem.; 27; 1370-1373 (1984).

Eissenstat et al; "Aminoalkylindoles: structure-activity relationships of novel cannabinoid mimetics"; J. Med. Chem. 1995, vol. 38, No. 16, pp. 3094-3105; XP 000651090.

Fahrenholtz, K. E., Lurie, M. and Kierstead, AR. W.; "The Total Synthesis of dl-t42 9-Tetrahydrocannabinol and Four of Its Isomers"; J. Amer. Chem. Soc. 1967, 89(23), 5934-5941.

Fahrenholtz; "The synthesis of 2 metabolites of (-)-delta eight-tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).

Fride, E. & Mechoulam, R.; "Pharmacological activity of the cannabinoid receptor agonist, anandamide, a brain constituent"; European Journal of Pharmacology, vol. 231; 313-314; 1993.

Galiegue S et al. ; "Expression of central and peripheral cannabinoid receptors in human immune tissues and leukocyte subpopulations"; Eur J Biochem.; Aug. 15, 1995;232(1):54-61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analoogs on human cannabinoid receptors"; Bioorg. Med. Chem. Lett. 1996, 6(2), 189-194.

Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.

Green K.; "Marijuana smoking vs. cannabinoids for glaucoma therapy."; Arch. Ophthamol. (Nov. 1998) 116(11); 1433-1437. (abstract only).

Hampson, A.J., Grimaldi M. Axpirod J. Wink D; "Cannabidiol and (-) Δ9 tetrahydrocannabinol are neuroprotective antioxidants"; Proc. Natl Acad Sci. USA (Jul. 1998) 95; 8268-8273.

Hanus et al; "Two new unsaturated fatty acid ethanolamides in brain that bind to the cannabinoid receptor"; Journal of medicinal Chemistry; 36(20); 3032-3034; 1993.

Hargreaves, K. et al; "A new sensitive method for measuring thermal nociception in cutaneous hyperalgesia"; Pain; 32; 77-88; (1988) (abstract only).

Hemming M, Yellowlees PM; "Effective treatment of Tourette's syndrome with marijuana"; J. Psychopharmacol, (1993) 7:389-391.

Herzberg U, Eliav E, Bennett GJ, Kopin IJ; "The analgesic effects of R (+) WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B; "Accumulation of N-Arachidonoylethanolamine (Anandamide) into Cerebellar Granule Cells Occurs via Facilitated Diffusion"; Journal of Neurochemistry; 69; 631-638 (1997).

Horrevoets A.J.G et al; "Inactivation of *Escherichia coli* outer membrane phospholipase A by the affinity label hexadecanesulfonyl fluoride"; Eur. J. Biochem.; 198; 247-253; 1991.

Horrevoets A.J.G et al; "Inactivation of reconstituted *Escherichia coli* outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology, vol. 29(2); 161-165; 1990.

Huffman et al; "3-(1', 1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

Huffman et al; "Synthesis of 5',11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Joy JE, Wagston SJ, Benson JA; "Marijuana and Medicine Assessing the Science Base"; National Academy Press, Washington, DC, USA (1999). (abstract only).

Kaminski NE; "Regulation of the cAMP cascade, gene expression and immune function by cannabinoid receptors"; J. Neuroimmunol. Mar. 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug 1998; 19(8):373-81.

Koutek B. et al; "Inhibitors of arachidonyl ethanolamide hydrolysis"; J. Biol. Chem.; 269(37); 22937-40: 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

Lang, W. et al; "Substrate Specificity and Stereoselectivity of Rat Brain Microsomal Anandamide Amidohydrolase"; J. Med. Chem.; vol. 42(5); 896-902; (1999).

Lavalle et al; "Efficient conversion of (1R, 5R)-(+)-alpha-pinene to (1S, 5R)-(-)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyllithium and lithium diisopropylamide in the metalations of N,N-dialkyltouamides"; J. Org. Chem.; 38(9); 1668-1674 (1973).

Maccarron M., Endocannabinoids and their actions. *Vitamins and Hormones* 2002;65:225-255.

Mackie K., Devane W.A., Hille B.; "Anandamide, an endogenous cannabinoid, inhibits calcium currents as a partial agonist in N18 neuroblastoma cells"; Mol. Pharmacol; 44: 498-0503 (1993).

Markwell, M.A.K., S.M. Haas, L.L. Bieber, and N.E. Tolbert.; "A modification of the Lowry procedure to simplify protein determination in the membrane and lipoprotein samples." 1978; *Anal. Biochem.* 87:206-210.

Martin et al; "Behavioral, biochemical, and molecular modeling evaluations of cannabinoid analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068-1072; (1980).

Mechoulam et al; Structural Requirements for Binding of Anandamide Type Compounds to the Brain Cannabinoid Receptor; J. Med. Chem.; 1997; 40; 659-667.

Mechoulam et al; "Synthesis of the individual, pharmacologically distinct, enantiomers of a tetrahydrocannabinol derivative"; Tetrahedron Asymmetry; 1: 311-314; (1990) (abstract only).

Mechoulam et al; "Synthesis of the individual, pharmacologically distinct, enantiomers of a tetrahydrocannabinol derivative."; *Tetrahedron Asymmetry*; 1: 315-318; (1990).

Mechoulam, "Cannabinoids as therapeutic agents"; *CRC press*, 1986.

Mechoulam et al; "Towards Cannabinoid drugs—Revisited"; Progress in Medicinal Chemistry; 35; 199-243; Jul. 3, 1998.

Melck, D., Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284 (abstract only).

Meltzer et al; "An improved synthesis of cannabinol and cannabiorcol"; Synthesis; 1981:985 (1981).

Melvin et al; "Structure-Activity Relationships Defining The ACD-Tricyclic Cannabinoids Cannabinoid Receptor Binding and Analgesic Activity"; Drug Design and Discovery; 13(2); 155-166 (1995). (abstract only).

Melvin et al; "Structure-activity relationships for cannabinoid receptor-binding and analgesic activity: studies of bicyclic cannabinoid analogs"; Mol. Pharmacol.; 44(5); 1008-1015 (1993). (abstract only).

Merck Index; 11th edition; "Tetrahydrocannabinols" compound No. 9142; 1989.

Morgan Dr: Therapeutic Uses of Cannabis. *Harwood Academic Publishers*, Amsterdam. (1997).

Morris, S,; Mechoulam, R.; and Irene, Y., Halogenation of phenols and Phenyl ethers with Potassium Halides in the Presence of 18-Crown-6 on Oxidation with m-Chloroperbenzoic Acid, *J. Chem. Soc.*, Perkin Trans. 1 1987, 1423-1427.

Muller-Vahl KB, Kolbe H, Schneider U, Emrich, HM Cannabis in movement disorders. Porsch. Kompicmentarmed (1999) 6 (suppl. 3) 23-27. (abstract only).

Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Nahas G, Marijuana and Medicine; 1999, *Human Press Inc.*, Totowa, NJ.

Neunhoeffer O., Gottschlich R.; "Acylating activity of O-acylated hydroxylamine derivatives"; Justus Liebigs Ann. Chem.; 736; 100-109; 1970; in German with English abstract.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labeled with [H]-5'-trimethylammonium delta8-tetrahydrocannabinol"; J. Pharmacol. Exp. Ther.; vol. 234(3); 784-791; 1985.

Pacheco M, et al; "Aminoalkylindoles: Actions On Specific G- Protein-LInked Receptors"; J. Pharmacol. Exp. Ther.; vol. 257, No. 1, pp. 170-183 and 172 Table (1991).

Palmer et al; "Natural and Synthetic Endocannabinoids and Their Structure-Activity Relationships"; Current Pharmaceutical Design; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoid receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

Pertwee; Pharmacology of cannabinoid CB1 and CB2 receptors; Pharmacol. Ther., vol. 74(2); pp. 129-180; (1997); XP002226467.

Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Pinnegan-Ling D, Musty R.; Marinol and phantom limb pain: a case study. *Proc Inv. Cannabinoid Rea. Sec.* (1994):53.

Pinto et al; Cannabinoid Receptor Binding and Agonist Activity of Amides and Esters of Arachidonic Acid; Mol. Pharmacol.; 1994; 46(3); 516-522.

Piomelli D., Beltramo M., Glasnapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labelled cannabinoids"; Journal of Labellled Compounds; vol. 11(4); 551-575; 1975; XP002123229.

Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Razdan et al; "Drugs derived from cannabinoids. 6. .Synthesis of cyclic analogues of dimethylheptylpyran"; J. Med. Chem.; vol. 19(5); 719-721; 1976 (abstract only).

Razdan et al; "Pharmacological and Behavioral Evaluation of Alkylated Anandamide Analogs"; Life Sci.; 1995; 56(23-24); 2041-2048.

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228-3233.

Rice AS. Cannabinoids and pain. Curr Opin Investig Drugs. Mar. 2001;2(3):399-414. (abstract only).

Richardson JD, Aanonsen I, Hargreaves KM; "Antihyperalgesic effects of a spinal cannabinoids"; Eur. J. Pharmacol. (1998) 346:145-153.

Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

Schuel, H., Burkman, L.J., Picone, R.P., Bo, T., Makriyannis, A., Cannabinoid receptors in human sperm. *Mol. Biol. Cell.*, (1997) (8), 325a.

Serdarevich B., Caroll K.K., "Synthesis and characterization of 1- and 2-monoglycerides of anteiso fatty acids"; J. Lipid Res.; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal Of Chemistry; 64(5); 871-875; 1986 (abstract only).

Shen M. Thayer SA: Cannabinoid receptor agonists protect cultured rat hippocampal neurons from excitotoxicity. Mol. Pharmacol (1996) 54:459-462.

Shim et al; "Three-dimensional quantitative structure-activity relationship study of the cannabimimetic (aminoalkyl)indoles using comparative molecular field analysis"; J. Med. Chem.; 1998; 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Simiand J, Keane M, Keane PE, Soubrie P: SR 141716, A CB1 cannabinoid receptor antagonist, selectively reduces sweet food intake in marmoset. Behav. Pharmacol (1998) 9:179-181. (abstract only).

Smith P.B. et al; "The pharmacological activity of anandamide, a putative endogenous cannabinoid, in mice"; Journal of Pharmacology and Experimental Therapeutics; vol. 270(1):219-227; 1994.

Terranova J-P , Storme J-J Lafon N et al; "Improvement of memory in rodents by the selective CB1 cannabinoid receptor antagonist, SR 141716"; Psycho-pharmacol (1996) 126:165-172 (abstract only).

Tetko, I. V. et al; "Volume Learning Algoritm Artificial Neural Networks For 3D QSAR Studies"; J. Med. Chem.; vol. 44, No. 15 (2001) pp. 2411-2420, 2413, 2414 Table 1.

Tius et al; "Conformationally restricted hybrids of CP-55,940 and HHC: Steroeselective synthesis and activity"; Tetrahedron; 50 (9); 2671-2680; (1994) (abstract only).

Twitchell, W. et al; "Cannabinoids inhibit N- and P/Q type calcium channels in cultured rat hippocampal neurons"; Journal of Neurophysiology; 78(1); 43-50; 1997 (abstract only).

Ueda, N., Endocannabinoid hydrolases. Prostaglandins & Other Lipid Mediators 2002;68-69:521-534 (abstract only).

Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

Wagner JA, Varga K, Jarai Z, Kunos G; "Mesenteric Vasodilation Mediated by Endothelia Anandamide Receptors"; Hypertension (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-104; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potential electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(-)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

\* cited by examiner

PYRAZOLE ANALOGS ACTING ON CANNABINOID RECEPTORS

CROSS REFERENCE TO RELATED APPLICATION

This application is a continuation-in-part of International Application No. PCT/US02/27644, filed Aug. 29, 2002, which claims the benefit of U.S. Provisional Application No. 60/316,515, filed Aug. 31, 2001, the contents of each of which are herein incorporated by reference in their entirety.

FIELD OF THE INVENTION

The present invention relates generally to biologically active pyrazole analogs capable of interacting with the CB1 and/or the CB2 cannabinoid receptors. One aspect of the invention is concerned with new and improved pyrazole analogs acting as antagonists for the CB1 and/or the CB2 receptors. Another aspect of the invention is concerned with new and improved pyrazole analogs having selectivity for the CB1 or CB2 cannabinoid receptor. Still other aspects of the invention are concerned with pharmaceutical preparations employing the inventive analogs and methods of administering therapeutically effective amounts of the inventive analogs to provide a physiological effect.

BACKGROUND OF THE INVENTION

The classical cannabinoid $\Delta^9$-Tetrahydrocannabinol ($\Delta^9$-THC) is the major active constituent extracted from *Cannabis sativa*. The effects of such cannabinoids are due to an interaction with specific high-affinity receptors. Presently, two cannabinoid receptors have been characterized: CB1, a central receptor found in the mammalian brain and a number of other sites in peripheral tissues; and CB2, a peripheral receptor found principally in cells related to the immune system. The CB1 receptor is believed to mediate the psychoactive properties associated with classical cannabinoids. Characterization of these receptors has been made possible by the development of specific synthetic ligands such as the agonists WIN 55212-2 and CP 55,940.

In addition to acting at the cannabinoid receptors, cannabinoids such as $\Delta^9$-THC also affect cellular membranes, thereby producing undesirable side effects such as drowsiness, impairment of monoamine oxidase function and impairment of non-receptor mediated brain function. The addictive and psychotropic properties of some cannabinoids also limit their therapeutic value.

U.S. Pat. No. 6,028,084 describes some pyrazole derivatives alleged to have binding affinity for the central cannabinoid receptor. International Publication Number WO 01/29007A1 also describes some pyrazole derivatives having binding affinity for cannabinoid receptors.

The pharmacological effects of cannabinoids pertain to a variety of areas such as the central nervous system, the cardiovascular system, the immune system and/or endocrine system. Compounds possessing an affinity for the CB1 and/or the CB2 cannabinoid receptors are useful as agents acting on the central nervous system and in a variety of other roles.

SUMMARY OF THE INVENTION

Briefly stated, one aspect of the invention is concerned with new and improved cannabimimetic (cannabinoid like) pyrazole analogs. The inventive cannabimimetic pyrazole ligands of this aspect can be represented by general formula I:

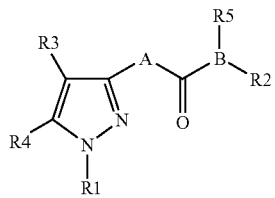

A comprises a direct bond, O or —$(CH_2)_l N(R6)$- ,
R6 comprises hydrogen or a C1 to C6 alkyl, and
l is an integer from 0 to about 1.
B comprises N or O.
R1 comprises —$(CH_2)_n$-Z.
n is an integer from 0 to about 7.
Z comprises H, halogen, $N_3$, NCS, CN, $NO_2$, $NX_1X_2$, $OX_3$, OAc, O-acyl, O-aroyl, $O(CH_2)_d OH$, $O(CH_2)_d NX_1X_2$, NH-acyl, NH-aroyl, CHO, $CF_3$, $COOX_3$, $SO_3H$, $SO_2NX_1X_2$, $CONX_1X_2$, alkoxy, alkylmercapto, alkylamino or di-alkylamino.
$X_1$ and $X_2$ each independently comprise H or alkyl, or
$X_1$ and $X_2$ together comprise part of a heterocyclic ring having about 4 to about 7 ring members and optionally one additional heteroatom selected from O, N or S, or
$X_1$ and $X_2$ together comprise part of an imide ring having about 5 to about 6 members.
$X_3$ comprises H, alkyl, hydroxyloweralkyl or alkyl-$NX_1X_2$.
d is an integer from 0 to about 6.
In a variation of the invention, R1 comprises —$(CH_2)_n$-Z.
n is an integer from 0 to about 7.
Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.
In a variation of the invention, R1 comprises —$(CH_2)_n$-Z.
n is an integer from 0 to about 7.
Z comprises a 5 member unsaturated ring having 0 to 4 independently selected heteroatoms as ring members, a substituted 5 member unsaturated ring having 0 to 4 independently selected heteroatoms as ring members, a 6 member aromatic ring having 0 to 5 independently selected heteroatoms as ring members or a substituted 6 member aromatic ring having 0 to 5 independently selected heteroatoms; and wherein the connecting point between the —$(CH_2)_n$— group and the Z group can be any available ring carbon atom or any available ring nitrogen atom.
In a variation of the invention, R1 comprises —$(CH_2)_n$-Z.
n is an integer from 0 to about 7.
Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of the invention, R1 comprises —(CH$_2$)$_n$-Z. n is an integer from 0 to about 7.

Z comprises

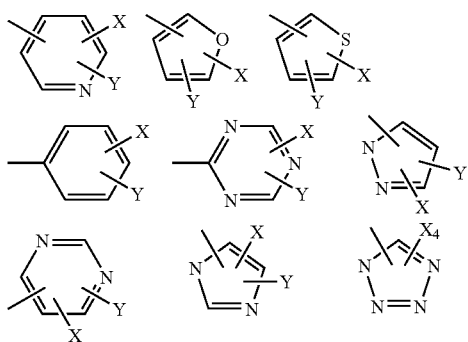

wherein X and Y each independently comprise H, halogen, N$_3$, NCS, CN, NO$_2$, NX$_1$X$_2$, OX$_3$, OAc, O-acyl, O-aroyl, NH-acyl, NH-aroyl, CHO, CF$_3$, COOX$_3$, SO$_3$H, SO$_2$NX$_1$X$_2$, CONX$_1$X$_2$, alkoxy, alkylmercapto, alkylamino, di-alkylamino, alkylsulfinyl, alkylsulfonyl or (when Z comprises a structure having two adjacent carbon atoms methylene dioxy.

X$_1$ and X$_2$ each independently comprise H or alkyl, or

X$_1$ and X$_2$ together comprise part of a heterocyclic ring having about 4 to about 7 ring members and optionally one additional heteroatom selected from O, N or S, or X$_1$ and X$_2$ together comprise part of an imide ring having about 5 to about 6 members.

X$_3$ comprises H, alkyl, hydroxyloweralkyl or alkyl-NX$_1$X$_2$.

X$_4$ comprises H or alkyl.

In a variation of the invention, R1 comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

In any of the above R1 variations R1 can not be H when A is a direct bond and B is N.

R2 comprises a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring or a heteropolycyclic ring.

In a variation of the invention, R2 comprises

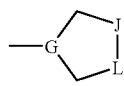

wherein G comprises CH or N, and L and J each independently comprise (CH$_2$)$_n$, O, NH or S, n is an integer from 0 to about 7.

In a variation of the invention, R2 comprises

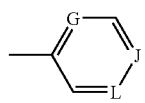

wherein G, L and J each independently comprise CH or N.

In a variation of the invention, R2 comprises

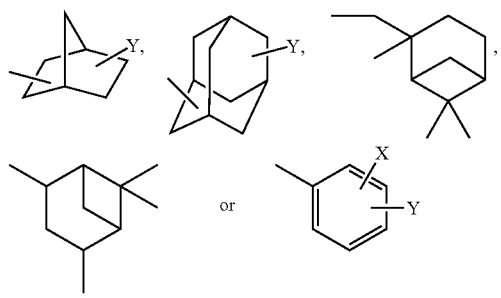

wherein X and Y each independently comprise H, halogen, N$_3$, NCS, Ph (phenyl), CN, NO$_2$, NX$_1$X$_2$, OX$_3$, OAc, O-acyl, O-aroyl, NH-acyl, NH-aroyl, CHO, CF$_3$, COOX$_3$, SO$_3$H, SO$_2$NX$_1$X$_2$, CONX$_1$X$_2$, alkyl, alcohol, alkoxy, alkylmercapto, alkylamino, di-alkylamino, alkylsulfinyl or alkylsulfonyl.

X$_1$ and X$_2$ each independently comprise H or alkyl, or

X$_1$ and X$_2$ together comprise part of a heterocyclic ring having about 4 to about 7 ring members and optionally a second heteroatom selected from O, N or S, or X$_1$ and X$_2$ together comprise part of an imide ring having about 5 to about 6 members.

X$_3$ comprises H, alkyl, hydroxyloweralkyl or alkyl-NX$_1$X$_2$.

In a variation of the invention, R2 comprises a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

R3 comprises H, halogen, $N_3$, NCS, Ph, CN, $NO_2$, $NX_1X_2$, $OX_3$, OAc, O-acyl, O-aroyl, $O(CH_2)_dOH$, $O(CH_2)_dNX_1X_2$, NH-acyl, NH-aroyl, CHO, $CF_3$, $COOX_3$, $SO_3H$, $SO_2NX_1X_2$, $CONX_1X_2$, alkyl, alcohol, alkoxy, alkylmercapto, alkylamino or di-alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$.

d is an integer from 0 to about 6.

In a variation of the invention, R3 comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring, a heterotricyclic ring, a polycyclic ring or a heteropolycyclic ring.

In an advantageous variation of the invention, R3 comprises

In a variation of the invention, R3 comprises —$CH_2$-Z.

Z comprises H, halogen, $N_3$, NCS, Ph, CN, $NO_2$, $NX_1X_2$, $OX_3$, OAc, O-acyl, O-aroyl, $O(CH_2)_dOH$, $O(CH_2)_dNX_1X_2$, NH-acyl, NH-aroyl, CHO, $CF_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$.

d is an integer from 0 to about 6.

In a variation of the invention, R3 comprises —$CH_2OH$ or —$CH_2Oalkyl$.

In a variation of the invention, R3 comprises —$CH_2$-Z.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a tricyclic ring or a heterotricyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of the invention, R3 comprises —$CH_2$-Z.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of the invention R3 comprises —$CH_2$-Q-$(CH_2)_n$-Z.

Q comprises N, O, S, $CH_3$, $SO_2$ or $OSO_2$.

n is an integer from 0 to about 7.

Z comprises H, halogen, $N_3$, NCS, Ph, CN, $NO_2$, $NX_1X_2$, $OX_3$, OAc, O-acyl, O-aroyl, NH-acyl, NH-aroyl, $O(CH_2)_dOH$, $O(CH_2)_dNX_1X_2$, CHO, $CF_3$, $COOX_3$, $SO_3H$, $SO_2NX_1X_2$, $CONX_1X_2$, alkyl, alcohol, alkoxy, alkylmercapto, alkylamino, di-alkylamino, alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

d is an integer from 0 to about 6.

In a variation of the invention R3 comprises —$CH_2$-Q-$(CH_2)_n$-Z.

Q comprises N, O, S, $CH_3$, $SO_2$ or $OSO_2$.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of the invention R3 comprises —CH$_2$-Q-(CH$_2$)$_n$-Z.

Q comprises N, O, S, CH$_3$, SO$_2$ or OSO$_2$.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of the invention, R3 comprises —CH$_2$-Q-(CH$_2$)$_n$-Z.

Q comprises N, O, S, CH$_3$, SO$_2$ or OSO$_2$.

n is an integer from 0 to about 7.

Z comprises

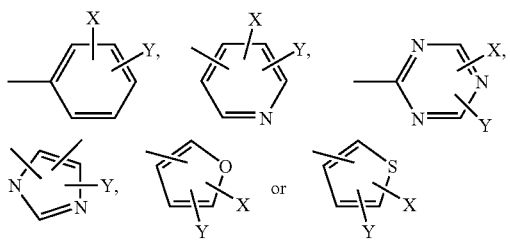

wherein X and Y each independently comprise H, halogen, N$_3$, NCS, CN, NO$_2$, NX$_1$X$_2$, OX$_3$, OAc, O-acyl, O-aroyl, NH-acyl, NH-aroyl, CHO, CF$_3$, alcohol, COOX$_3$, SO$_3$H, SO$_2$NX$_1$X$_2$, CONX$_1$X$_2$, alkoxy, alkylmercapto, alkylamino, di-alkylamino, alkylsulfinyl, alkylsulfonyl or (when Z comprises a structure having two adjacent carbon atoms) methylene dioxy.

X$_1$ and X$_2$ each independently comprise H or alkyl, or

X$_1$ and X$_2$ together comprise part of a heterocyclic ring having about 4 to about 7 ring members and optionally a second heteroatom selected from O, N or S, or X$_1$ and X$_2$ together comprise part of an imide ring having about 5 to about 6 members.

X$_3$ comprises H, alkyl, hydroxyloweralkyl or alkyl-NX$_1$X$_2$.

In any variation of R3 when A is not a direct bond and B is N then R3 cannot be H or a C1-C3 alkyl.

R4 comprises —(CH$_2$)$_n$-Z.

n comprises an integer from 0 to about 7.

Z comprises H, halogen, N$_3$, NCS, CN, NO$_2$, NX$_1$X$_2$, OX$_3$, OAc, O-acyl, O-aroyl, NH-acyl, NH-aroyl, O(CH$_2$)$_d$OH, O(CH$_2$)$_d$NX$_1$X$_2$, CHO, CF$_3$, COOX$_3$, SO$_3$H, SO$_2$NX$_1$X$_2$, CONX$_1$X$_2$, alkoxy, alkylmercapto, alkylamino, di-alkylamino alkylsulfinyl or alkylsulfonyl.

X$_1$ and X$_2$ each independently comprise H or alkyl, or

X$_1$ and X$_2$ together comprise part of a heterocyclic ring having about 4 to about 7 ring members and optionally a second heteroatom selected from O, N or S, or X$_1$ and X$_2$ together comprise part of an imide ring having about 5 to about 6 members.

X$_3$ comprises H, alkyl, hydroxyloweralkyl or alkyl-NX$_1$X$_2$.

d is an integer from 0 to about 6.

In a variation of the invention, R4 comprises —(CH$_2$)$_n$-Z.

n comprises an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In a variation of the invention, R4 comprises —(CH$_2$)$_n$-Z.

n comprises an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —(CH$_2$)$_n$— group and the Z group can be any available ring carbon atom or any available ring nitrogen atom.

In an advantageous variation of the invention, R4 comprises —(CH$_2$)$_n$-Z.

n comprises an integer from 0 to about 7.

Z comprises

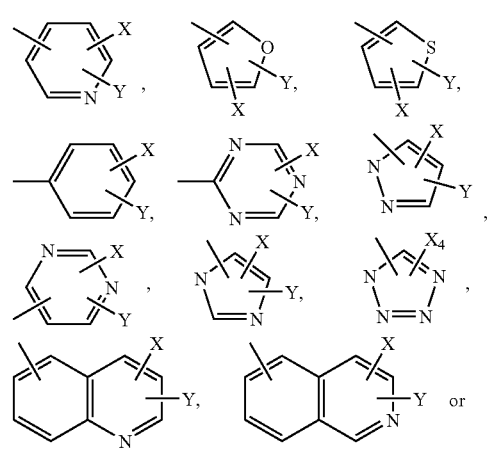

-continued

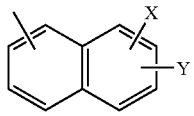

wherein X and Y each independently comprise H, halogen, $N_3$, NCS, CN, $NO_2$, $NX_1X_2$, $OX_3$, OAc, O-acyl, O-aroyl, NH-acyl, NH-aroyl, alcohol, CHO, $CF_3$, $COOX_3$, $SO_3H$, $SO_2NX_1X_2$, $CONX_1X_2$, alkoxy, alkylmercapto, alkylamino, di-alkylamino, alkylsulfinyl, alkylsulfonyl or (when Z comprises a structure having two adjacent carbon atoms) methylene dioxy.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$, $X_4$ comprises H or alkyl.

In a variation of the invention, R4 comprises —$(CH_2)_n$-Z.

n comprises an integer from 0 to about 7.

Z comprises an unsaturated ring having 5 ring atoms and 0 to 4 independently selected heteroatoms as ring members fused to an unsaturated ring having 5 ring atoms and 0 to 4 independently selected heteroatoms as ring members, an unsaturated ring having 5 ring atoms and 0 to 4 independently selected heteroatoms as ring members fused to an unsaturated ring having 6 or 7 ring atoms and 0 to 5 independently selected heteroatoms as ring members or an unsaturated ring having 6 ring atoms and 0 to 5 independently selected heteroatoms as ring members fused to an unsaturated ring having 6 or 7 ring atoms and 0 to 5 independently selected heteroatoms as ring members.

In a variation of the invention, R4 comprises —$CH_2$-Q-$(CH_2)_n$-Z.

Q comprises N, O, S, $CH_3$, $SO_2$ or $OSO_2$.

n is an integer from 0 to about 7.

Z comprises H, halogen, $N_3$, NCS, CN, $NO_2$, $NX_1X_2$, $OX_3$, OAc, O-acyl, O-aroyl, $O(CH_2)_dOH$, $O(CH_2)_dNX_1X_2$, NH-acyl, NH-aroyl, CHO, $CF_3$, $COOX_3$, $SO_3H$, $SO_2NX_1X_2$, $CONX_1X_2$, alkoxy, alkylmercapto, alkylamino or di-alkylamino.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl, or alkyl-$NX_1X_2$.

d is an integer from 0 to about 6.

In a variation of the invention, R4 comprises —$CH_2$-Q-$(CH_2)_n$-Z.

Q comprises N, O, S, $CH_3$, $SO_2$ or $OSO_2$.

n is an integer from 0 to about 7.

Z comprises a bicyclic ring, a heterobicyclic ring, a tricyclic ring, a heterotricyclic ring, a polycyclic ring or a heteropolycyclic ring.

In a variation of the invention, R4 comprises —$CH_2$-Q-$(CH_2)_n$-Z.

Q comprises N, O, S, $CH_3$, $SO_2$ or $OSO_2$.

n is an integer from 0 to about 7.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of the invention, R4 comprises —$CH_2$-Q-$(CH_2)_n$-Z.

Q comprises N, O, S, $CH_3$, $SO_2$ or $OSO_2$.

n is an integer from 0 to about 7.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of the invention R4 comprises —$CH_2$-Q-$(CH_2)_n$-Z.

Q comprises N, O, S, $CH_3$, $SO_2$ or $OSO_2$.

n is an integer from 0 to about 7.

Z comprises

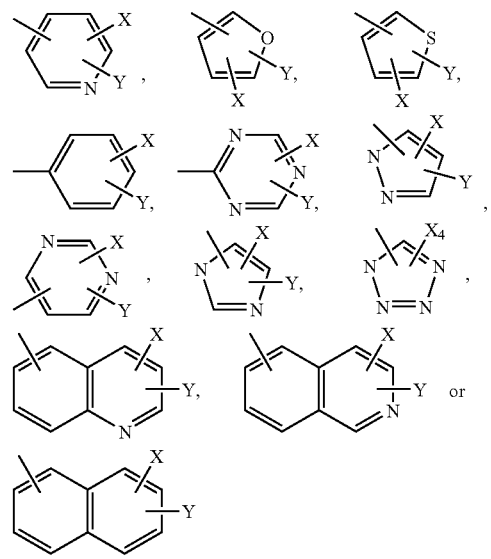

wherein X and Y each independently comprise H, halogen, $N_3$, NCS, CN, $NO_2$, $NX_1X_2$, $OX_3$, OAc, O-acyl, O-aroyl, NH-acyl, NH-aroyl, alcohol, CHO, $CF_3$, alcohol, $COOX_3$, $SO_3H$, $SO_2NX_1X_2$, $CONX_1X_2$, alkoxy, alkylmercapto, alkylamino, di-alkylamino, alkylsulfinyl, alkylsulfonyl or (when Z comprises a structure having two adjacent carbon atoms) methylenedioxy and $X_4$ comprises H or alkyl.

In a variation of the invention, R4 comprises —$(CH_2)_n$-Q-$(CH_2)_n$-Z.

Q comprises N, O, S, $CH_3$, $SO_2$ or $OSO_2$.

each n independently comprises an integer from 0 to about 7.

Z comprises an unsaturated ring having 5 ring atoms and 0 to 4 independently selected heteroatoms as ring members fused to an unsaturated ring having 5 ring atoms and 0 to 4 independently selected heteroatoms as ring members, an unsaturated ring having 5 ring atoms and 0 to 4 independently selected heteroatoms as ring members fused to an unsaturated ring having 6 or 7 ring atoms and 0 to 5 independently selected heteroatoms as ring members or an unsaturated ring having 6 ring atoms and 0 to 5 independently selected heteroatoms as ring members fused to an unsaturated ring having 6 or 7 ring atoms and 0 to 5 independently selected heteroatoms as ring members.

In a variation of the invention, R4 comprises —$CH_2Q$ $(CH_2)_n$-Z.

Q comprises N, O, S, $CH_3$, $SO_2$ or $OSO_2$.

n is an integer from 0 to about 7.

Z comprises

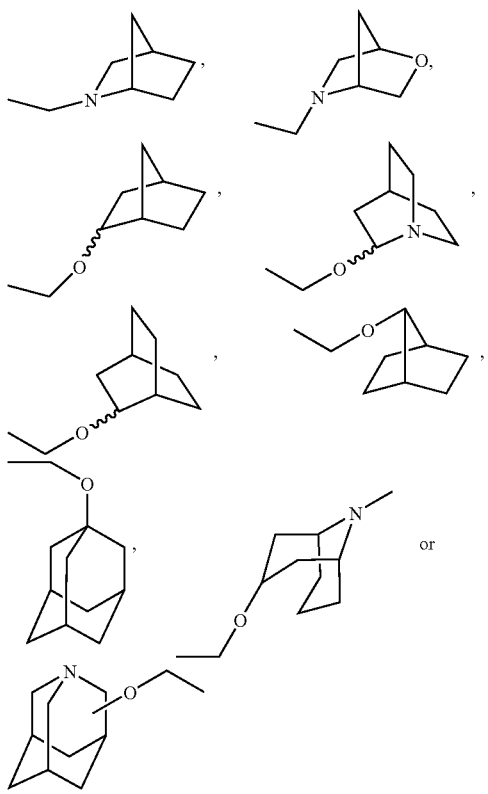

In a variation of the invention R4 comprises -T-$(CH_2)_n$-Z.

n comprises an integer from 0 to about 7.

T comprises a carbocyclic ring having 3 to about 8 ring members, an unsaturated ring having 3 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises H, halogen, $N_3$, NCS, CN, $NO_2$, $NX_1X_2$, $OX_3$, OAc, O-acyl, O-aroyl, $O(CH_2)_dOH$, $O(CH_2)_dNX_1X_2$, NH-acyl, NH-aroyl, CHO, $CF_3$, $COOX_3$, $SO_3H$, $SO_2NX_1X_2$, $CONX_1X_2$, alkoxy, alkylmercapto, alkylamino, di-alkylamino alkylsulfinyl or alkylsulfonyl.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$.

d is an integer from 0 to about 6.

In a variation of the invention R4 comprises -T-$(CH_2)_n$-Z.

n comprises an integer from 0 to about 7.

T comprises a carbocyclic ring having 3 to about 8 ring members, an unsaturated ring having 3 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises a carbocyclic ring having about 4 to about 7 ring members, a heterocyclic ring having about 4 to about 7 ring members, an aromatic ring having about 5 to about 7 ring members, a heteroaromatic ring having about 5 to about 7 ring members, a bicyclic ring, a heterobicyclic ring, a polycyclic ring, a heteropolycyclic ring; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of the invention R4 comprises -T-$(CH_2)_n$-Z.

n comprises an integer from 0 to about 7.

T comprises a carbocyclic ring having 3 to about 8 ring members, an unsaturated ring having 3 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises 1-, 2- or 3-pyrrolidinyl, 1-, 2-, 3- or 4-piperidinyl, 2-, 3- or 4-morpholinyl, 2-, 3- or 4-thiomorpholinyl, 1-, 2- or 3-azetidinyl, 1- or 2-piperazinyl, 2- or 3-tetrahydrofuranyl; or any above group substituted on at least one available ring atom by an alkyl group; or any above group substituted on at least one available ring nitrogen atom by a benzyl group, a substituted benzyl group, an alkoxybenzyl group, a substituted alkoxybenzyl group, a benzhydryl group or a substituted benzhydryl group; and wherein the connecting point between the —$(CH_2)_n$— group and the Z group can be any available ring carbon atom or any available ring nitrogen atom.

In a variation of the invention R4 comprises -T-$(CH_2)_n$-Z.

n comprises an integer from 0 to about 7.

T comprises a carbocyclic ring having 3 to about 8 ring members, an unsaturated ring having 3 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises

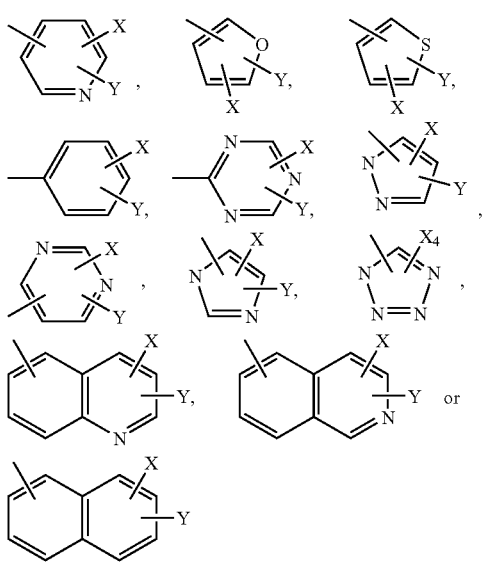

wherein X and Y each independently comprise H, halogen, $N_3$, NCS, CN, $NO_2$, $NX_1X_2$, $OX_3$, OAc, O-acyl, O-aroyl, NH-acyl, NH-aroyl, alcohol, CHO, $CF_3$, $COOX_3$, $SO_3H$, $SO_2NX_1X_2$, $CONX_1X_2$, alkoxy, alkylmercapto, alkylamino, di-alkylamino, alkylsulfinyl, alkylsulfonyl or (when Z comprises a structure having two adjacent carbon atoms) methylene dioxy.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$, $X_4$ comprises H or alkyl.

In a variation of the invention R4 comprises -T-$(CH_2)_n$-Z.

n comprises an integer from 0 to about 7.

T comprises a carbocyclic ring having 3 to about 8 ring members, an unsaturated ring having 3 to about 8 carbon atoms as ring members, a heterocyclic ring having 3 to about 8 ring members, a heteroaromatic ring having 5 to about 8 ring members, a bicyclic ring, a heterobicyclic ring, a tricyclic ring, a heterotricyclic ring, a polycyclic ring or a heteropolycyclic ring.

Z comprises an unsaturated ring having 5 ring atoms and 0 to 2 independently selected heteroatoms as ring members fused to an unsaturated ring having 5 ring atoms and 0 to 4 independently selected heteroatoms as ring members, an unsaturated ring having 5 ring atoms and 0 to 4 independently selected heteroatoms as ring members fused to an unsaturated ring having 6 or 7 ring atoms and 0 to 5 independently selected heteroatoms as ring members or an unsaturated ring having 6 ring atoms and 0 to 5 independently selected heteroatoms as ring members fused to an unsaturated ring having 6 or 7 ring atoms and 0 to 5 independently selected heteroatoms as ring members.

In another variation of the invention R4 comprises -Ph-$(CH_2)_n$-Z.

n comprises an integer from 0 to about 7.

Z comprises H, halogen, $N_3$, NCS, CN, $NO_2$, $NX_1X_2$, $OX_3$, OAc, O-acyl, O-aroyl, $O(CH_2)_dOH$, $O(CH_2)_dNX_1X_2$, NH-acyl, NH-aroyl, CHO, $CF_3$, $COOX_3$, $SO_3H$, $SO_2NX_1X_2$, $CONX_1X_2$, alkoxy, alkylmercapto, alkylamino or di-alkylamino.

$X_1$ and $X_2$ each independently comprise H or alkyl, or $X_1$ and $X_2$ together comprise part of a heterocyclic ring having about 4 to about 7 ring members and optionally heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$.

d is an integer from 0 to about 6.

In a variation of the invention, R4 comprises -Ph-$(CH_2)_n$-Z.

n comprises an integer from 0 to about 7.

Z comprises

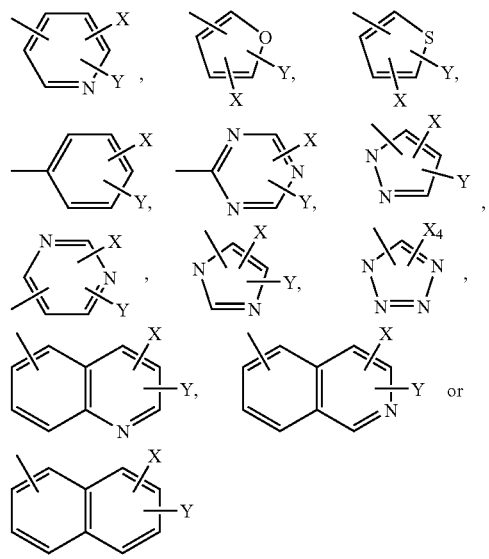

wherein X and Y each independently comprise H, halogen, $N_3$, NCS, CN, $NO_2$, $NX_1X_2$, $OX_3$, OAc, O-acyl, O-aroyl, NH-acyl, NH-aroyl, CHO, $CF_3$, alcohol, $COOX_3$, $SO_3H$, $SO_2NX_1X_2$, $CONX_1X_2$, alkoxy, alkylmercapto, alkylamino, di-alkylamino, alkylsulfinyl, lower-alkylsulfonyl or (when Z comprises a structure having two adjacent carbon atoms) methylene dioxy.

$X_1$ and $X_2$ each independently comprise H or alkyl, or $X_1$ and $X_2$ together comprise part of a heterocyclic ring having about 4 to about 7 ring members and optionally a second heteroatom selected from O, N or S, or $X_1$ and $X_2$ together comprise part of an imide ring having about 5 to about 6 members.

$X_3$ comprises H, alkyl, hydroxyloweralkyl or alkyl-$NX_1X_2$.

$X_4$ comprises H or alkyl.

In a variation of the invention R4 comprises -Ph-(CH$_2$)$_n$-Z.
n comprises an integer from 0 to about 7.
Z comprises

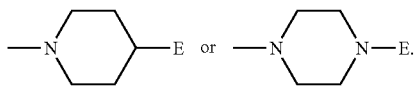

E comprises a C1 to about C4, linear or branched alkyl group, a phenyl group, a substituted phenyl group, a benzyl group or a substituted benzyl group.

In a variation of the invention R4 comprises -Ph-(CH$_2$)$_n$-Z.
n comprises an integer from 0 to about 7.
Z comprises

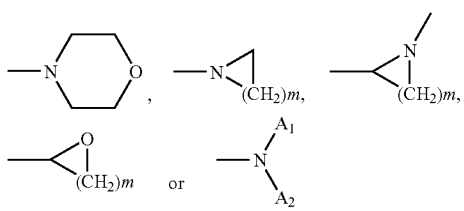

m is an integer from 1 to about 5. A$_1$ and A$_2$ each independently comprise a C1 to about C4 alkyl group, a phenyl group or a substituted phenyl group.

In any of the above R4 variations when A is a direct bond and B is N and R5 is hydrogen and R2 has a nitrogen directly connected to the nitrogen of the amide at the 3-position of pyrazole ring, then R4 can not be a phenyl ring or a phenyl ring having one to three substitutions selected from halogen, trifluoromethyl, 1-pyrrolidinyl, 1-piperidinyl, 4-morpholinyl, 1-piperazinyl, lower-alkyl substituted 1-pyrrolidinyl, lower-alkyl substituted 1-piperidinyl, lower-alkyl substituted 4-morpholinyl, and lower-alkyl substituted 1-piperazinyl.

R5 is present only when B is N and if present comprises H, alkyl or substituted alkyl.

It should be understood that:
when A is a direct bond and B is N then R1 cannot be H;
when A is not a direct bond and B is N then R3 cannot be H or a C1-C3 alkyl;
when A is a direct bond and B is N and R1 is a 6 member aromatic ring having 0 to 3 substituents independently selected from halogen, fluoromethyl and trifluoromethyl then R4 cannot be a 6 member aromatic ring having 0 to 3 substituents independently selected from halogen, fluoromethyl and trifluoromethyl;
when A is a direct bond and B is N and R5 is hydrogen and R2 has a nitrogen directly connected to the nitrogen of the amide at the 3-position of pyrazole ring, then R4 can not be a phenyl ring or a phenyl ring having one to three substitutions selected from halogen, trifluoromethyl, 1-pyrrolidinyl, 1-piperidinyl, 4-morpholinyl, 1-piperazinyl, lower-alkyl substituted 1-pyrrolidinyl, lower-alkyl substituted 1-piperidinyl, lower-alkyl substituted 4-morpholinyl, and lower-alkyl substituted 1-piperazinyl.

The inventive compounds include any and all isomers and steroisomers. In general, the compositions of the invention may be alternately formulated to comprise, consist of, or consist essentially of, any appropriate components herein disclosed. The compositions of the invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

Unless otherwise specifically defined, "acyl" refers to the general formula —C(O)alkyl.

Unless otherwise specifically defined, "acyloxy" refers to the general formula —O-acyl.

Unless otherwise specifically defined, "alcohol" refers to the general formula alkyl-OH and includes primary, secondary and tertiary variations.

Unless otherwise specifically defined, "alkyl" or "lower alkyl" refers to a linear, branched or cyclic alkyl group having from 1 to about 16 carbon atoms including, for example, methyl, ethyl, propyl, butyl, hexyl, octyl, isopropyl, isobutyl, tert-butyl, cyclopropyl, cyclohexyl, cyclooctyl, vinyl and allyl. The alkyl group can be saturated or unsaturated. The alkyl group can be unsubstituted, singly substituted or, if possible, multiply substituted, with substituent groups in any possible position. Unless otherwise specifically limited, a cyclic alkyl group includes monocyclic, bicyclic, tricyclic, tetracyclic and polycyclic rings, for example norbornyl, adamantyl and related terpenes.

Unless otherwise specifically defined, "alkoxy" refers to the general formula —O-alkyl.

Unless otherwise specifically defined, "alkylmercapto" refers to the general formula —S-alkyl.

Unless otherwise specifically defined, "alkylamino" refers to the general formula —(NH)-alkyl.

Unless otherwise specifically defined, "di-alkylamino" refers to the general formula —N-(alkyl)$_2$. Unless otherwise specifically limited di-alkylamino includes cyclic amine compounds such as piperidine and morpholine.

Unless otherwise specifically defined, an aromatic ring is an unsaturated ring structure having about 5 to about 7 ring members and including only carbon as ring atoms. The aromatic ring structure can be unsubstituted, singly substituted or, if possible, multiply substituted, with substituent groups in any possible position.

Unless otherwise specifically defined, "aryl" refers to an aromatic ring system that includes only carbon as ring atoms, for example phenyl, biphenyl or naphthyl. The aryl group can be unsubstituted, singly substituted or, if possible, multiply substituted, with substituent groups in any possible position.

Unless otherwise specifically defined, "aroyl" refers to the general formula —C(=O)-aryl.

Unless otherwise specifically defined, a bicyclic ring structure comprises 2 fused rings that include only carbon as ring atoms. The bicyclic ring structure can be saturated or unsaturated. The bicyclic ring structure can be unsubstituted, singly substituted or, if possible, multiply substituted, with substituent groups in any possible position. The individual rings may or may not be of the same type. Examples of bicyclic ring structures include naphthalene and bicyclooctane.

Unless otherwise specifically defined, a carbocyclic ring is a non-aromatic ring structure, saturated or unsaturated, having about 3 to about 8 ring members that includes only carbon as ring atoms, for example, benzene or cyclohexane. The carbocyclic ring can be unsubstituted, singly substituted or, if possible, multiply substituted, with substituent groups in any possible position.

Unless otherwise specifically defined, "halogen" refers to an atom selected from fluorine, chlorine, bromine and iodine.

Unless otherwise specifically defined, a heteroaromatic ring is an unsaturated ring structure having about 5 to about 8 ring members independently selected from carbon atoms and one or more heteroatoms, including oxygen, nitrogen and/or sulfur, for example, pyridine, furan, quinoline, and their derivatives. The heteroaromatic ring can be unsubstituted, singly substituted or, if possible, multiply substituted, with substituent groups in any possible position.

Unless otherwise specifically defined, a heterobicyclic ring structure comprises 2 fused rings having ring members independently selected from carbon and one or more heteroatoms, including oxygen, nitrogen and/or sulfur. The heterobicyclic ring structure is typically unsaturated. The heterobicyclic ring can be unsubstituted, singly substituted or, if possible, multiply substituted, with substituent groups in any possible position. The individual rings may or may not be of the same type. Examples of heterobicyclic ring structures include isobenzofuran and indole.

Unless otherwise specifically defined, a heterocyclic ring is a saturated ring structure having about 3 to about 8 ring members independently selected from carbon atoms and one or more heteroatoms, including oxygen, nitrogen and/or sulfur; for example, piperidine, morpholine, piperazine, pyrrolidine, thiomorpholine, and their derivatives. The heterocyclic ring can be unsubstituted, singly substituted or, if possible, multiply substituted, with substituent groups in any possible position.

Unless otherwise specifically defined, a heterotricyclic ring structure comprises 3 fused rings having ring members independently selected from carbon and one or more heteroatoms, including oxygen, nitrogen and/or sulfur. The heterotricyclic ring structure is typically unsaturated. The heterotricyclic ring structure can be unsubstituted, singly substituted or, if possible, multiply substituted, with substituent groups in any possible position. The individual rings may or may not be of the same type. Examples of heterotricyclic ring structures include carbazole, phenanthroline and phenazine.

Unless otherwise specifically defined, a heteropolycyclic ring structure comprises more than 3 fused rings having ring members independently selected from carbon and one or more heteroatoms, including oxygen, nitrogen and/or sulfur. The heteropolycyclic ring structure is typically unsaturated. The heteropolycyclic ring structure can be unsubstituted, singly substituted or, if possible, multiply substituted, with substituent groups in any possible position. The individual rings may or may not be of the same type. Examples of heteropolycyclic ring structures include azaadamantine, tropane and homotropane.

Unless otherwise specifically defined, the term "phenacyl" refers to the general formula -phenyl-acyl.

Unless otherwise specifically defined, a polycyclic ring structure comprises more than 3 fused rings and includes carbon as ring atoms. The polycyclic ring structure can be saturated or unsaturated. The polycyclic ring structure can be unsubstituted, singly substituted or, if possible, multiply substituted, with substituent groups in any possible position. The individual rings may or may not be of the same type. Examples of polycyclic ring structures include adamantine, bicyclooctane, norbornane and bicyclononanes.

Unless otherwise specifically defined, a spirocycle refers to a ring system wherein a single atom is the only common member of two rings. A spirocycle can comprise a saturated carbocyclic ring comprising about 3 to about 8 ring members, a heterocyclic ring comprising about 3 to about 8 ring atoms wherein up to about 3 ring atoms may be N, S, or O or a combination thereof.

Unless otherwise specifically defined, a tricyclic ring structure comprises 3 fused rings and includes carbon as ring atoms. The tricyclic ring structure can be saturated or unsaturated. The tricyclic ring structure can be unsubstituted, singly substituted or, if possible, multiply substituted, with substituent groups in any possible position and may be substituted or unsubstituted. The individual rings may or may not be of the same type. Examples of tricyclic ring structures include fluorene and anthracene.

Substituent groups for the above moieties useful in the invention are those groups that do not significantly diminish the biological activity of the inventive compound. Substituent groups that do not significantly diminish the biological activity of the inventive compound include, for example, H, halogen, $N_3$, NCS, CN, $NO_2$, $NX_1X_2$, $OX_3$, OAc, O-acyl, O-aroyl, NH-acyl, NH-aroyl, NHCOalkyl, CHO, $CF_3$, $COOX_3$, $SO_3H$, $PO_3H_2$, $SO_2NX_1X_2$, $CONX_1X_2$, alkyl, alcohol, alkoxy, alkylmercapto, alkylamino, di-alkylamino, sulfonamide, thioalkoxy or methylene dioxy when the substituted structure has two adjacent carbon atoms, wherein $X_1$ and $X_2$ each independently comprise H or alkyl, or $X_1$ and $X_2$ together comprise part of a heterocyclic ring having about 4 to about 7 ring members and optionally one additional heteroatom selected from O, N or S, or $X_1$ and $X_2$ together comprise part of an imide ring having about 5 to about 6 members and $X_3$ comprises H, alkyl, hydroxyloweralkyl, or alkyl-$NX_1X_2$. Unless otherwise specifically limited a substituent group may be in any possible position.

Some of the inventive compounds showed a high affinity for at least one of the cannabinoid receptors. Thus, an aspect of the invention is use of at least one of the inventive compounds to interact with cannabinoid receptors.

Some of the novel pyrazole derivatives show selectivity for the CB1 cannabinoid receptor. These inventive CB1 selective analogs are able to interact with the CB1 receptor without affecting the peripheral (CB2) receptor to the same degree. Therefore, still another aspect of the invention is use of at least one of the inventive compounds to preferentially interact with the CB1 receptor.

Additionally, known cannabimimetic pyrazole ligands generally have long in vivo half-lives and are more lipophilic than desired for optimal in vivo activity. Some of the novel pyrazole analogs described herein are less lipophilic than known cannabimimetic pyrazole ligands and have shorter in vivo half-lives then known pyrazole analogs, providing the compounds of this embodiment with a favorable therapeutic profile. Therefore, yet another aspect of the invention is a cannabimimetic pyrazole analog that is less lipophilic than known cannabimimetic pyrazole analogs.

Some of the novel pyrazole analogs described herein are CB1 cannabinoid receptor antagonists that prevent binding of endogenous agonists to the cannabinoid receptors and thereby block the biological actions of such endogenous agonists. Therefore, a further aspect of the invention is use of at least one of the inventive compounds to prevent binding of a cannabinoid agonist to the CB1 cannabinoid receptor.

The inventive pyrazole analogs described herein, and physiologically acceptable salts thereof, have pharmacological properties when administered in therapeutically effective amounts for providing a physiological effect useful to treat marijuana abuse, obesity, schizophrenia, epilepsy, stress, memory disorders, migraine, vomiting, thymic disorders, dyskinesia, kinetic disorder, anxiety disorders, psychotic disorders, cognitive disorders, appetite disorders, mood disorders, delirious disorders, neuropathies, Parkinson's disease, Alzheimer's disease, depression, psychosomatic-induced disease, as well as for alcohol, opioid, nicotine and cocaine addiction, etc. Additionally, these analogs can be used in cancer chemotherapy. Thus, another aspect of the invention is the administration of a therapeutically effective amount of an inventive compound, or a physiologically acceptable salt thereof, to an individual or animal to provide a physiological effect.

A better understanding of the invention will be obtained from the following detailed description of the article and the desired features, properties, characteristics, and the relation of the elements as well as the process steps, one with respect to each of the others, as set forth and exemplified in the description and illustrative embodiments.

DESCRIPTION OF SOME PREFERRED EMBODIMENTS

Figure 1:
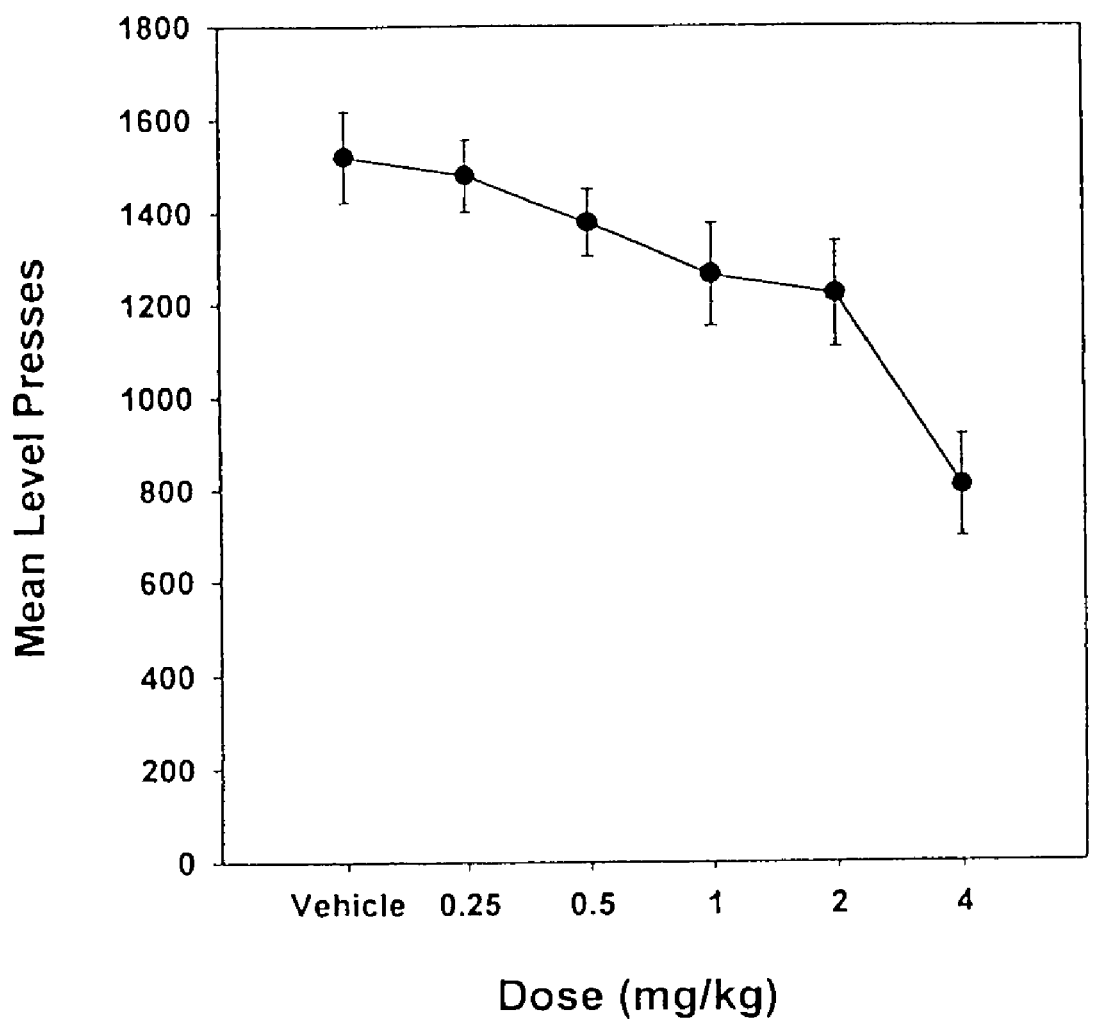
FIG. 1 is a graph of a dose vs. response curve for inventive compound 1-5.

As used herein a "therapeutically effective amount" of a compound, is the quantity of a compound which, when administered to an individual or animal, results in a sufficiently high level of that compound in the individual or animal to cause a physiological response. The inventive compounds described herein, and physiologically acceptable salts thereof, have pharmacological properties when administered in therapeutically effective amounts for providing a physiological response useful to treat marijuana abuse, obesity, schizophrenia, epilepsy, stress, memory disorders, migraine, vomiting, thymic disorders, dyskinesia, kinetic disorder, anxiety disorders, psychotic disorders, cognitive disorders, appetite disorders, mood disorders, delirious disorders, neuropathies, Parkinson's disease, Alzheimer's disease, depression, psychosomatic-induced disease, as well as for alcohol, opioid, nicotine and cocaine addiction, etc. Additionally, these analogs can be useful in cancer chemotherapy. Typically, a "therapeutically effective amount" of an inventive compound is believed to range from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration.

Such forms include, but are not limited to, capsular and tablet formulations (for oral and rectal administration), liquid formulations (for oral, intravenous, intramuscular, subcutaneous, ocular, intranasal, inhalation-based and transdermal administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles include, for example, saline, sterile water, Ringer's solution and isotonic sodium chloride solutions. The specific dosage level of active ingredient will depend upon a number of factors, including, for example, biological activity of the particular preparation, age, body weight, sex and general health of the individual being treated.

The following examples are given for purposes of illustration only in order that the present invention may be more fully understood. These examples are not intended to limit in any way the scope of the invention unless otherwise specifically indicated.

EXAMPLES

A number of inventive cannabimimetic pyrazole derivatives were prepared. Table 1 illustrates some prepared CB1 selective pyrazole analogs (compounds 1-1 to 1-29).

TABLE 1

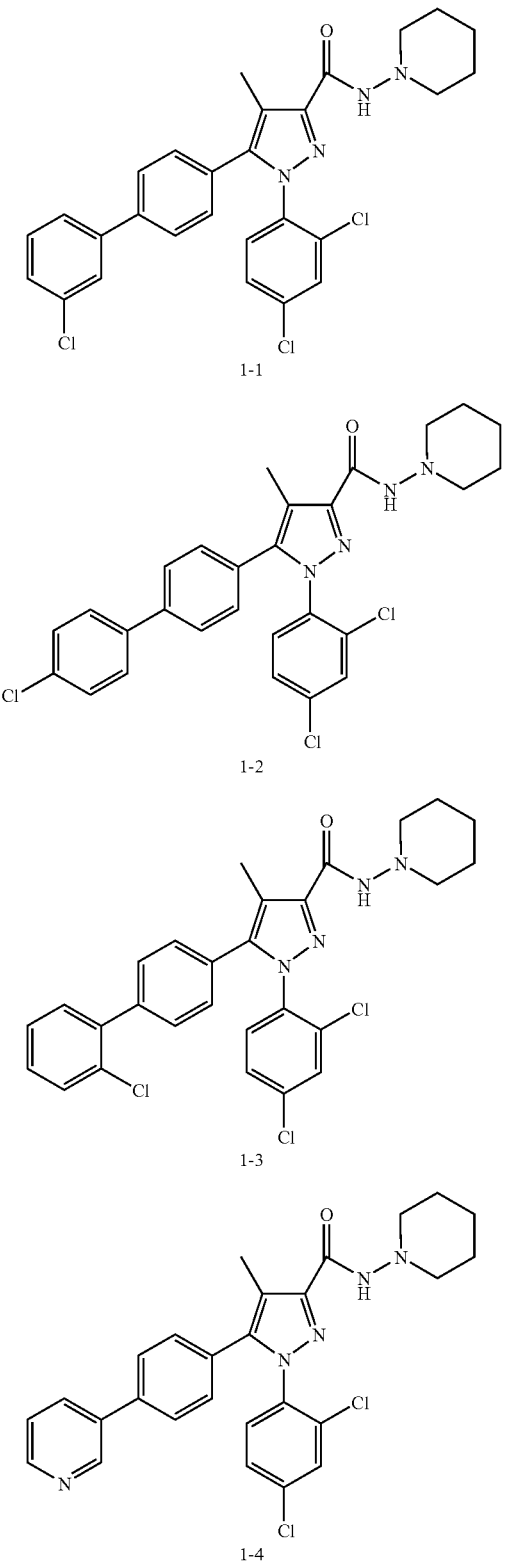

TABLE 1-continued
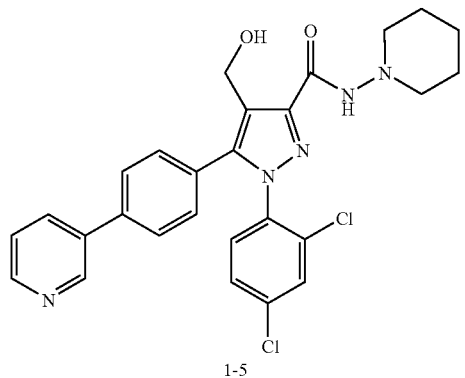
1-5
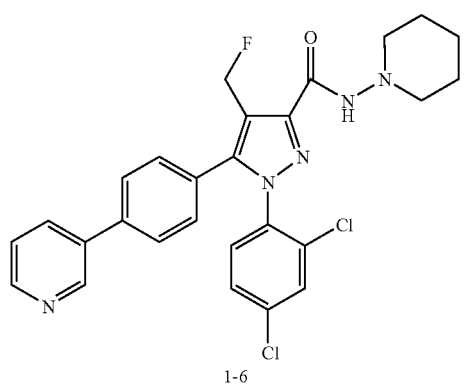
1-6
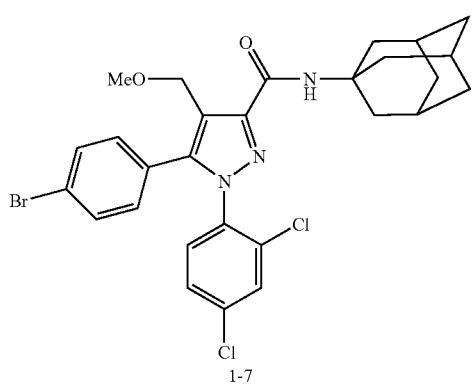
1-7
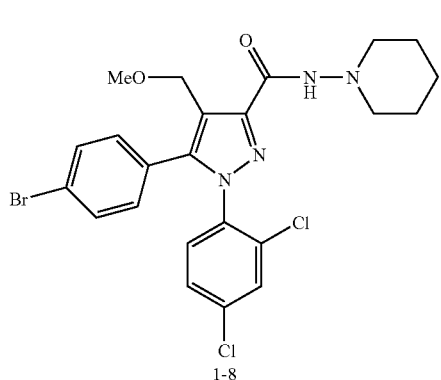
1-8
TABLE 1-continued
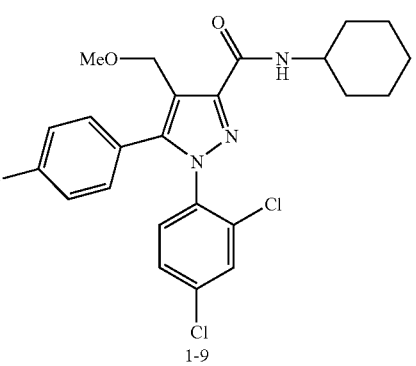
1-9
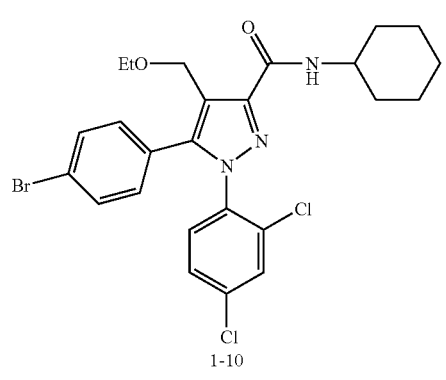
1-10
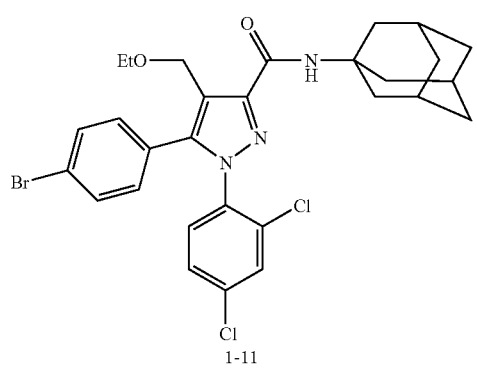
1-11
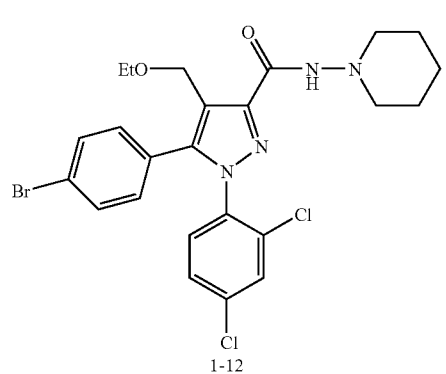
1-12

TABLE 1-continued
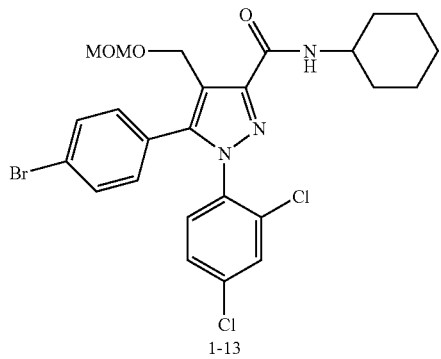
1-13
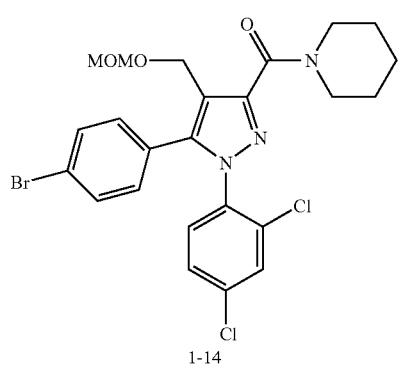
1-14
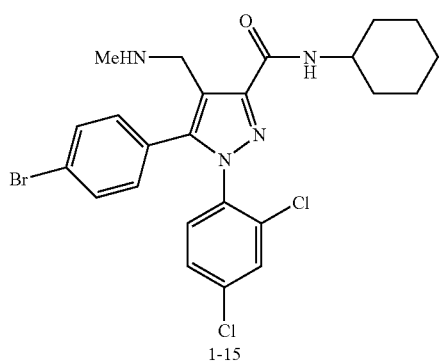
1-15
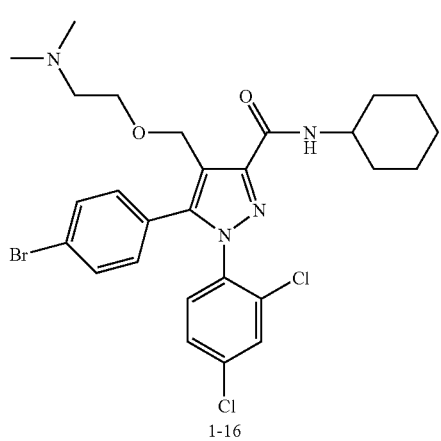
1-16
TABLE 1-continued
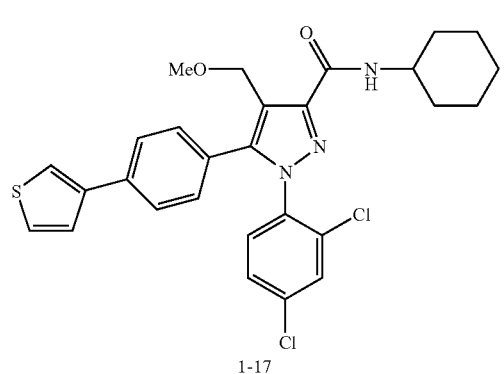
1-17
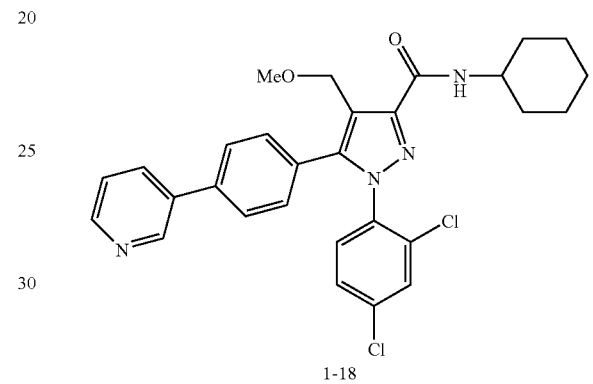
1-18
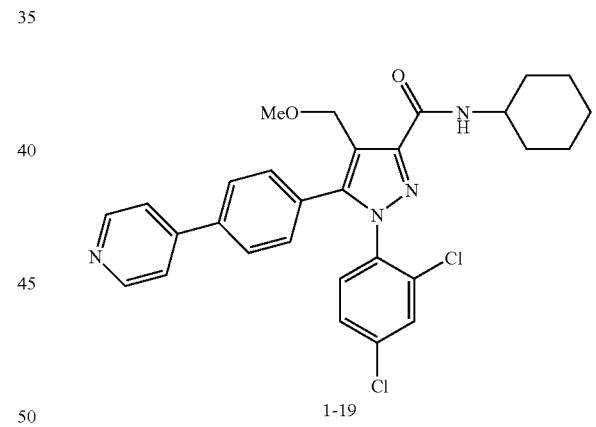
1-19
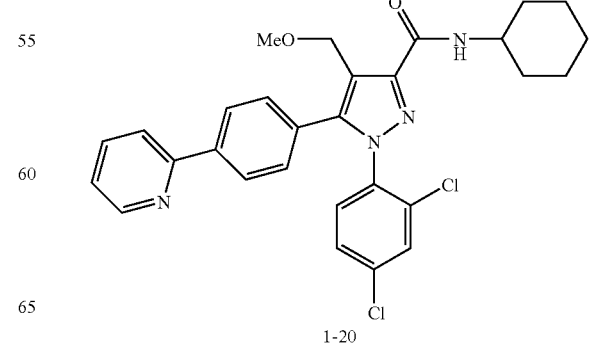
1-20

TABLE 1-continued
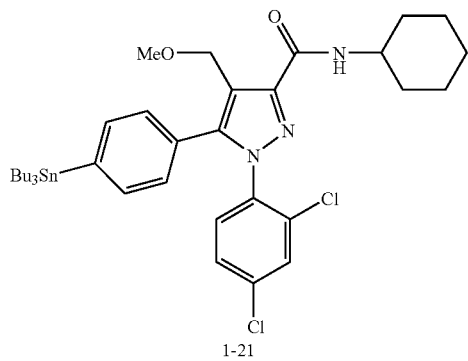
1-21
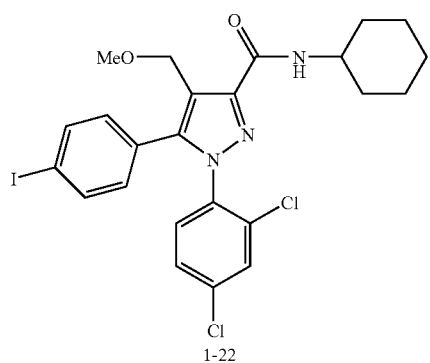
1-22
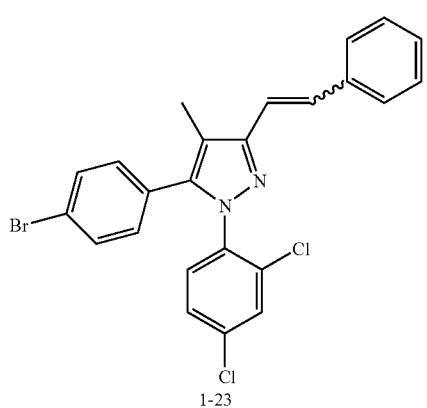
1-23
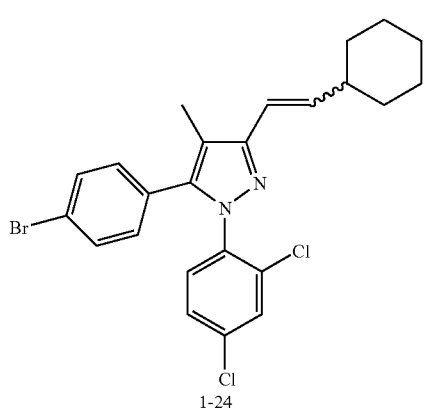
1-24
TABLE 1-continued
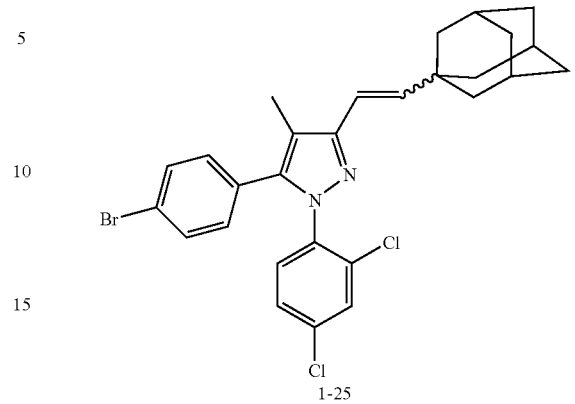
1-25
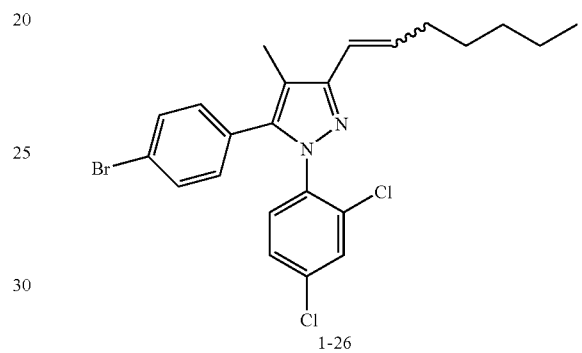
1-26
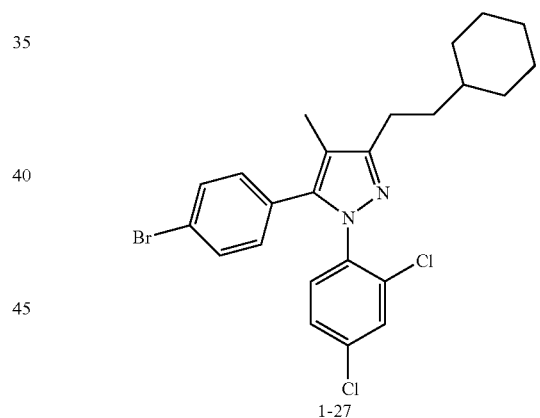
1-27
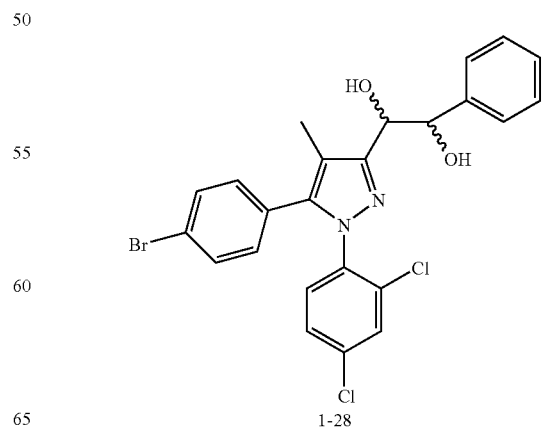
1-28

TABLE 1-continued
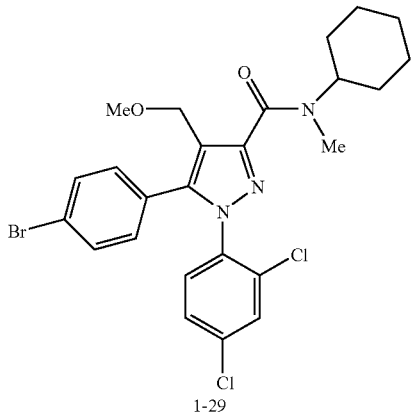
1-29
Table 2 illustrates some prepared CB1 selective pyrazole analogs (compounds 2-1 to 2-22)
TABLE 2
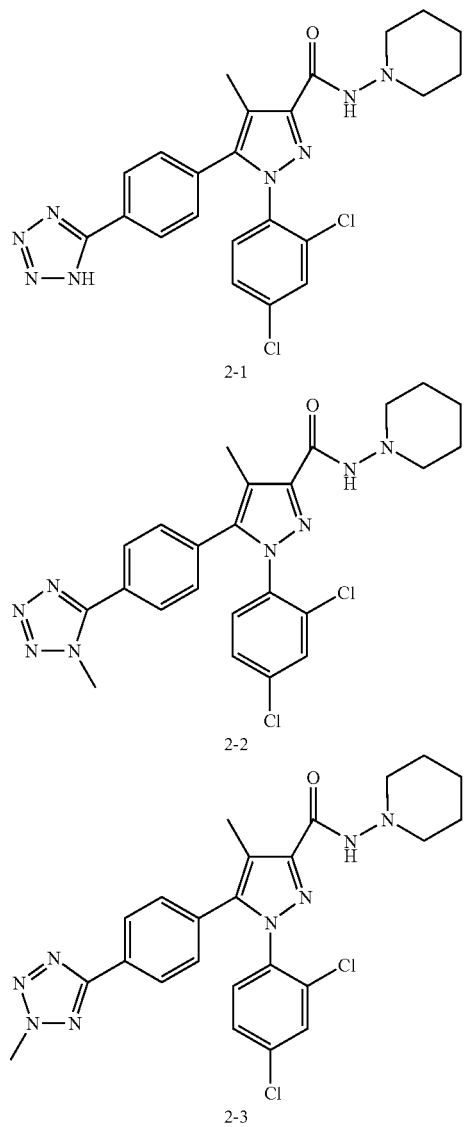
2-1
2-2
2-3
TABLE 2-continued
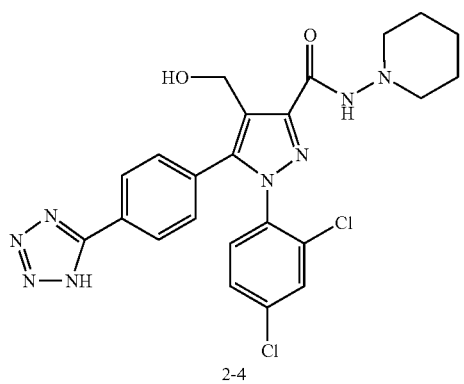
2-4
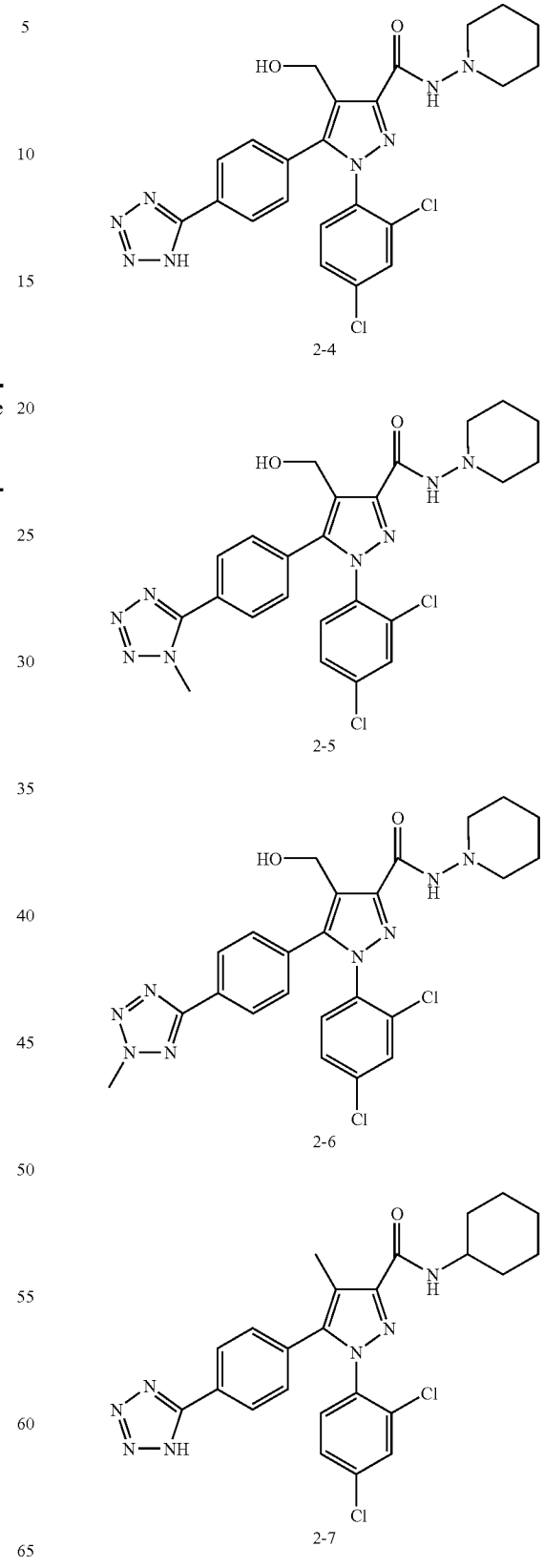
2-5
2-6
2-7

TABLE 2-continued
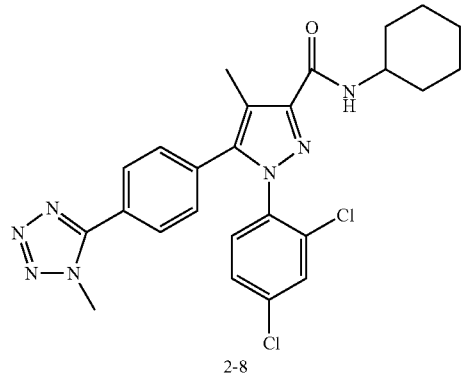
2-8
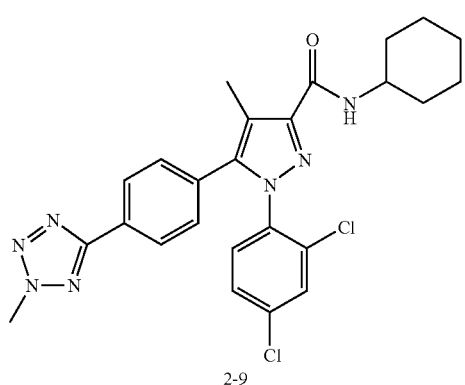
2-9
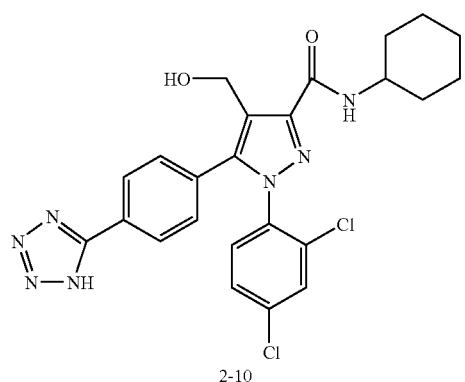
2-10
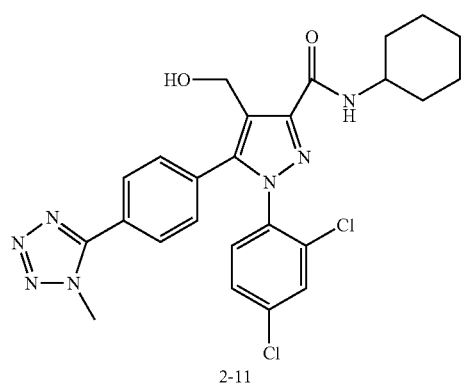
2-11
TABLE 2-continued
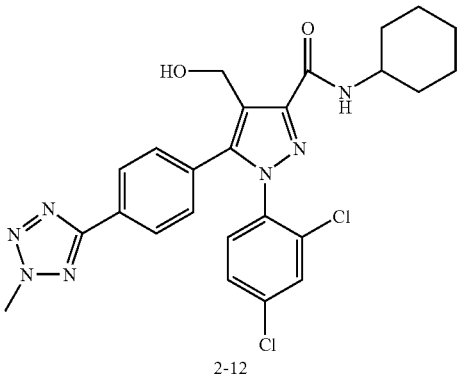
2-12
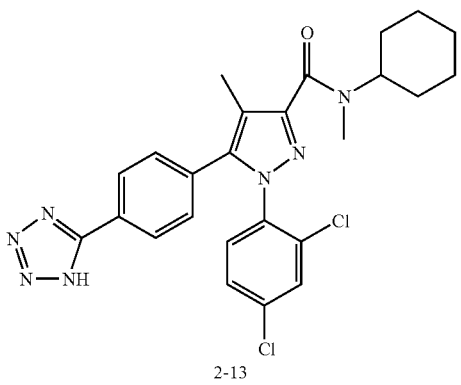
2-13
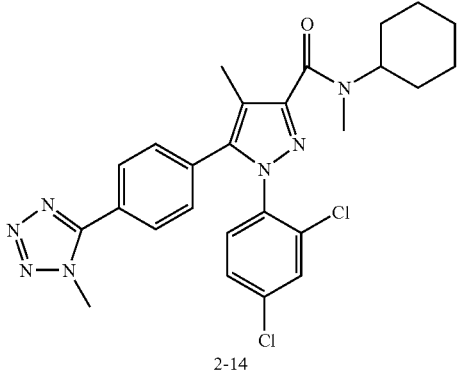
2-14
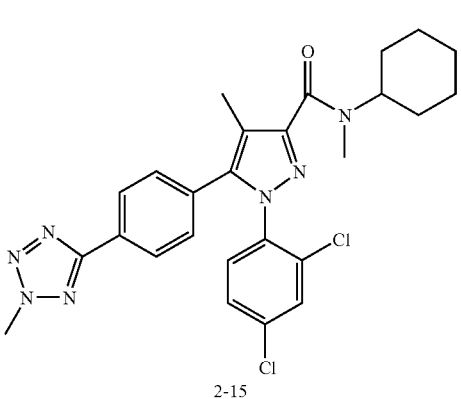
2-15

TABLE 2-continued
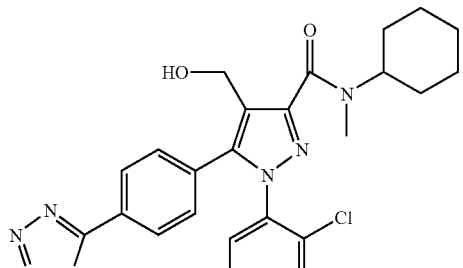
2-16
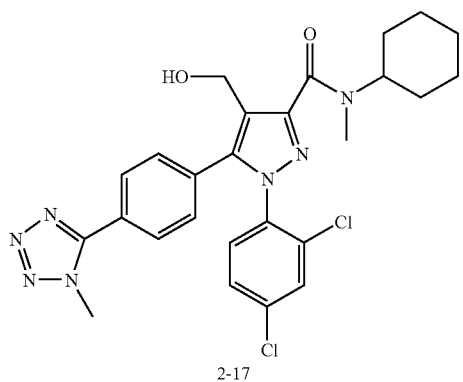
2-17
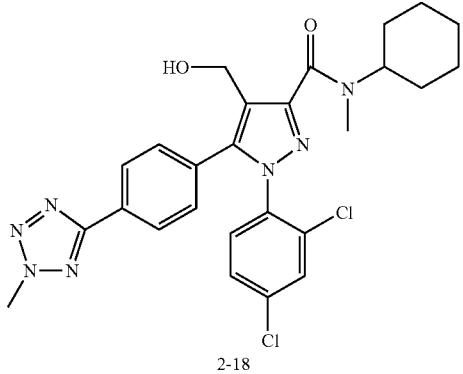
2-18
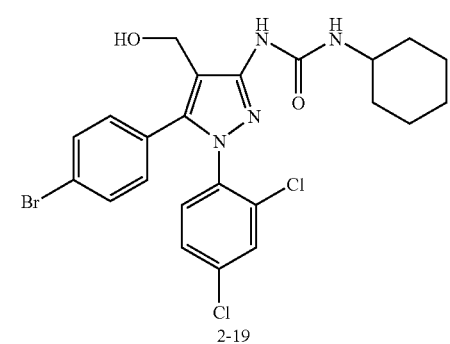
2-19
TABLE 2-continued
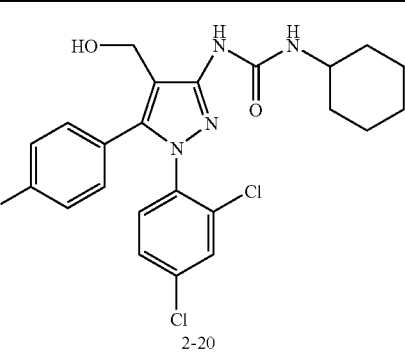
2-20
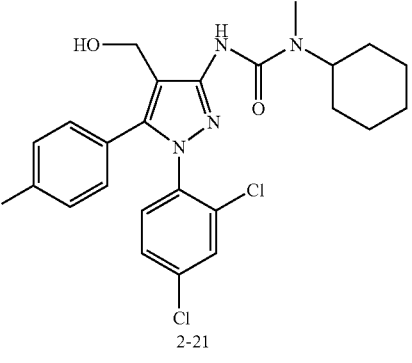
2-21
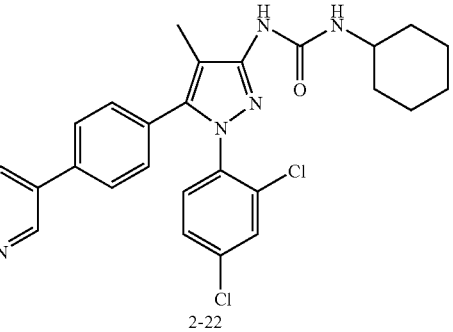
2-22
Table 3 illustrates some prepared pyrazole analogs (compounds 3-1 to 3-25).
TABLE 3
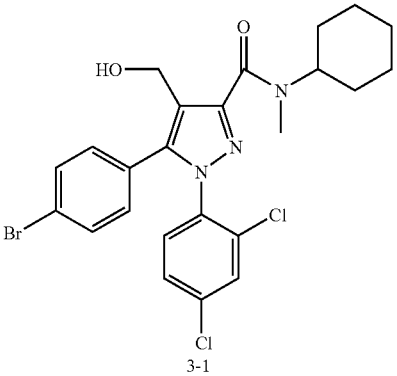
3-1

TABLE 3-continued
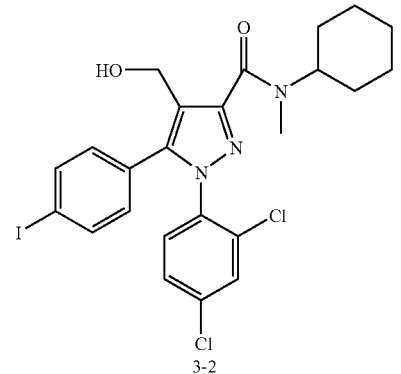
3-2
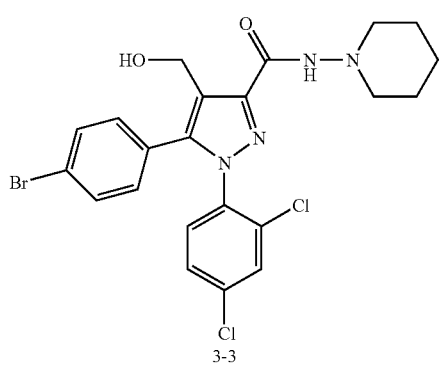
3-3
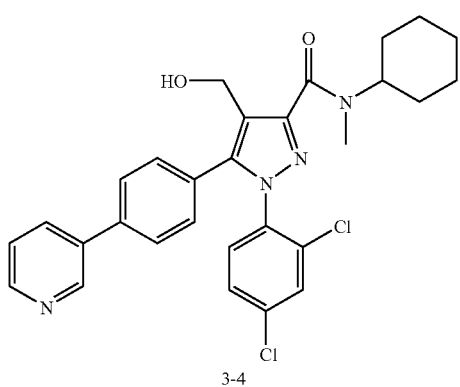
3-4
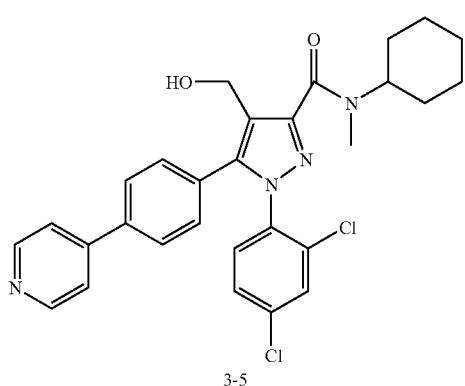
3-5
TABLE 3-continued
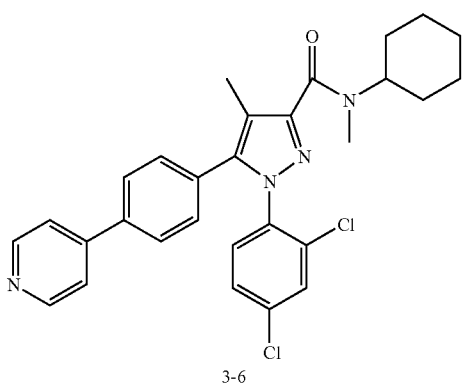
3-6
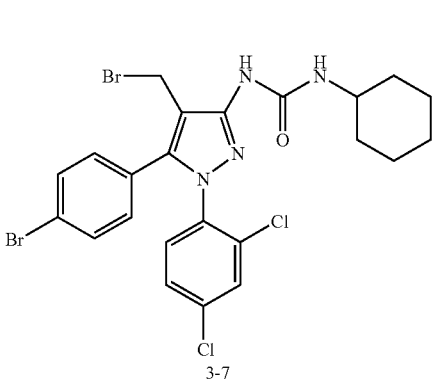
3-7
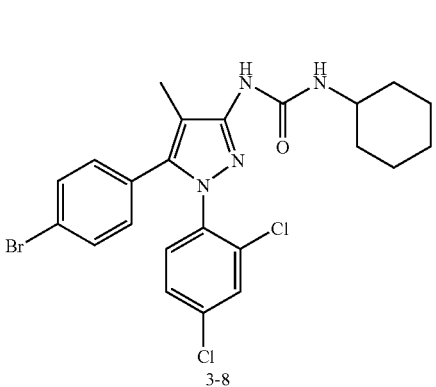
3-8
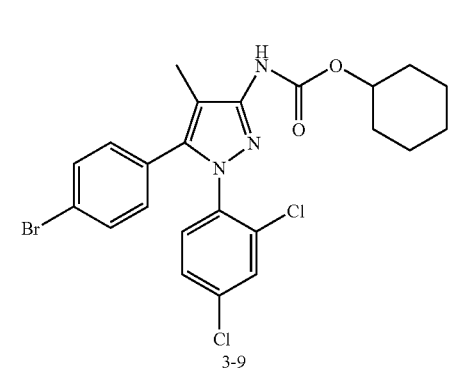
3-9

TABLE 3-continued
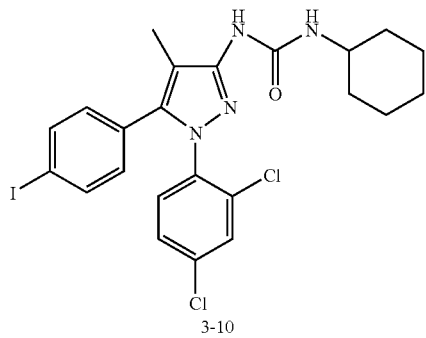
3-10
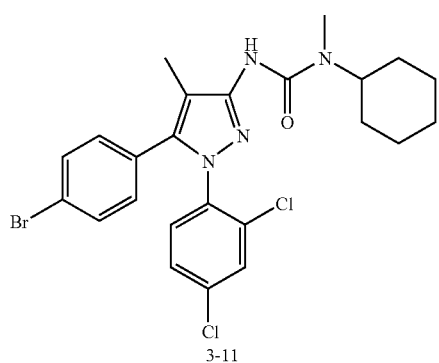
3-11
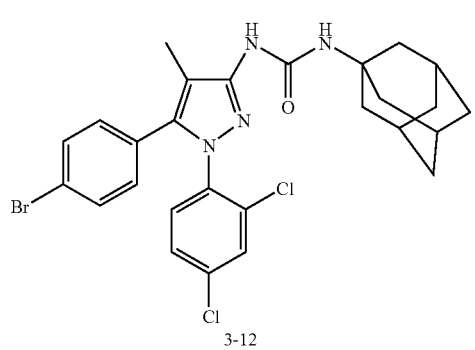
3-12
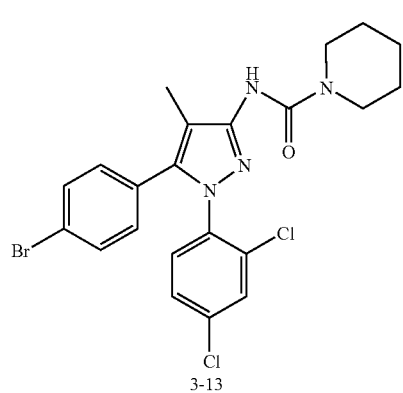
3-13
TABLE 3-continued
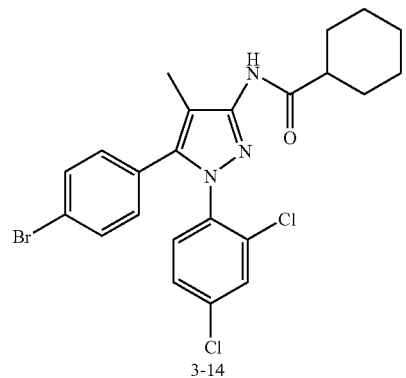
3-14
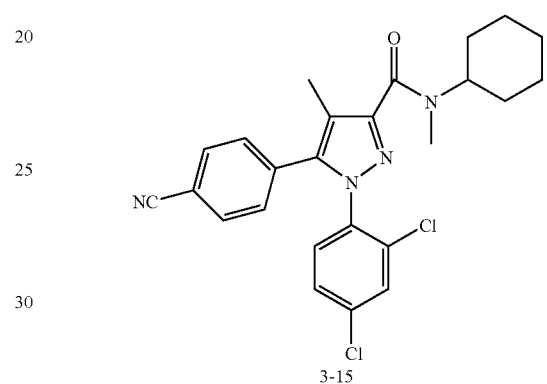
3-15
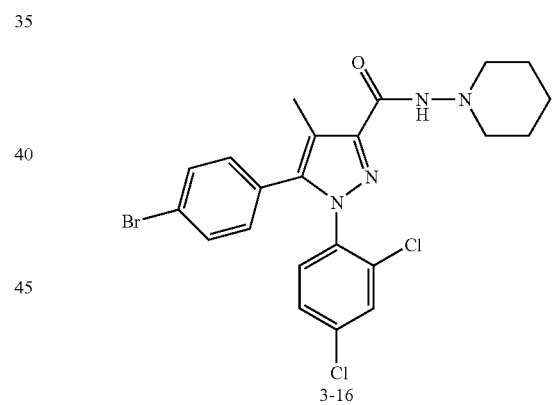
3-16
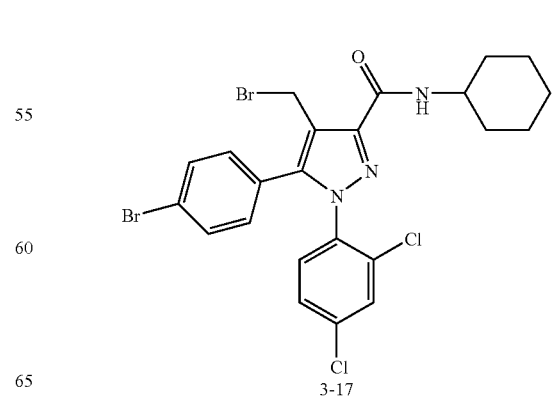
3-17

TABLE 3-continued

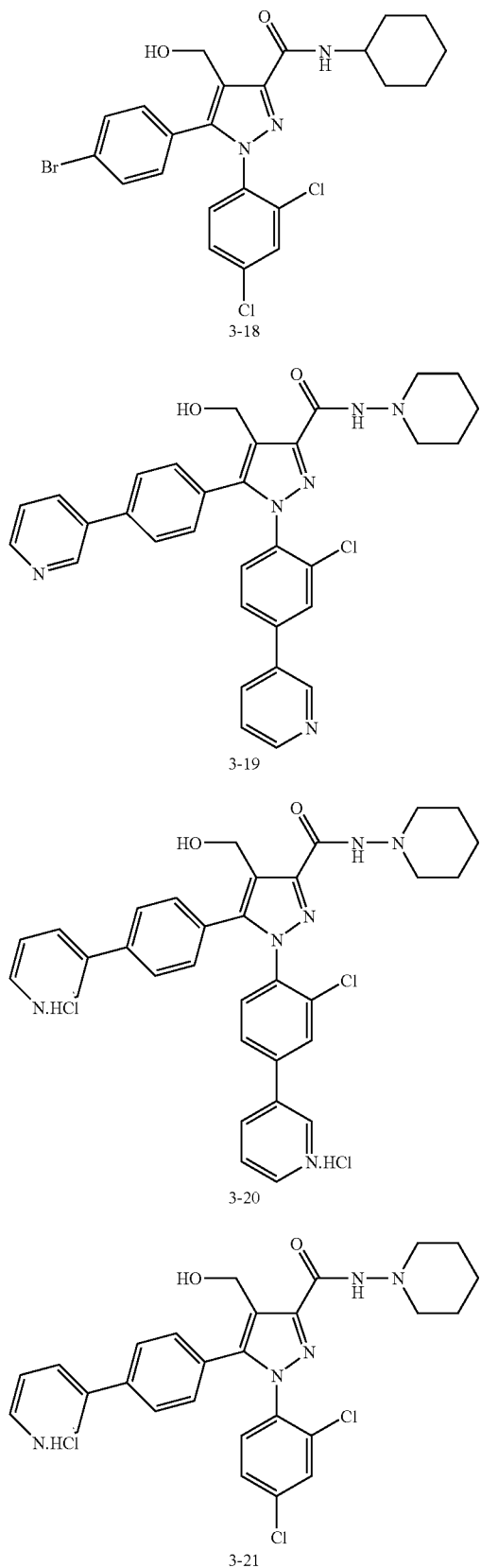

TABLE 3-continued

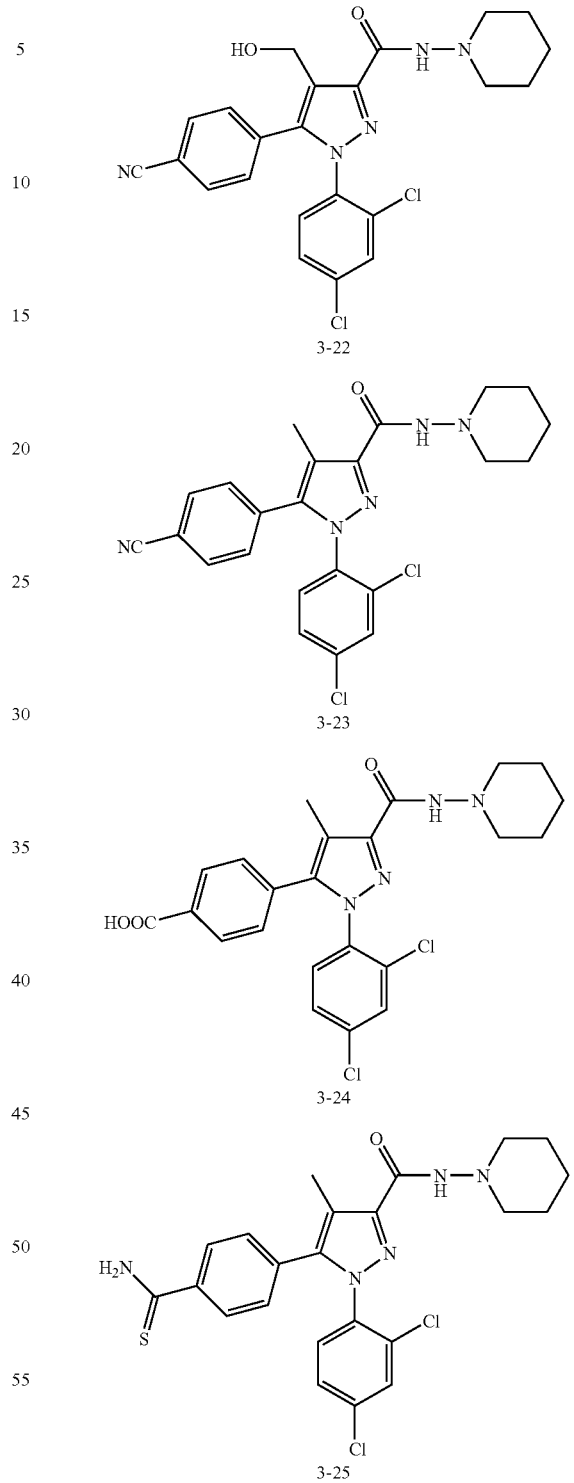

Some of the inventive analogs were tested for CB2 receptor binding affinity and for CB1 receptor affinity (to determine selectivity). As used herein, "binding affinity" is represented by the $K_i$ value which is the inhibition constant correlated with the concentration of an analog required to occupy the 50% of the total number (Bmax) of the receptors. The lower the $K_i$ value the higher the binding affinity. As used herein an analog is said to have "binding selectivity" if it has higher binding affinity for one receptor compared to the other receptor; e.g. a cannabinoid analog which has a $K_i$ of 0.1 nM for CB1 and 10 nM for CB2, is 100 times more selective for the CB1 receptor.

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, *5'-azido $\Delta^8$-THC: A Novel Photoaffinity Label for the Cannabinoid Receptor*, J. Med. Chem., 35, 3076-3079 (1992) with the following changes. The above articles are incorporated by reference herein.

Membranes, previously frozen at –80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [3H] CP-55,940, and various concentrations of test materials in a final volume of 200 μL. The assays were incubated for 1 hour at 30° C. and then immediately filtered using Packard Filtermate 196 harvester and Whatman GF/C filterplates and washed with wash buffer (TME) containing 0.5% BSA. Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of Inhibitor which causes 50% Inhibition ($IC_{50}$) of an Enzymatic Reaction*, Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

For the compounds of Table 1 the CB1 cannabinoid receptor binding affinities (Ki) for the synthesized analogs range between 1.51 and 85.1. The CB2 cannabinoid receptor binding affinities (Ki) for the synthesized analogs range between 5.81 and 2312. The CB1 cannabinoid receptor selectivity for some of the synthesized analogs range from about 2 to about 452. The CB2 cannabinoid receptor selectivity for some of the synthesized analogs range from about 1 to about 4. The results are summarized in Table 4.

TABLE 4

| | affinities | | selectivity | |
|---|---|---|---|---|
| cmpnd no. | CB1 | CB2 | CB1 | CB2 |
| 1-1 | 1.5 | 741 | 491 | |
| 1-2 | 5.8 | 1595 | 274 | |
| 1-3 | 85.1 | 1370 | 16 | |
| 1-4 | 11.2 | 1326 | 118 | |
| 1-5 | 5.8 | 2312 | 398 | |
| 1-6 | 15.1 | 1927 | 128 | |
| 1-7 | 53 | 1676 | 32 | |
| 1-8 | 19 | 561 | 31 | |
| 1-9 | 4 | 495 | 124 | |
| 1-10 | 54 | 842 | 16 | |
| 1-11 | 105 | 47460 | 452 | |
| 1-12 | 46 | 490 | 11 | |
| 1-13 | 15 | 54 | 3.6 | |
| 1-14 | 395 | 3102 | 7.8 | |
| 1-15 | 172 | 397 | 2.3 | |
| 1-16 | 24 | 140 | 5.8 | |
| 1-17 | 241 | 968 | 4.0 | |
| 1-18 | 62 | 646 | 10.4 | |
| 1-19 | 160 | 2980 | 18.6 | |
| 1-20 | 51 | 277 | 5.4 | |
| 1-21 | 2970 | 2744 | | 1.1 |
| 1-22 | 15 | 675 | 45 | |
| 1-23 | 331 | 16420 | 49.6 | |
| 1-24 | 141 | 10570 | 75.0 | |
| 1-25 | 17680 | 4006 | | 4.4 |
| 1-26 | 7677 | 52890 | 6.9 | |
| 1-27 | 1043 | 26390 | 25.3 | |
| 1-28 | 1067 | 3926 | 3.7 | |
| 1-29 | 273 | 2038 | 7.5 | |

For the compounds of Table 2 the CB1 cannabinoid receptor binding affinities (Ki) for the synthesized analogs range between 6 and 1844. The CB2 cannabinoid receptor binding affinities (Ki) for the synthesized analogs range between 36.5 and 13585. The CB1 cannabinoid receptor selectivity for some of the synthesized analogs range from about 1 to about 546. The CB2 cannabinoid receptor selectivity for compound 2-14 was 1.4. The results are summarized in Table 5.

TABLE 5

| | affinities | | selectivity | |
|---|---|---|---|---|
| cmpnd no. | CB1 | CB2 | CB1 | CB2 |
| 2-1 | 455 | 702 | 1.5 | |
| 2-2 | 90 | 242 | 2.7 | |
| 2-3 | 6 | 517 | 86.2 | |
| 2-4 | 1844 | 13585 | 7.4 | |
| 2-5 | 203 | 2128 | 10.5 | |
| 2-6 | 18 | 2170 | 120.5 | |
| 2-8 | 120 | 1069 | 8.9 | |
| 2-9 | 20 | 381 | 19 | |
| 2-10 | 192 | 463 | 2.4 | |
| 2-11 | 118 | 122 | 1 | |
| 2-12 | 37 | 36.5 | 1 | |
| 2-13 | 543 | 6361 | 117.8 | |
| 2-14 | 1271 | 941 | | 1.4 |
| 2-15 | 105 | 551 | 5.2 | |
| 2-16 | 293 | 1119 | 3.8 | |
| 2-17 | 1082 | 1414 | 1.3 | |
| 2-18 | 210 | 641 | 3.0 | |
| 2-19 | 9 | 4920 | 546.7 | |
| 2-21 | 296 | 4473 | 15.1 | |
| 2-22 | 29 | 10863 | 374.6 | |

For the compounds of Table 3 the CB1 cannabinoid receptor binding affinities (Ki) for the synthesized analogs range between 6 and 4232. The CB2 cannabinoid receptor binding affinities (Ki) for the synthesized analogs range between 127 and 27054. The CB1 cannabinoid receptor selectivity for some of the synthesized analogs range from about 1.3 to about 838. The results are summarized in Table 6.

TABLE 6

| cmpnd no. | affinities | | selectivity |
| --- | --- | --- | --- |
| | CB1 | CB2 | CB1 |
| 3-1 | 29 | 1802 | 62.1 |
| 3-2 | 18 | 528 | 29.3 |
| 3-3 | 46 | 490 | 10.6 |
| 3-4 | 227 | 759 | 3.3 |
| 3-5 | 90 | 294 | 3.3 |
| 3-6 | 189 | 3289 | 17.4 |
| 3-7 | 38 | 136 | 3.6 |
| 3-8 | 6.8 | 4319 | 635.2 |
| 3-9 | 69 | 449 | 6.5 |
| 3-10 | 26 | 21791 | 838.1 |
| 3-11 | 29 | 917 | 31.6 |
| 3-12 | 259 | 756 | 2.9 |
| 3-13 | 47 | 284 | 6.0 |
| 3-14 | 4232 | 27054 | 6.4 |
| 3-15 | 50 | 10825 | 216.5 |
| 3-16 | 17 | 897 | 52.8 |
| 3-17 | 46 | 3475 | 75.5 |
| 3-18 | 6 | 2120 | 353.3 |
| 3-19 | 146 | 1921 | 13.2 |
| 3-20 | 154 | 1678 | 10.9 |
| 3-21 | 76 | 207 | 2.7 |
| 3-22 | 64 | 2737 | 42.8 |
| 3-23 | 22 | 4693 | 213.3 |
| 3-24 | 738 | 934 | 1.3 |
| 3-25 | 86 | 127 | 1.5 |

Preparation of Compounds

General. Column chromatography was carried out by using active silica gel (230-400 mesh) available from Selecto Scientific of Suwanee, Ga. Eluents were distilled before use. Solvents for reactions were dried or purified as required. Reactions were carried out under argon atmosphere unless otherwise noted. All of the reagents are available from Sigma-Aldrich Fine Chemicals of Milwaukee, Wis. and/or Lancaster Synthesis Inc. of Windham, N.H.

Modification of the direct aromatic substitution at pyrazole position 1 can be obtained by varying the respective starting hydrazine (i.e. 2,4-dichlorophenylhydrazine hydrochloride). Typically the starting hydrazine will having the general formula:

Ar—NHNH$_2$

Modification at pyrazole position 3 can be obtained by varying the respective starting material (i.e. 1-aminopiperidine). Typically the starting material will have the general formula:

RNH$_2$

Most of the compounds with substitutions at pyrazole position 5 can be obtained through method A, disclosed below, by varying the starting material (4'-bromopropiophenone shown). Typically the starting material will have the general formula:

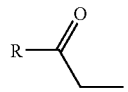

The synthesis of most of the above starting materials is disclosed in the existing literature. See, for example, *Synthesis*, 4, 1999, 588-592. Synthesis of the starting materials not disclosed in the existing literature can be performed by a person skilled in the art using analogous chemistries and with no more than routine experimentation.

General Procedure for the Preparation of Intermediate (Int.) A and Int B:

Method A: Modification at Pyrazole Positions 1, 3 and 5

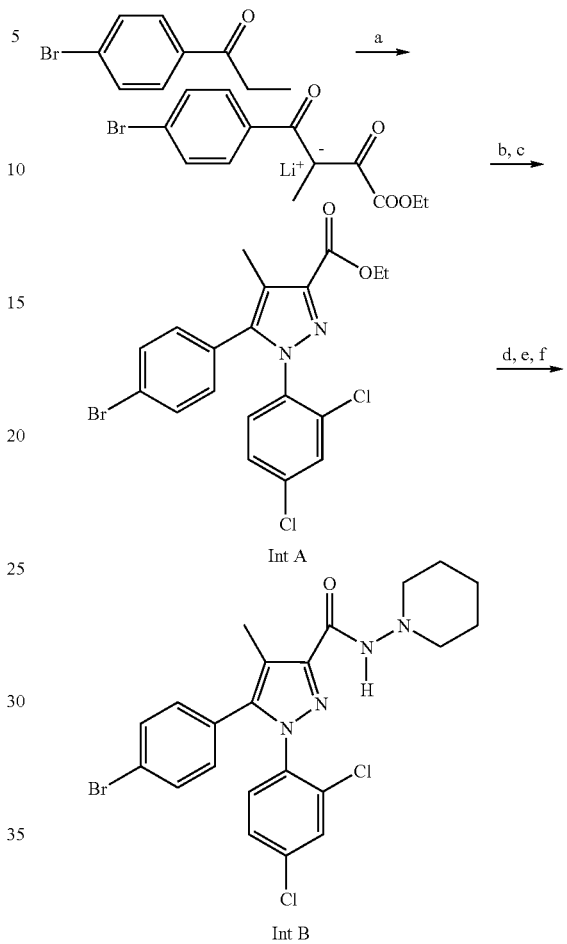

(a) LIHMDS, ether, then EtO$_2$CCO$_2$Et; (b) 2,4-Dichlorophenylhydrazine hydrochloride, EtOH; (c) AcOH; (d) KOH/MeOH, HCl/H$_2$O; (e) SOCl$_2$, toluene; (f) 1-Aminopiperidine, Et$_3$N, CH$_2$Cl$_2$.

Lithium salt of ethyl 2,4-dioxo-3-methyl-4-(4-bromophenyl)butanoate. To a magnetically stirred solution of lithium bis(trimethylsilyl)amide (40 mL, 1.0 M solution in hexane, 40 mmol) in diethyl ether (120 mL) was added a solution of 4'-bromopropiophenone (8.52 g, 40 mmol) in diethyl ether (50 mL) at −78° C. After the mixture was stirred at the same temperature for an additional 45 min, diethyl oxalate (6.4 mL, 47 mmol) was added to the mixture. The reaction mixture was allowed to warm to room temperature (RT) and stirred for 16 h. The precipitate was filtered, washed with diethyl ether, and dried under vacuum to afford the lithium salt.

1-(2,4-Dichlorophenyl)-4-methyl-5-(4-bromophenyl)-1H-pyrazole-3-carboxylic acid, Ethyl Ester (Int. A). To a magnetically stirred solution of the above lithium salt (0.64 g, 2.0 mmol) in 10 mL of ethanol was added 2,4-dichlorophenylhydrazine hydrochloride (0.47 g, 2.2 mmol) at room temperature. The resulting mixture was stirred at room temperature for 20 h. The precipitate was filtered, washed with ethanol and diethyl ether, and then dried under vacuum to give a light yellow solid. This solid was dissolved in acetic acid (7 mL) and heated under reflux for 24 h. The reaction mixture was poured into cold water and extracted multiple times with ethyl acetate. The combined extracts were washed with water, saturated aqueous sodium bicarbonate, and brine, dried over anhydrous sodium sulfate, filtered, and evaporated. Purification by flash column chromatography on silica gel gave the expected ester Int. A.

N-(Piperidin-1-yl)-5-(4-bromophenyl)-1-(2,4-dichlorophenyl)-4-methyl-1H-pyrazole-3-carboxamide (Int. B). To a magnetically stirred solution of ester Int. A (0.625 g, 1.38 mmol) in methanol (7 mL) was added a solution of potassium hydroxide (0.155 g, 2.76 mmol) in methanol (5 mL). The mixture was heated under reflux for 3 h. The cooling reaction mixture was then poured into water (10 mL) and acidified with 10% hydrochloric acid. The precipitate was filtered, washed with water, and dried under vacuum to yield the corresponding acid as a solid.

A solution of the crude acid (0.585 g) and thionyl chloride (0.492 g, 4.14 mmol) in toluene (10 mL) was refluxed for 3 h. Solvent was evaporated under reduced pressure, and the residue was then redissolved in toluene (20 mL) and evaporated to yield the crude carboxylic chloride as a solid. A solution of the above carboxylic chloride (1.24 mmol) in dichloromethane (5 mL) was added dropwise to a solution of 1-aminopiperidine (0.21 mL, 1.92 mmol) in dichloromethane (5 mL) at 0° C. After stirring at RT for 3 h, the reaction mixture was added with brine and extracted multiple times with dichloromethane. The combined extracts were washed with brine, dried over anhydrous sodium sulfate, filtered, and evaporated. Purification by flash column chromatography on silica gel gave the expected amide Int. B.

Method B: Alternate Route for 5-Substituted Analogs

Some of the 5-substituted analogs can be prepared from Int. B via a Suzuki coupling reaction. The Suzuki coupling reaction allows synthesis of novel compounds in which the 5-phenyl ring is substituted with an aromatic ring or a heteroaromatic ring.

The coupling of a saturated heterocyclic ring (for example, morpholine) on the 5-phenyl ring can be obtained by Pd-catalyzed amination reaction (*J. Org. Chem.* 2000, 65, 1144-1157).

General Procedure for the Suzuki Coupling Reaction:

To a degassed solution of Int. B (100 mg, 0.197 mmol) and Pd (PPh$_3$)$_4$ (0.0085 mmol, 5 mol%) in 2 mL of DME was added 0.218 mmol of diethyl (3-pyridyl) borane or other aromatic boranic acid followed by 0.22 mmol of Na$_2$CO$_3$ in 1 mL of water. The resulting mixture was refluxed overnight. After reflux the mixture was diluted with CH$_2$Cl$_2$ and water. The organic phase was separated, and the water layer was extracted with CH$_2$Cl$_2$. The combined organic layer was washed with brine, dried over anhydrous sodium sulfate, filtered, and evaporated. Purification by flash column chromatography on silica gel gave the expected product.

Method C: Modification at Pyrazole Position 4

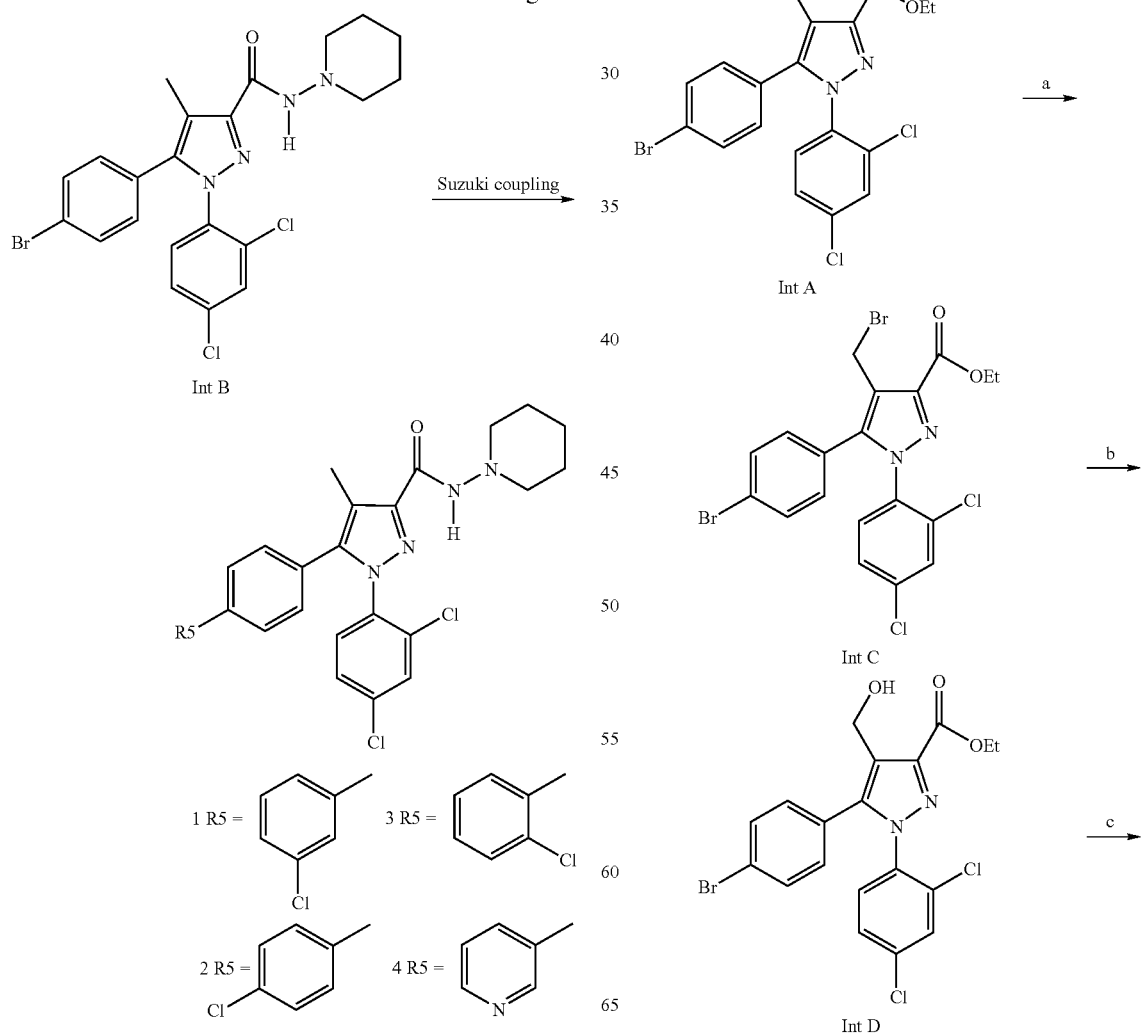

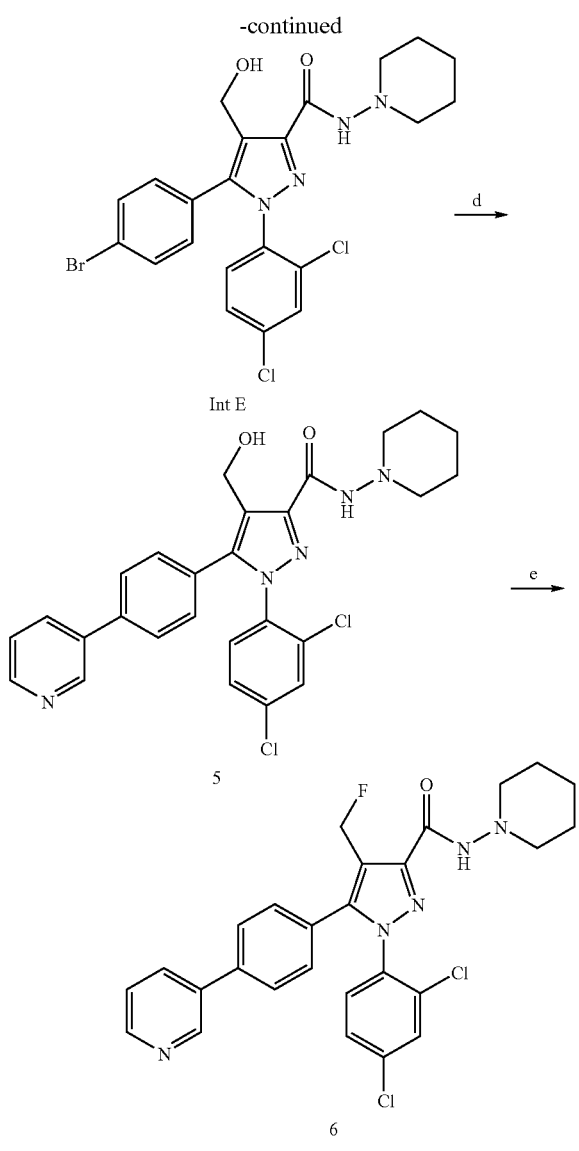

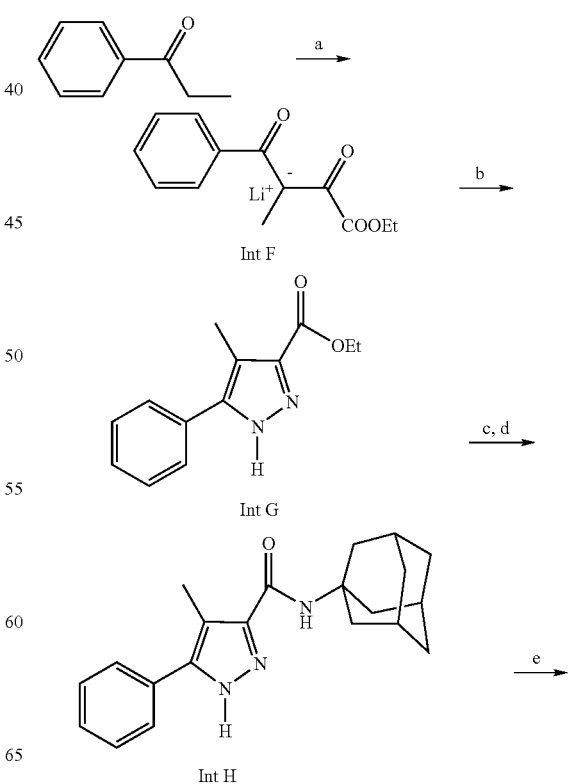

(a) NBS, AIBN, CCl₄; (b) AgNO₃, aq. acetone; (c) AlCl₃, 1-aminopiperidine, 1,2-dichloroethane; (d) Pd(PPh₃)₄, diethyl (3-pyridyl) borane, DME, aq. NaCO₃; (e) DAST, CH₂Cl₂

These are obtained by functionalizing the 4-methyl group of the parent compound (Int. A). A variety of novel compounds having different substituents at pyrazole position 4 can be obtained. Similarly, modifications at pyrazole positions 3 and 5 can be obtained as shown under Method C.

Int. C. To a magnetically stirred solution of Int. A (2.02 g, 4.44 mmol) in carbon tetrachloride (30 mL) was added N-bromosuccinimide (0.87 g, 4.89 mmol) and 2,2'-azobisisobutyronitrile (AIBN, 10 mg). The resulting mixture was refluxed for 3 h. After cooling to RT, the precipitate was filtered. The solvent was removed from the filtrate under reduced pressure to give the title product.

Int. D. To a magnetically stirred solution of silver nitrate (2.65 g, 15.6 mmol) in 100 mL of 50% aqueous acetone at RT was added a suspension of Int. C (2.36 g, 4.43 mmol) in 70% aqueous acetone. The mixture was stirred at 60° C. overnight. After cooling to RT, the insoluble material was filtered off and the filtrate was concentrated under vacuum to evaporate acetone. The residue was extracted with CH₂Cl₂. The organic layer was washed twice with water, dried over anhydrous sodium sulfate. The solvent was removed under reduced pressure. Purification by flash column chromatography on silica gel gave the title product.

Int. E. To a magnetically stirred suspension of AlCl₃ (1.16 g, 8.62 mmol) in 1,2-dichloroethane (20 mL) in an ice bath was added 1-aminopiperidine (2.0 mL, 18.0 mmol) in 1,2-dichloroethane (5 mL). The suspension was allowed to warm to RT. The solution of Int. D (2.03 g, 4.43 mmol) in 1,2-dichloroethane (5 mL) was added into the above suspension and the mixture was stirred at RT for 2 h before quenching with a mixture of ice and H₂O. The mixture was stirred for a further 0.5 h and the resulting suspension was filtered through Celite and the organic phase separated. The aqueous phase was extracted multiple times with CH₂Cl₂ and the organic phases combined, washed with H₂O, brine, dried over anhydrous Na₂SO₄. The solvent was removed under reduced pressure. Purification by flash column chromatography on silica gel gave the title product.

Compound 1-5. Compound 1-5 was obtained from Int. E using a Suzuki coupling reaction as described above.

Compound 1-6. To a magnetically stirred solution of compound 1-5 (30 mg, 0.057 mmol) in 1.5 mL of CH₂Cl₂ at 0° C. was added DAST. After 1 h, the reaction mixture was poured into saturated NaHCO₃ (2 mL) and was extracted with CH₂Cl₂. The organic phases combined, washed with H₂O, brine, dried over anhydrous Na₂SO₄. The solvent was removed under reduced pressure. Purification by flash column chromatography on silica gel gave the title product.

An alternate method for obtaining analogs with 1-alkyl substituents is described under Method D.

Method D: Modification at Pyrazole Position 1

-continued

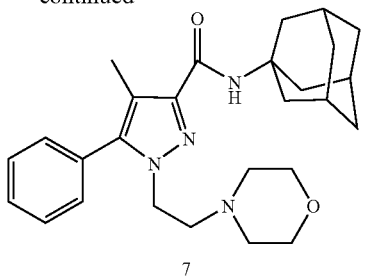

7

(a) LiHMDS, ether, then EtO$_2$CCO$_2$Et; (b) Hydrazine hydrochloride, EtOH; (c) KOH/MeOH; HCl/H$_2$O (d) CO(imid)$_2$/DMF, 1-adamantanamine; (e) NaH/DMF, 4-(2-chloroethyl)morpholine.

Int. F. To a magnetically stirred solution of lithium bis(trimethylsilyl)amide (40 mL, 1.0 M solution in hexane, 40 mmol) in diethyl ether (120 mL) was added a solution of propiophenone (5.30 g, 40 mmol) in diethyl ether (50 mL) at −78° C. After the mixture was stirred at the same temperature for additional 45 min, diethyl oxalate (6.4 mL, 47 mmol) was added to the mixture. The reaction mixture was allowed to warm to room temperature (RT) and stirred for 16 h. The precipitate was filtered, washed with diethyl ether, and dried under vacuum to afford the lithium salt (Int. F).

Int. G To a magnetically stirred solution of the above lithium salt (7.58 g, 32 mmol) in 250 mL of ethanol was added hydrazine hydrochloride (2.4 g, 35 mmol) at room temperature. The resulting mixture was stirred at room temperature for 20 h. After stirring the solvent was removed under reduced pressure and the mixture was added with brine and extracted multiple times with dichloromethane. The combined extracts were washed with brine, dried over anhydrous sodium sulfate, filtered, and evaporated. Purification by flash column chromatography on silica gel gave the expected ester (Int. G).

Int. H To a magnetically stirred solution of ester Int. G (5.88 g, 26 mmol) in methanol (150 mL) was added 10% aqueous potassium hydroxide (36 mL, 64 mmol). The resulting mixture was heated under reflux for 3 h. The cooling reaction mixture was then poured into water and acidified with 10% hydrochloric acid. The precipitate was filtered, washed with water, and dried under vacuum to yield the corresponding acid as a solid.

To a magnetically stirred solution of the above acid (4.02 g, 16 mmol) in 45 mL of DMF was added 1,1'-carbonyidiimidazole (2.8 g, 17 mmol) in one portion at RT and the mixture was stirred at 60° C. for 3 hrs. To the above mixture was added a mixture of 1-adamantanamine (2.6 g, 17 mmol) in 45 mL of DMF. The resulting mixture was heated at 60° C. overnight. DMF was removed under reduced pressure. Ethyl acetate was added to the residue, and the mixture was filtered to collect the solid.

Compound 1-7. To a magnetically stirred solution of Int. H (188 mg, 0.56 mmol) in 4 mL of DMF, was added NaH (60% dispersion in mineral oil, 35 mg, 0.87 mmol) at 0° C. and the mixture was stirred at RT for 3 hrs. After stirring, the reaction mixture was cooled to 0° C. and a solution of 4-(2-chloroethyl)morpholine (185 mg, 1.25 mmol) in 1 mL of DMF was added. The resulting mixture was heated at 60° C. for 3 hrs. After heating, brine was added to the mixture, which was subsequently extracted multiple times with dichloromethane. The combined extracts were washed with brine, dried over anhydrous sodium sulfate, filtered, and evaporated. Purification by flash column chromatography on silica gel gave the expected product.

Method E: Modification at Pyrazole position 5

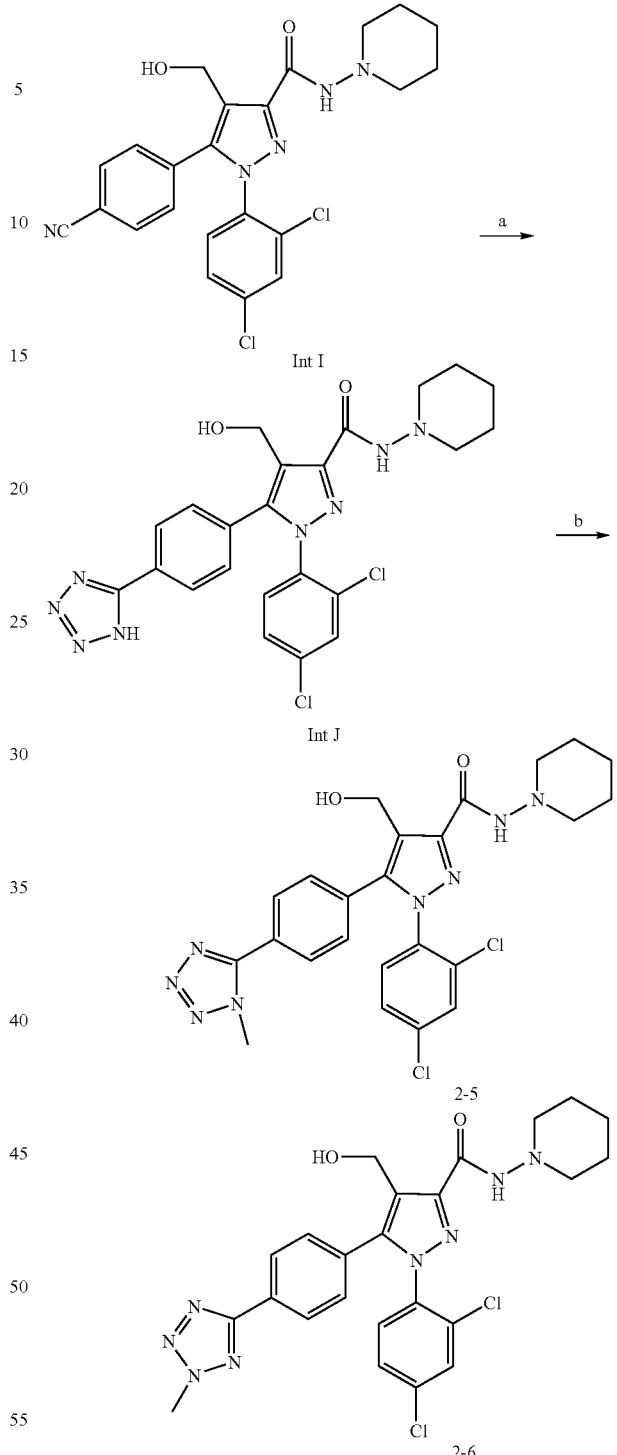

(a) NaN$_3$, Et$_3$N•HCl, toulene;
(b) CH$_3$I, K$_2$CO$_3$, CH$_3$CN

Int. J. The mixture of Int I (1.50 g, 3.19 mmol), NaN$_3$ (0.65 g, 10 mmol) and Et$_3$N.HCl (1.37 g, 10 mmol) in toluene (25 mL) was heated to 70° C. for 12 h with stirring. After cooling, the product was extracted with water. The aqueous layer, 36% HCl was added dropwise to salt out the title product. After filtration, the solid was dried under reduced pressure. (see Synthesis, 6, 1998, 910).

Compounds 2-5 and 2-6. To the Int J (0.51 g, 1 mmol) in CH$_3$CN (10 mL) K$_2$CO$_3$ (0.13 g, 1 mmol) was added. To this CH₃I (0.12 ml, 2 mmol) was added. The contents were stirred at room temperature for 4-5 hrs. The reaction was quenched with water and extracted with ethyl acetate. The organic layer was separated and dried over anhydrous MgSO₄. The solvent was removed under reduced pressure. Two isomers 2-5 and 2-6 were separated and purified by flash column chromatography on silica gel.

Method F: Modification at Pyrazole position 3

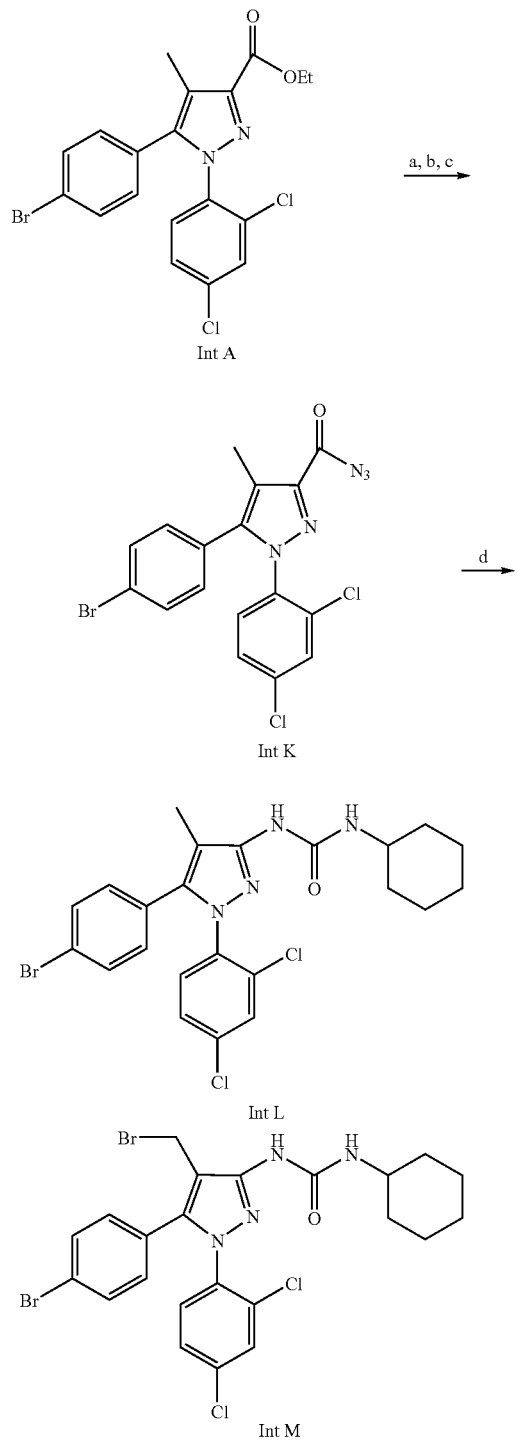

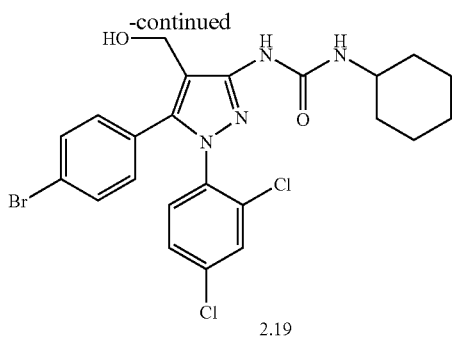

(a) KOH/MeOH, HCl/H₂O;
(b) SOCl₂, toulene;
(c) aq. NaN₃, THF;
(d) cyclohexylamine, toulene;
(e) NBS, AIBN, CCl₄;
(f) DMSO/H₂O Int. K. To a magnetically stirred solution of ester Int. A (0.625 g, 1.38 mmol) in methanol (7 mL) was added a solution of potassium hydroxide (0.155 g, 2.76 mmol) in methanol (5 mL). The mixture was heated under reflux for 3 h. The cooling reaction mixture was then poured into water (10 mL) and acidified with 10% hydrochloric acid. The precipitate was filtered, washed with water, and dried under vacuum to yield the corresponding acid as a solid.

A solution of the crude acid (0.585 g) and thionyl chloride (0.492 g, 4.14 mmol) in toluene (10 mL) was refluxed for 3 h. Solvent was evaporated under reduced pressure, and the residue was then redissolved in toluene (20 mL) and evaporated to yield the crude carboxylic chloride as a solid. To the solution of above carboxylic chloride (1.24 mmol) in THF (5 mL), NaN₃ (0.081 g, 1.24 mmol) in 0.5 mL of water was added at 0° C. The contents were stirred at that temperature for 1 hr. The reaction was quenched with water (5 mL), both aqueous and organic layers were separated. The organic layer was extracted using ethyl acetate (10 mL) and dried over anhydrous MgSO₄. The solvent was evaporated under reduced pressure to give the title product.

Int. L. To a magnetically stirred solution of Int. K (0.448 g, 1 mmol) in toluene (10 mL) cyclohexyl amine (0.34 mL, 3 mmol) was added. The contents were stirred at 100° C. for 8 h. After cooling to room temperature the reaction was quenched by water (5 mL). Both aqueous and organic layers were separated, the organic layer was dried over anhydrous MgSO₄. The solvent was evaporated under reduced pressure. Purification by flash chromatography on silica gel gave the title product.

Int. M. To a magnetically stirred solution of Int. L (0.522 g, 1 mmol) in carbon tetrachloride (20 mL) was added N-bromosuccinimide (0.21 g, 1.2 mmol) and 2,2'-azobisisobutyronitrile (AIBN, 5 mg). The resulting mixture was refluxed for 3 h. After cooling to RT, the precipitate was filtered. The solvent was removed from the filtrate under reduced pressure to give the title product.

Compound 2-19. To the Int. M (0.601 g, 1 mmol), DMSO/H₂O (5:1) were added. The mixture was stirred at 60° C. for 5 h. After cooling to RT, water (30 mL) was added. The organic layer was extracted with ethyl acetate and dried over anhydrous MgSO₄. The solvent was removed under reduced pressure. Purification by flash column chromatography on silica gel gave the title product.

11 rats were trained to press a lever five times to receive a 45 mg food pellet. The training continued over a time period of several weeks. After the training period all rats received drug treatments once per week. The specific rat receiving a drug treatment and the dosage given were each randomly varied. The treatments comprised administration of a vehicle control solution or various dosages of inventive compound 1-5 in combination with the vehicle control solution. All injections were given IP. Ten minutes after injection the rat was placed in proximity to the lever.

FIG. 1 illustrates a mean (±SEM) number of lever presses in 30 min for treated animals. The overall suppression of food-reinforced lever pressing was statistically significant ($p<0.05$). FIG. 1 illustrates a classic dose response curve wherein as the dose of drug (inventive compound 1-5) increases, lever pressing consistently decreases. Without wishing to be bound to any theory, applicants believe that inventive compound 1-5 antagonizes (blocks) the CB1 receptors, thereby suppressing appetite and leading to decreased lever pressing.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A compound of formula I below, and physiologically acceptable salts thereof, comprising:

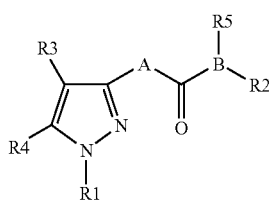

I wherein:
A is a direct bond;
B is N;
R1 is -Z;
   Z is an aromatic ring having about 5 to about 7 ring members or an aromatic ring having about 5 to about 7 ring members substituted on at least one available ring atom by an alkyl group; and wherein the connecting point between the —$(CH_2)_n$— group and the Z group can be any available ring carbon atom; or
   Z is a 6 member aromatic ring or a substituted 6 member aromatic ring; and wherein the connecting point between the —$(CH_2)_n$— group and the Z group can be any available ring carbon atom; or
   Z is

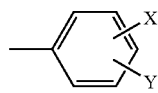

wherein X and Y are each independently selected from H, halogen, $N_3$, NCS, ON, $NO_2$, $NX_1X_2$, $OX_3$, OAc, O-acyl, O-aroyl, NH-acyl, NH-aroyl, CHO, $CF_3$, $COOX_3$, $SO_3H$, $SO_2NX_1X_2$, $CONX_1X_2$, alkoxy, alkylmercapto, alkylamino, dialkylamino, alkylsulfinyl, alkylsulfonyl or (when Z is a structure having two adjacent carbon atoms methylene dioxy,
   $X_1$ and $X_2$ are each independently selected from H or alkyl, or
   $X_1$ and $X_2$ together are part of a heterocyclic ring having about 4 to about 7 ring members and optionally one additional heteroatom selected from O, N or S, or
   $X_1$ and $X_2$ together are part of an imide ring having about 5 to about 6 members,
   $X_3$ is selected from H, alkyl, hydroxyloweralkyl or alkyl-$NX_1X_2$,
   $X_4$ is selected from H or alkyl;
R2 is selected from a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring or a heteropolycyclic ring; or
R2 is

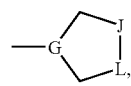

wherein G is selected from OH or N, and L and J are each independently selected from $(CH_2)_n$, O, NH or S, n is an integer from 0 to about 7; or
R2 is

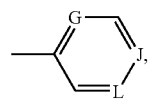

wherein G, L and J are each independently selected from OH or N; or
R2 is selected from

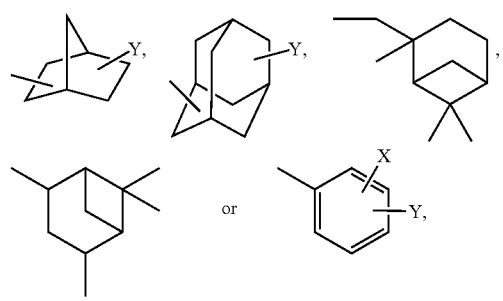

wherein X and Y are each independently selected from H, halogen, $N_3$, NCS, Ph (phenyl), CN, $NO_2$, $NX_1X_2$, $OX_3$, OAc, O-acyl, O-aroyl, NH-acyl, NH-aroyl, CHO, $CF_3$, $COOX_3$, $SO_3H$, $SO_2NX_1X_2$, $CONX_1X_2$, alkyl, alcohol, alkoxy, alkylmercapto, alkylamino, dialkylamino, alkylsulfinyl or alkylsulfonyl,
   $X_1$, and $X_2$ are each independently selected from H or alkyl, or
   $X_1$, and $X_2$ together are part of a heterocyclic ring having about 4 to about 7 ring members and optionally a second heteroatom selected from O, N or S, or
   $X_1$, and $X_2$ together are part of an imide ring having about 5 to about 6 members, X₃ is selected from H, alkyl, hydroxyloweralkyl or alkyl-NX₁X₂; or R2 is selected from a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms;

R3 is CN, CH₃ or CH₂OH;

R4 is -Phenyl-Z,

Z is selected from an aromatic ring having about 5 to about 7 ring members, a heteroaromatic ring having about 5 to about 7 ring members, an aromatic bicyclic ring, an aromatic heterobicyclic ring, an aromatic polycyclic ring, an aromatic heteropolycyclic ring; or any above group substituted on at least one available ring atom by an alkyl group; and wherein the connecting point between the —(CH₂)ₙ— group and the Z group can be any available ring carbon atom or any available ring nitrogen atom; or Z is selected from

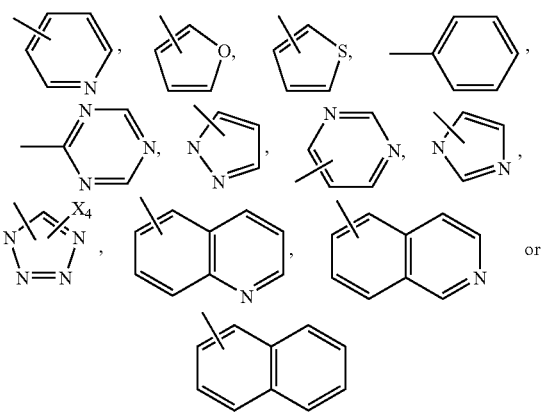

wherein X₄ is selected from H or alkyl; and

R5 is H or alkyl;

with the provisos that:

when A is a direct bond and B is N then R1 cannot be H;

when A is a direct bond and B is N and R5 is hydrogen and R2 has a nitrogen directly connected to the nitrogen of the amide at the 3-position of pyrazole ring, then R4 can not be a phenyl ring or a phenyl ring having one to three substitutions selected from halogen, trifluoromethyl, 1-pyrrolidinyl, 1-piperidinyl, 4-morpholinyl, 1-piperazinyl, lower-alkyl substituted 1-pyrrolidinyl, lower-alkyl substituted 1-piperidinyl, lower-alkyl substituted 4-morpholinyl, and lower-alkyl substituted 1-piperazinyl.

2. The compound of claim 1 wherein R4 is -Phenyl-Z and Z is selected from a heteroaromatic ring having about 5 to about 7 ring members, an aromatic heterobicyclic ring, an aromatic heteropolycyclic ring; or any above group substituted on at least one available ring atom by an alkyl group; and wherein the connecting point between the Phenyl group and the Z group can be any available ring carbon atom or any available ring nitrogen atom.

3. The compound of claim 1 wherein R4 is -Phenyl-Z, Z is selected from

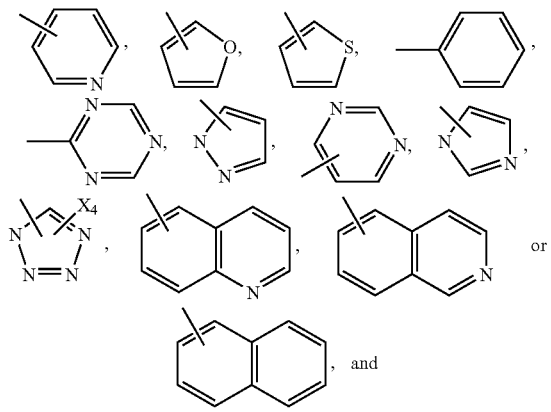

x₄ is H or alkyl.

4. The compound of claim 1 wherein R1 is -Z, and Z is a 6 member aromatic ring or a substituted 6 member aromatic ring; and wherein the connecting point between the —(CH₂)ₙ— group and the Z group can be any available ring carbon atom.

5. The compound of claim 1 wherein R1 is

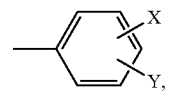

wherein X and Y are each independently selected from H, halogen, N₃, NCS, CN, NO₂, NX₁X₂, OX₃, OAc, O-acyl, O-aroyl, NH-acyl, NH-aroyl, CHO, CF₃, COOX₃, SO₃H, SO₂NX₁X₂, CONX₁X₂, alkoxy, alkyl mercapto, alkylamino, di-alkylamino alkylsulfinyl, alkylsulfonyl or (when Z is a structure having two adjacent carbon atoms methylene dioxy, X₁, and X₂ are each independently selected from H or alkyl, or X₁ and X₂ together are part of a heterocyclic ring having about 4 to about 7 ring members and optionally one additional heteroatom selected from O, N or S, or X₁ and X₂ together are part of an imide ring having about 5 to about 6 members, X₃ is selected from H, alkyl, hydroxyloweralkyl or alkyl-NX₁X₂, and X₄ is selected from H or alkyl.

6. The compound of claim 1 wherein R2 is selected from a carbocyclic ring having about 4 to about 7 members, a heterocyclic ring having about 4 to about 7 members, an aromatic ring having about 5 to about 7 ring members, a heteroaromatic ring having about 5 to about 7 members, a bicyclic ring, a heterobicyclic ring, a tricyclic ring, a heterotricyclic ring, a polycyclic ring or a heteropolycyclic ring.

7. The compound of claim 1 wherein R2 is

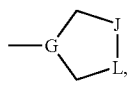

and G is selected from CH or N, and L and J are each independently selected from (CH$_2$)$_n$, O, NH or S, n is an integer from 0 to about 7.

8. The compound of claim 1 wherein R2 is

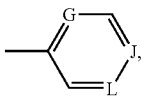

and G, L and J are each independently selected from CH or N.

9. The compound of claim 1 wherein R2 is selected from

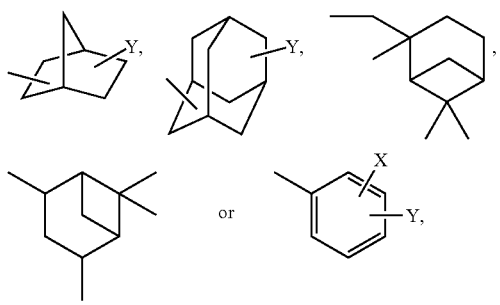

and

X and Y are each independently selected from H, halogen, N$_3$, NCS, Ph (phenyl), CN, NO$_2$, NX$_1$X$_2$, OX$_3$, OAc, O-acyl, O-aroyl, NH-acyl, NH-aroyl, CHO, CF$_3$, $_{COOX3}$, SO$_3$H, SO$_2$NX$_1$X$_2$, CONX$_1$X$_2$, alkyl, alcohol, alkoxy, alkylmercapto, alkylamino, di-alkylamino, alkylsulfinyl or alkylsulfonyl, X$_1$ and X$_2$ are each independently selected from H or alkyl, or X$_1$, and X$_2$ together are part of a heterocyclic ring having about 4 to about 7 ring members and optionally a second heteroatom selected from O, N or S, or X$_1$ and X$_2$ together are part of an imide ring having about 5 to about 6 members, X$_3$ is selected from H, alkyl, hydroxyloweralkyl or alkyl-NX$_1$X$_2$.

10. The compound of claim 1 wherein R2 is selected from a carbocyclic ring having 6 ring atoms fused to a heterocyclic ring having from 5 to 7 ring atoms, a carbocyclic ring having 6 ring atoms fused to a heteroaromatic ring having from 5 to 7 ring atoms, a heterocyclic ring having 6 ring atoms fused to a heterocyclic ring having from 5 to 7 ring atoms, an heterocyclic ring having 6 ring atoms fused to a heteroaromatic ring having from 5 to 7 ring atoms, an aromatic ring having 6 ring atoms fused to a heterocyclic ring having from 5 to 7 ring atoms, an aromatic ring having 6 ring atoms fused to a heteroaromatic ring having from 5 to 7 ring atoms, a heteroaromatic ring having 6 ring atoms fused to a heterocyclic ring having from 5 to 7 ring atoms or a heteroaromatic ring having 6 ring atoms fused to a heteroaromatic ring having from 5 to 7 ring atoms.

11. The compound of claim 1, and physiologically acceptable salts thereof, selected from one of the following structures:

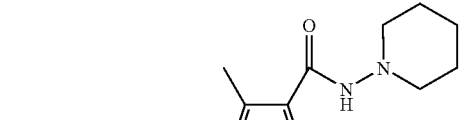

1-4

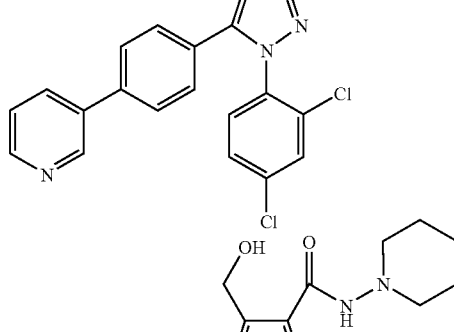

1-5

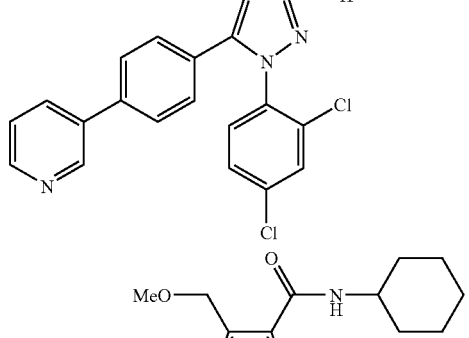

1-17

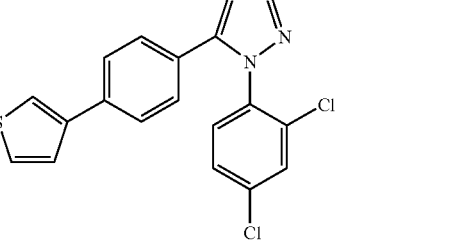

1-18

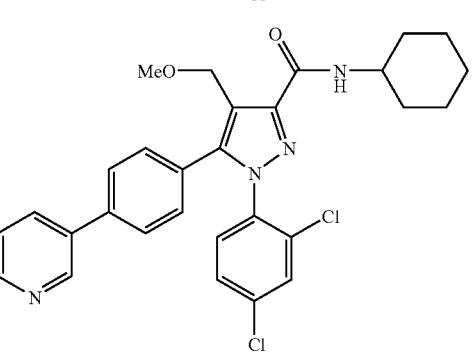

1-19

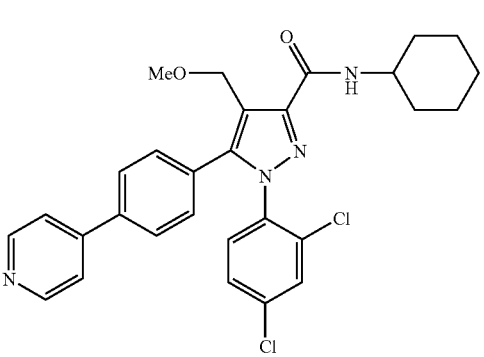

-continued
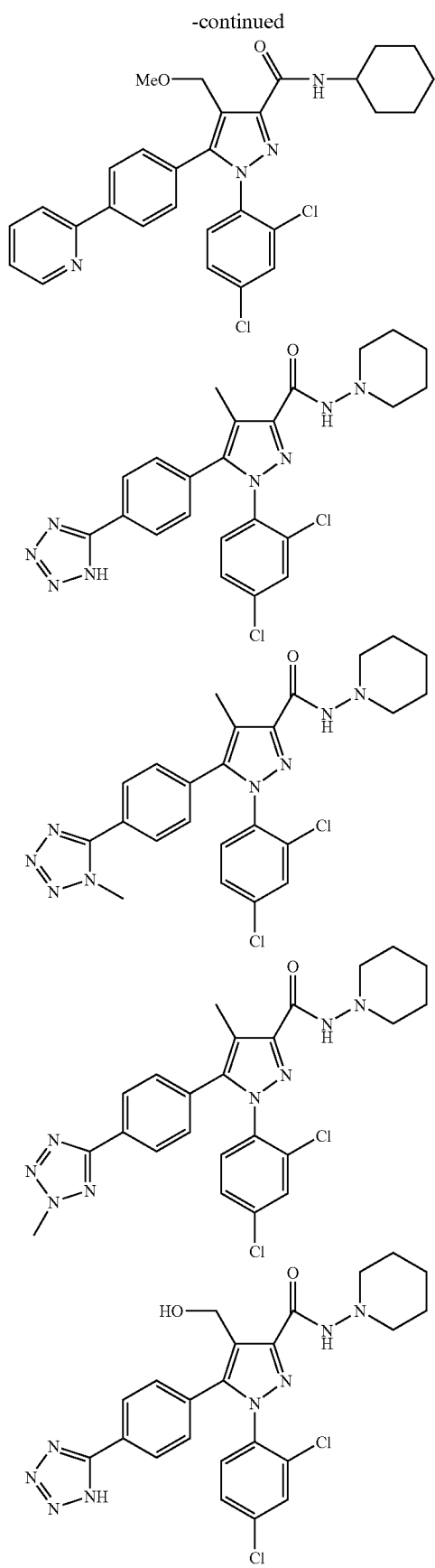
-continued
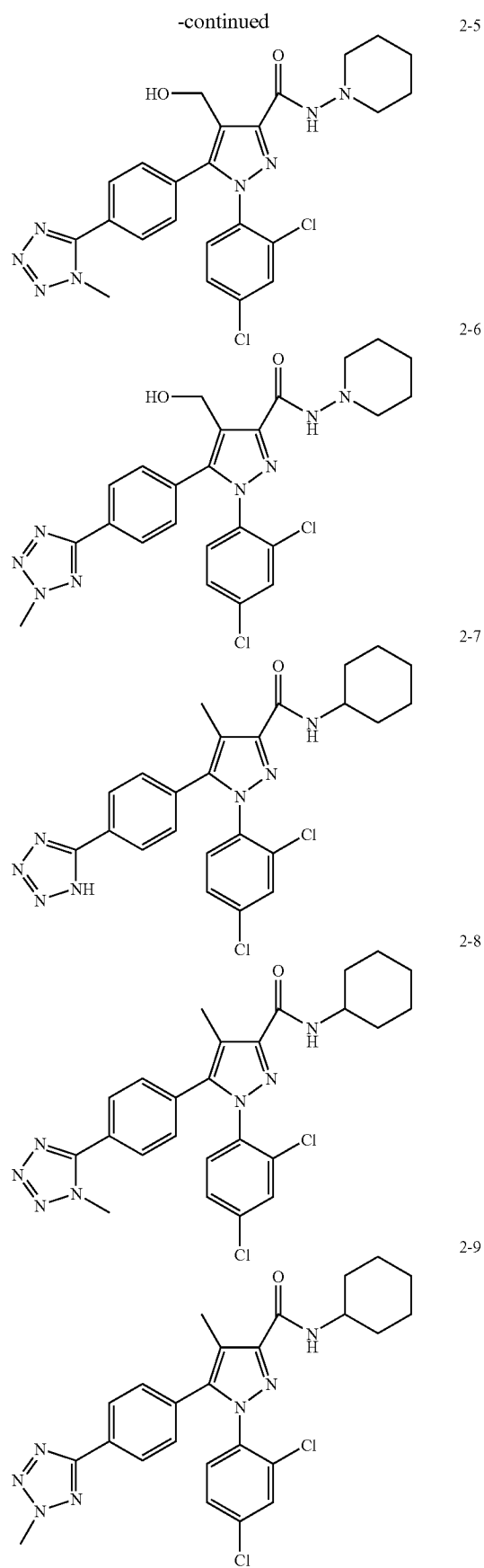

-continued
2-10
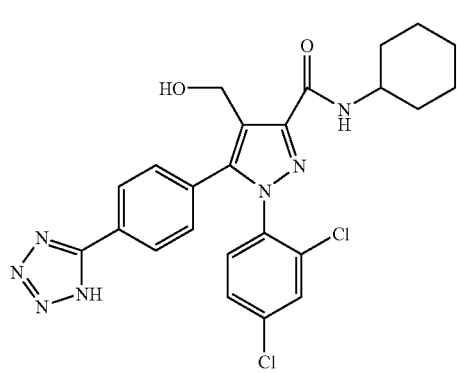
2-11
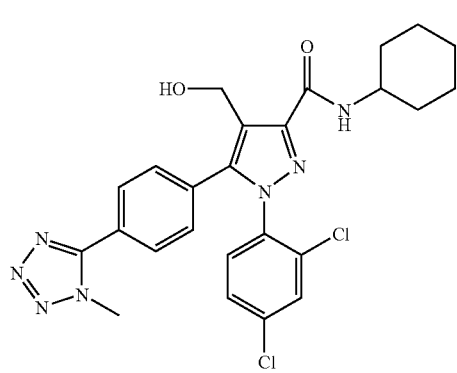
2-12
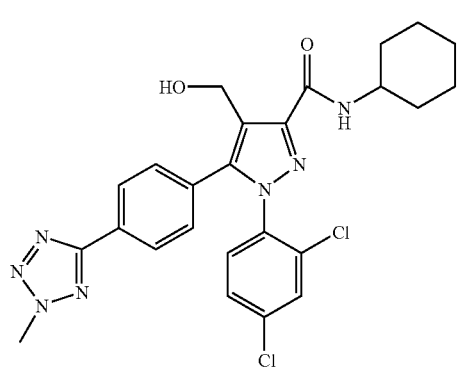
2-13
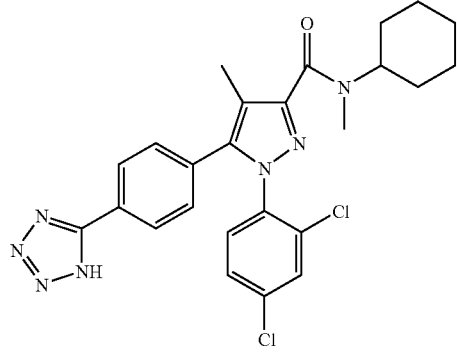
-continued
2-14
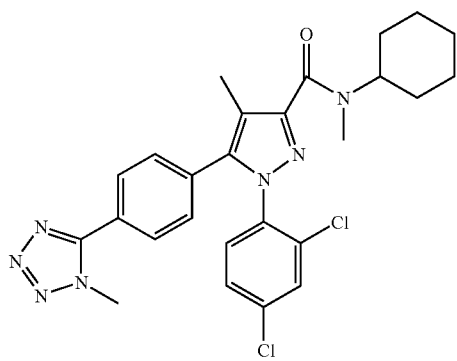
2-15
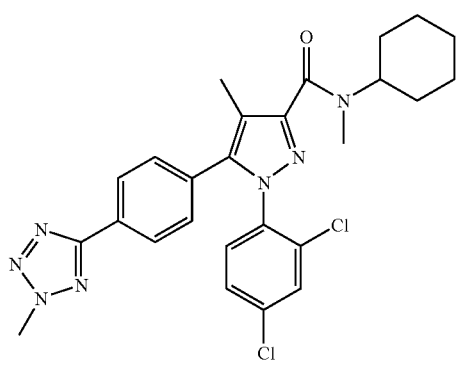
2-16
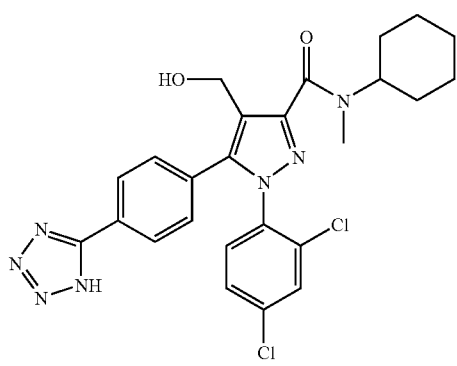
2-17
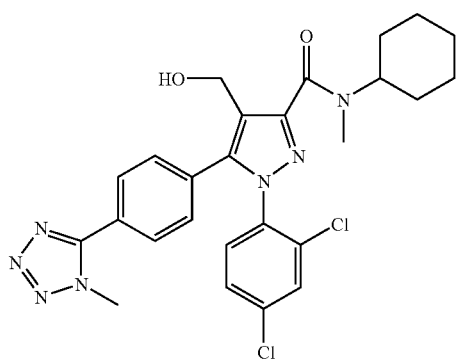

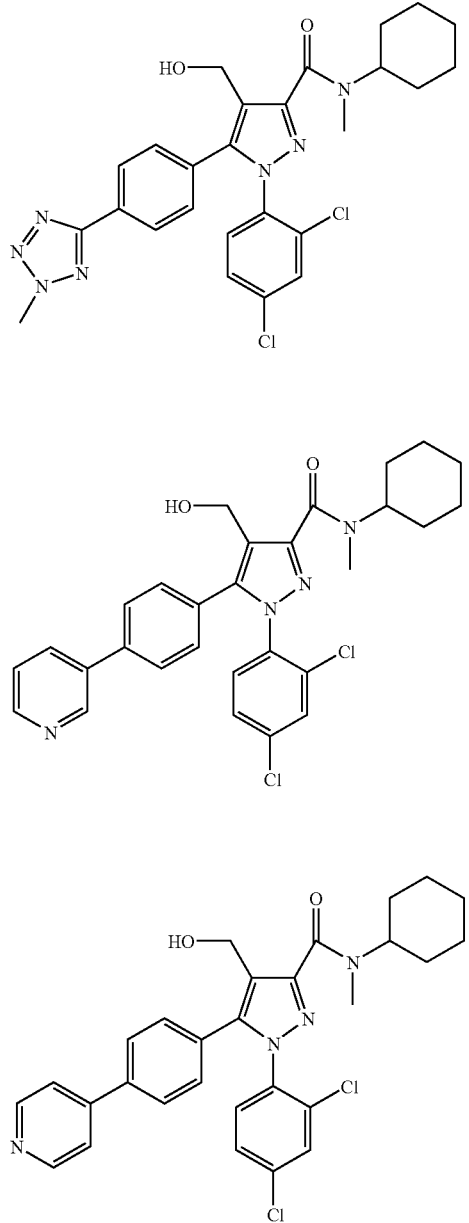
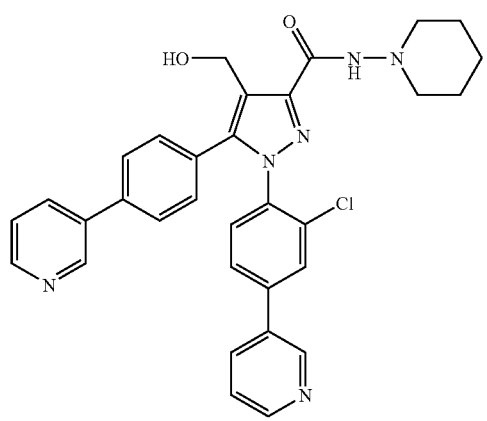
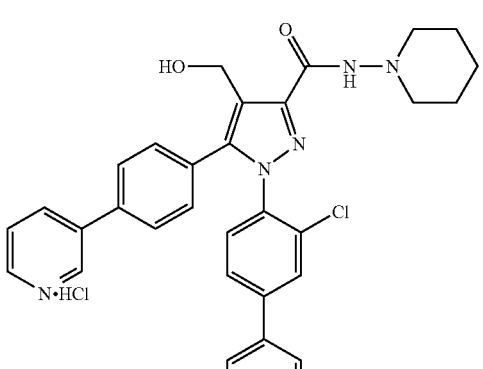
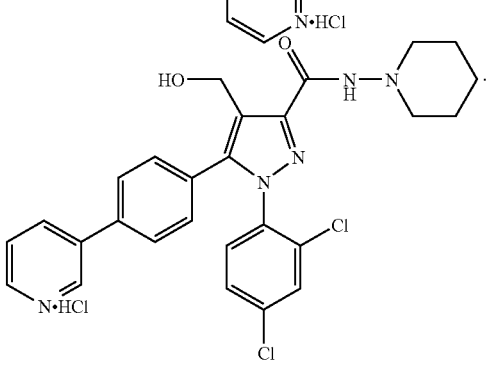
12. The compound of claim 1, and physiologically acceptable salts thereof, selected from one of the following structures:
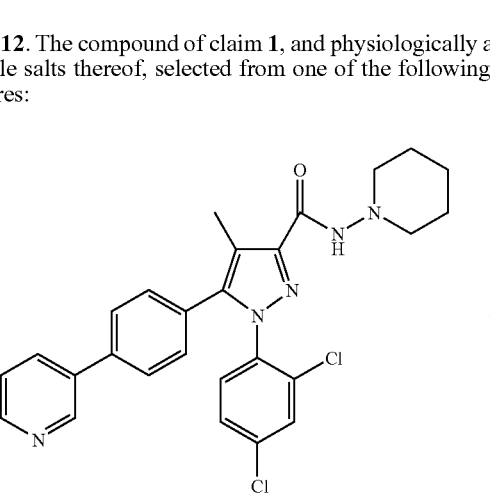

-continued
1-5
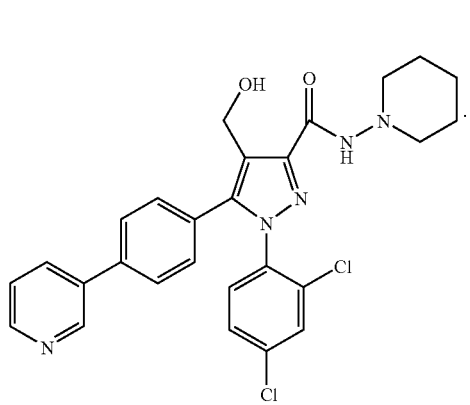
13. The compound of claim 1, and physiologically acceptable salts thereof, selected from one of the following structures:
2-1
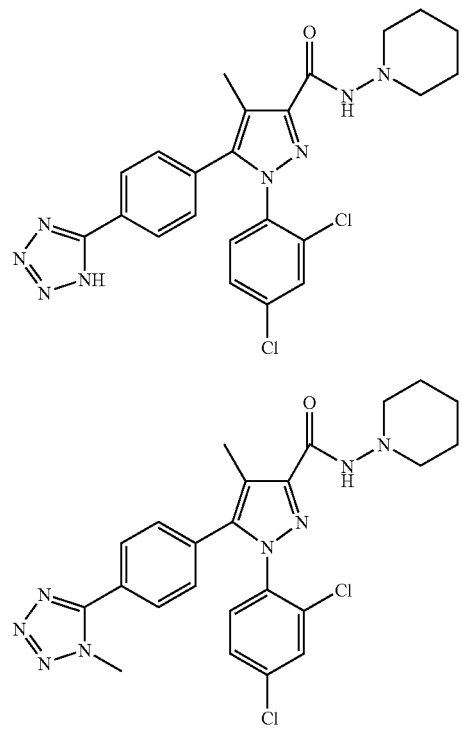
2-2
2-3
-continued
2-4
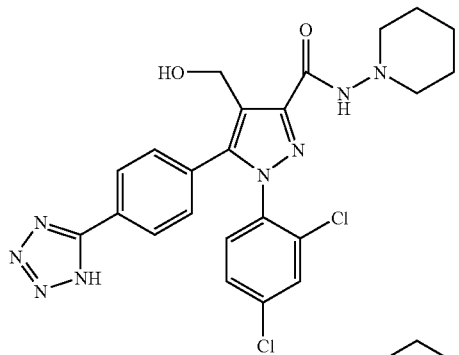
2-5
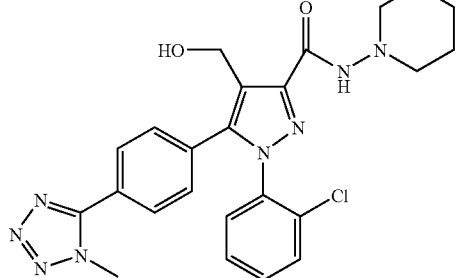
2-6
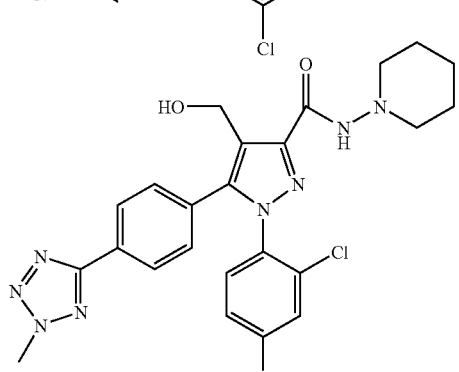
2-7
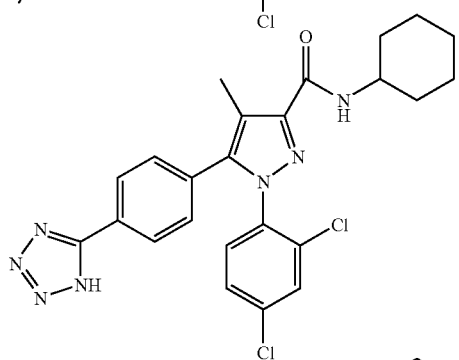
2-8
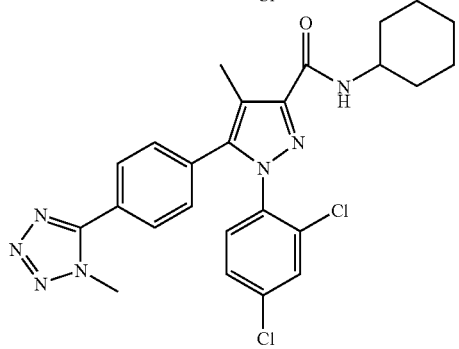

-continued
2-9
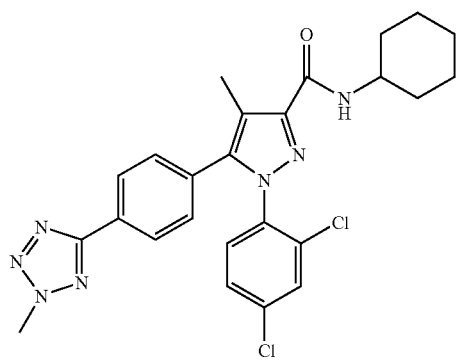
2-10
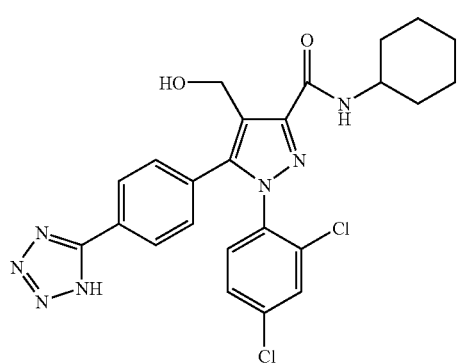
2-11
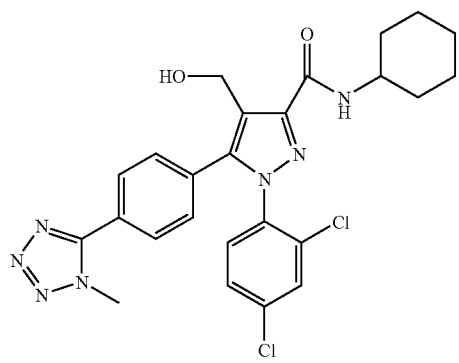
2-12
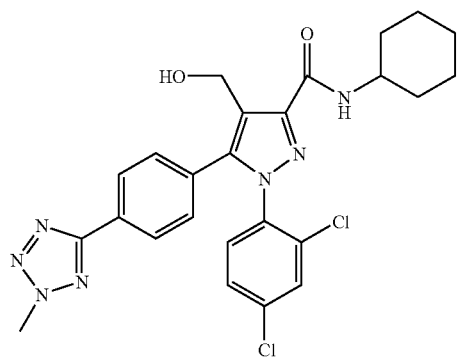
-continued
2-13
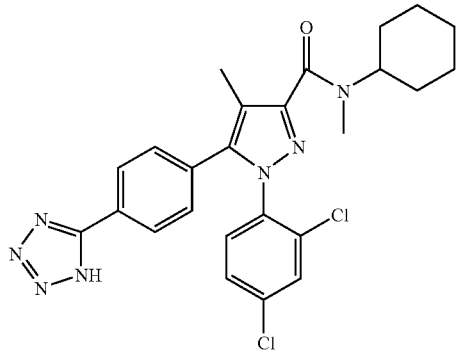
2-14
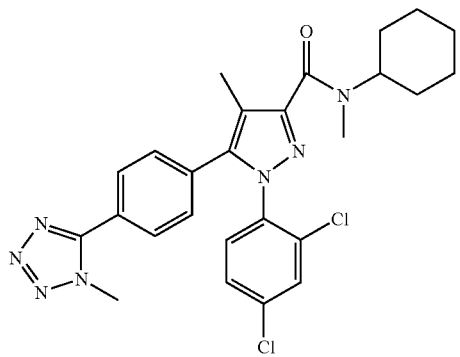
2-15
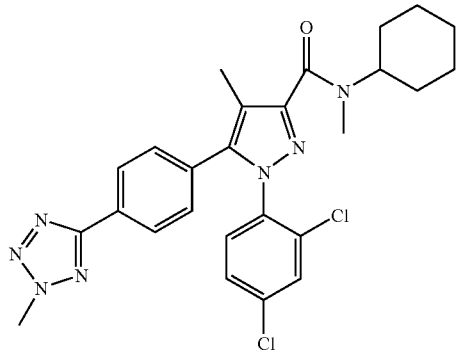
2-16
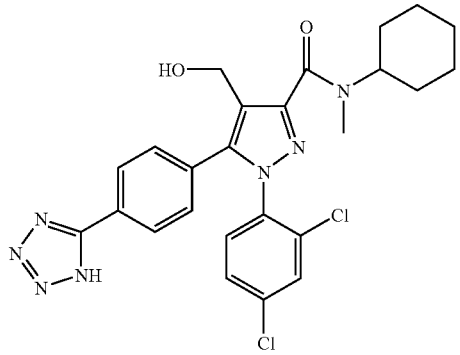

2-17
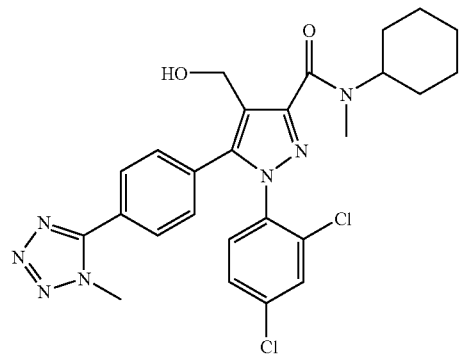
or
2-18
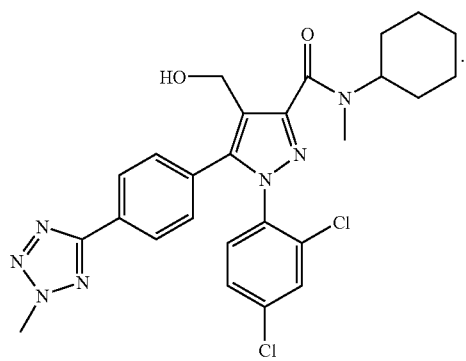
14. The compound of claim 1, and physiologically acceptable salts thereof, selected from one of the following structures:
3-4
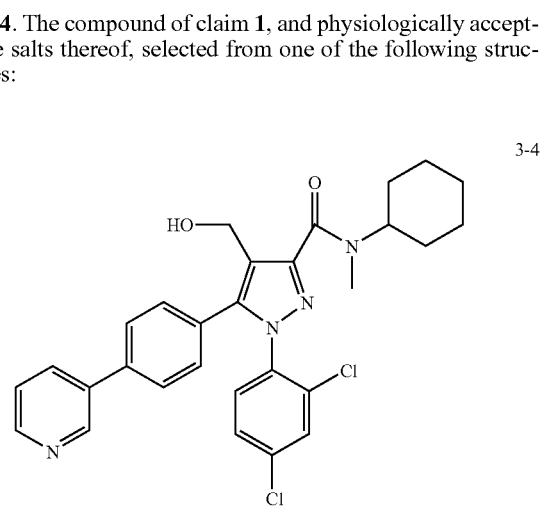
3-5
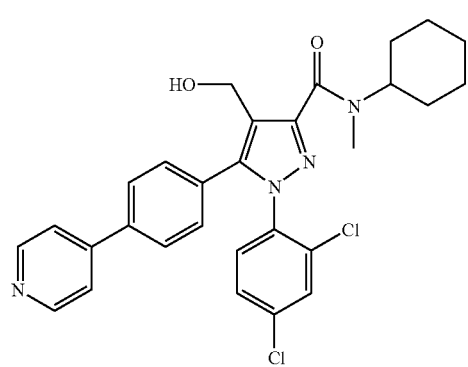
3-6
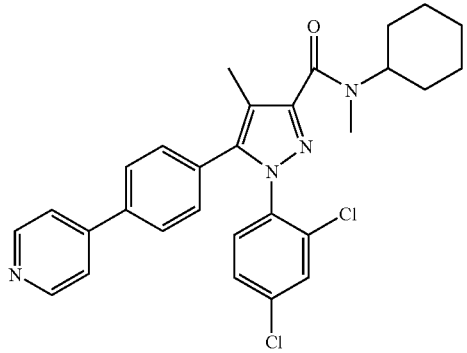
3-19
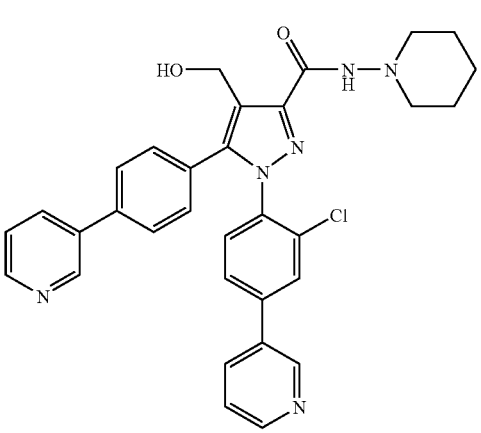
3-20
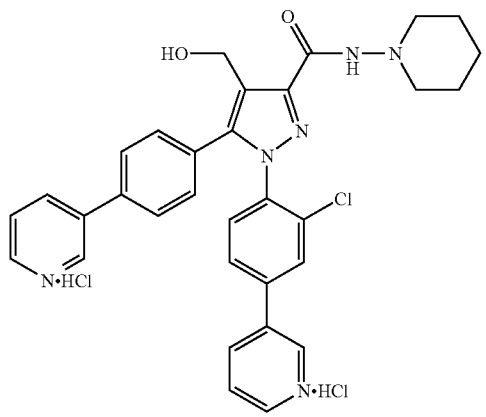
or
3-21
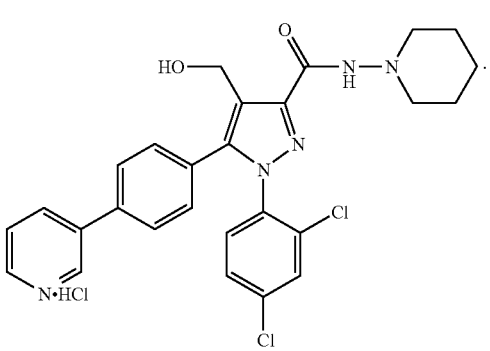

15. The compound of claim 1, and physiologically acceptable salts thereof, wherein R4 is a phenyl ring linked to a terminal aromatic ring having 5 ring members and 4 nitrogen atoms as ring members.

16. The compound of claim 1 wherein:
A is a direct bond;
B is N;
R1 is a phenyl ring substituted with 0 to 3 halogen atoms;
R2 is piperidine; and
R4 is -Phenyl-Z,
   Z is a heteroaromatic ring having about 5 to about 7 ring members, an aromatic heterobicyclic ring, an aromatic heteropolycyclic ring; or any above group substituted on at least one available ring atom by an alkyl group; and wherein the connecting point between the Phenyl group and the Z group can be any available ring carbon atom or any available ring nitrogen atom.

17. A pharmaceutical composition for an individual or animal comprising a therapeutically effective amount of at least one compound of claim 1 in isolated and purified form or a physiologically acceptable salt thereof and further comprises at least one member selected from an excipient, a vehicle, an adjuvant, a flavoring, a colorant, or a preservative.

18. The pharmaceutical composition of claim 17 wherein the compound is selected from one of the following structures:

1-4
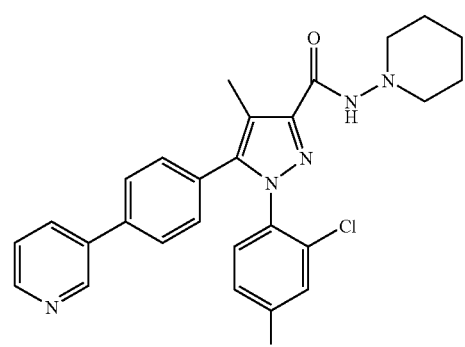

1-5
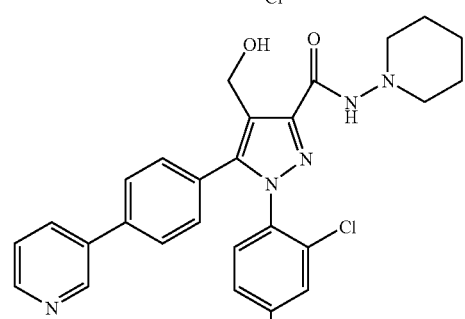

1-17
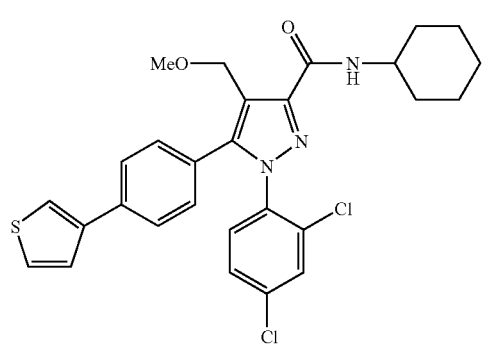

1-18
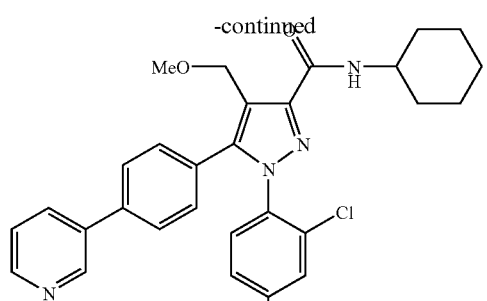

1-19
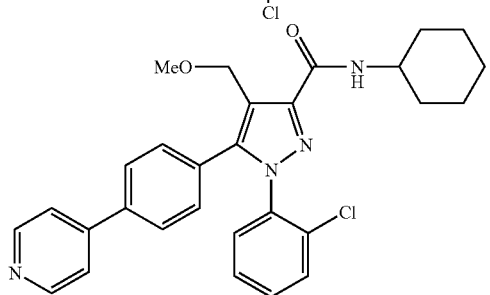

1-20
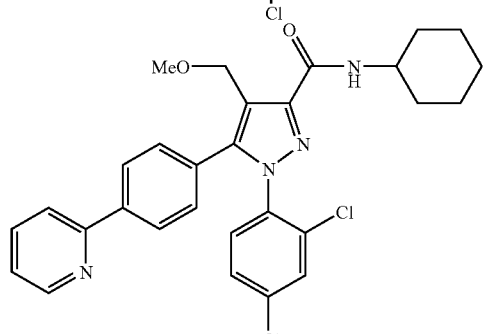

2-1
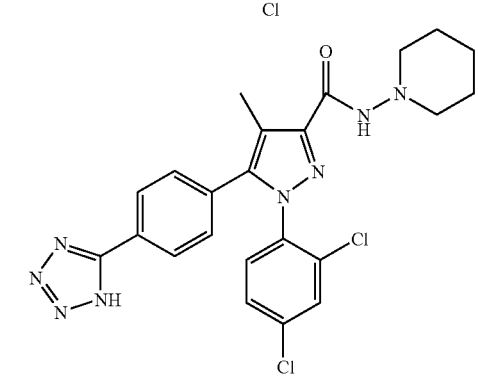

2-2
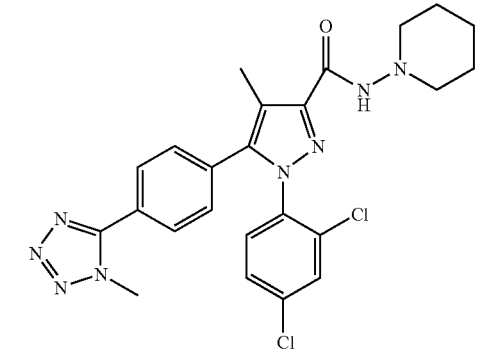

-continued
2-3
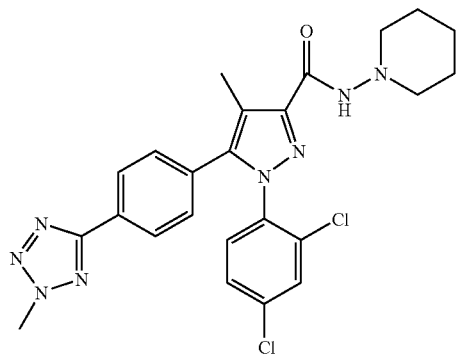
2-4
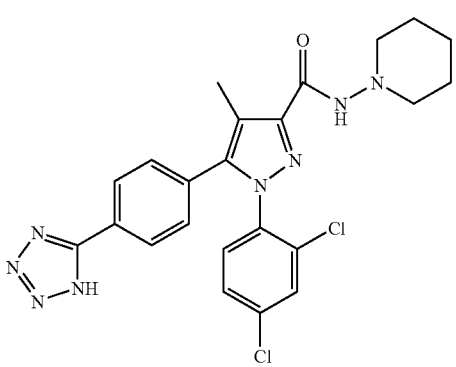
2-5
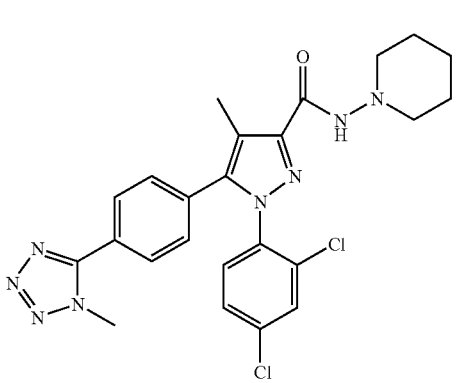
2-6
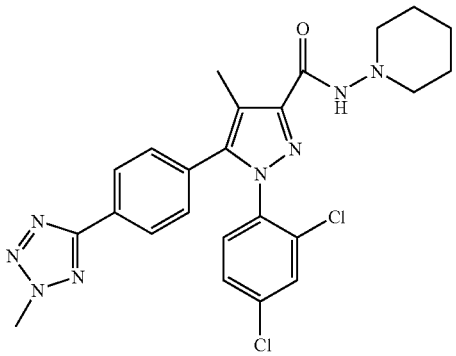
-continued
2-7
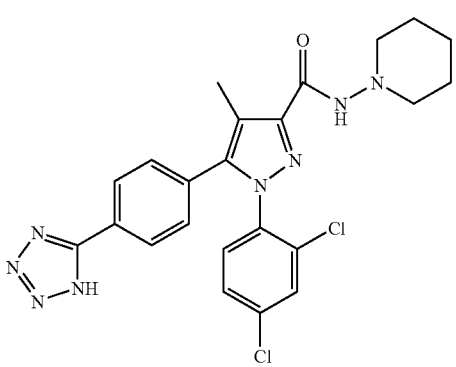
2-8
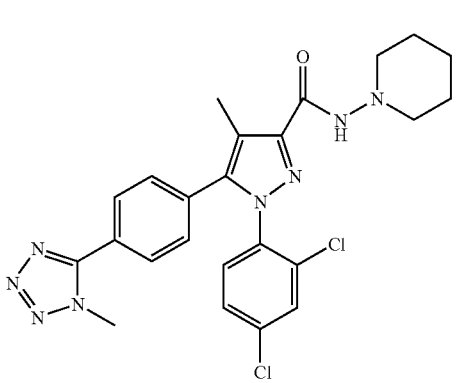
2-9
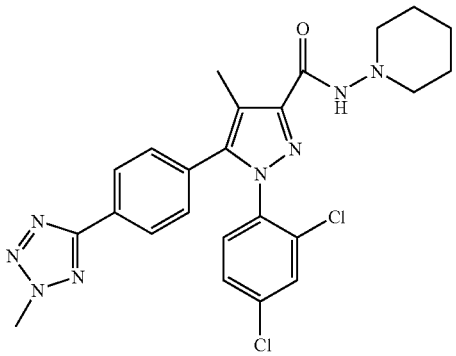
2-10
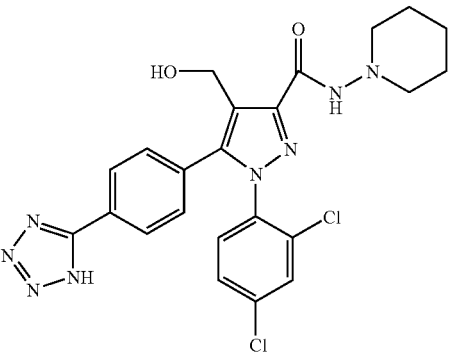

-continued
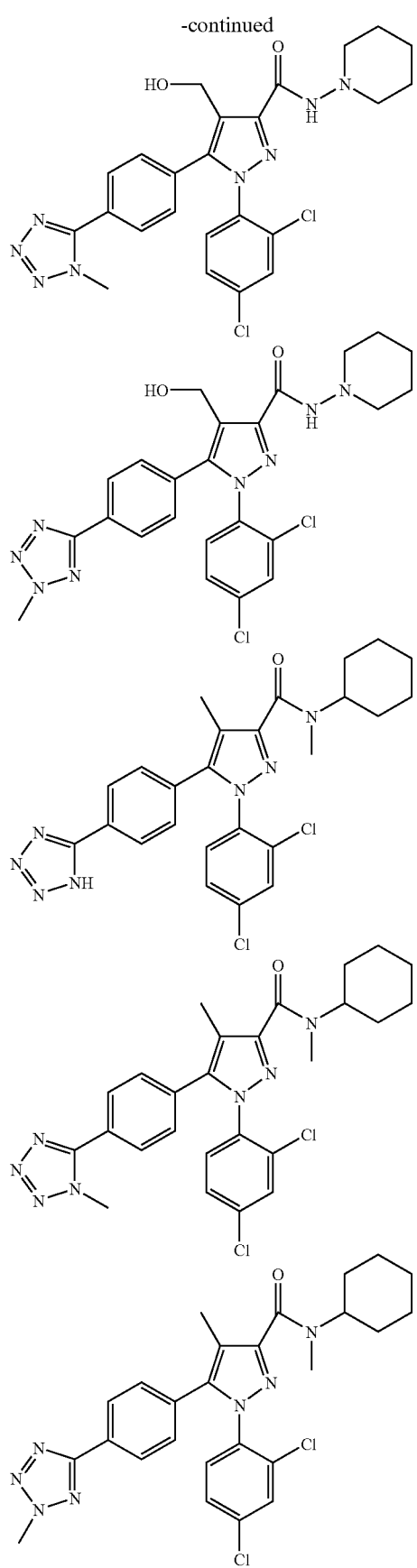
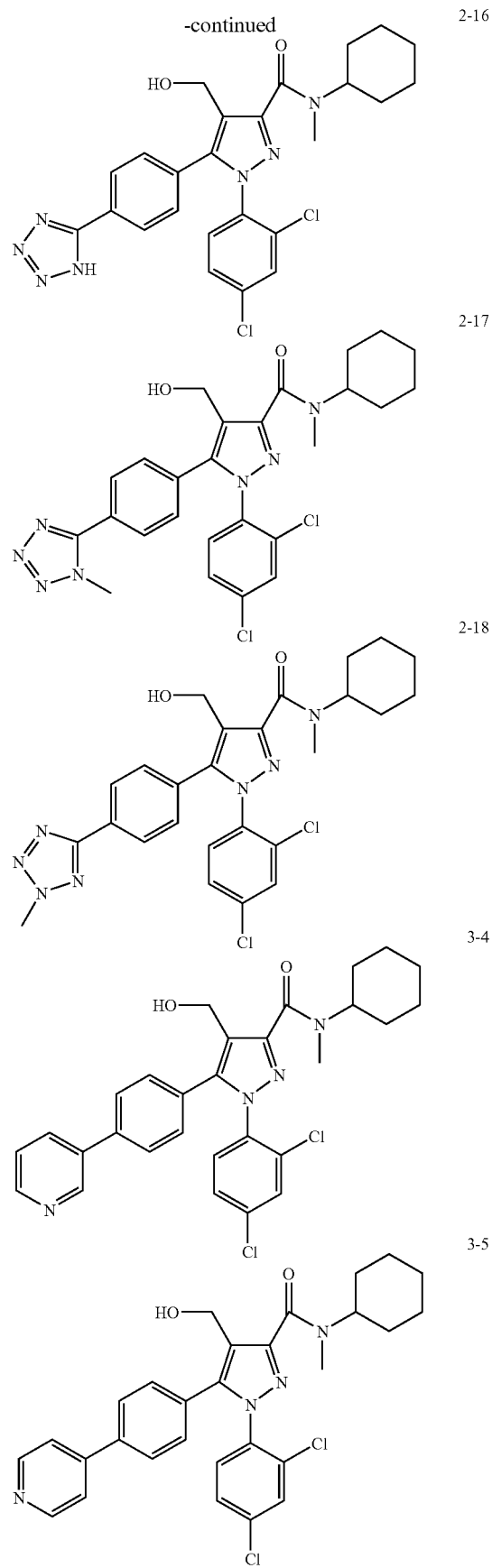

-continued
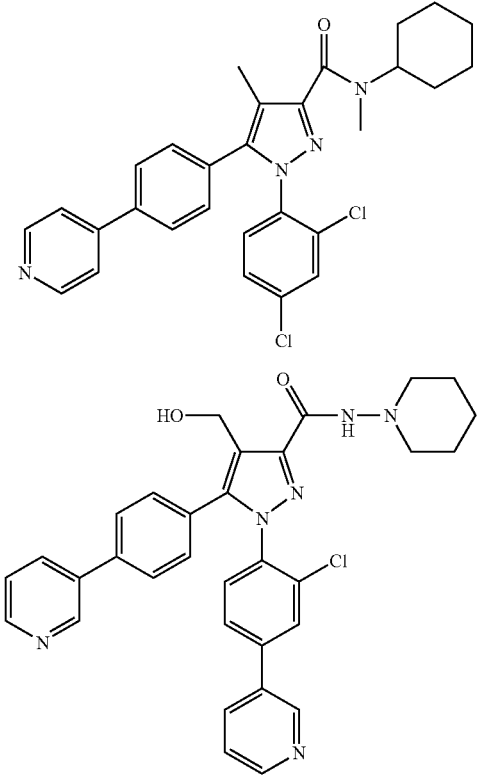
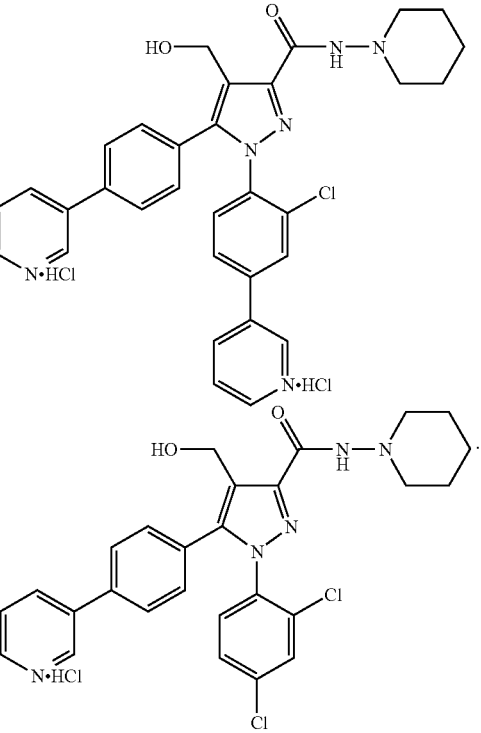
* * * * *

UNITED STATES PATENT AND TRADEMARK OFFICE
CERTIFICATE OF CORRECTION

| | | |
|---|---|---|
| PATENT NO. | : 7,393,842 B2 | |
| APPLICATION NO. | : 10/790498 | |
| DATED | : July 1, 2008 | |
| INVENTOR(S) | : Makriyannis et al. | |

It is certified that error appears in the above-identified patent and that said Letters Patent is hereby corrected as shown below:

Column 51:

Line 59, delete "ON," and substitute --CN,--.

Column 52:

Line 25, delete "OH" and substitute --CH--.

Line 37, delete "OH" and substitute --CH--.

Line 66, delete "$X_1$," and substitute --$X_1$--.

Column 54:

Line 27, delete "$x_4$" and substitute --$X_4$--.

Column 55:

Line 36, delete "*$coox_3$*," and substitute --$COOX_3$--.

Line 42, delete "$X_1$," and substitute --$X_1$--.

UNITED STATES PATENT AND TRADEMARK OFFICE
CERTIFICATE OF CORRECTION

PATENT NO. : 7,393,842 B2
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 72:

Lines 3 – 17, delete:

"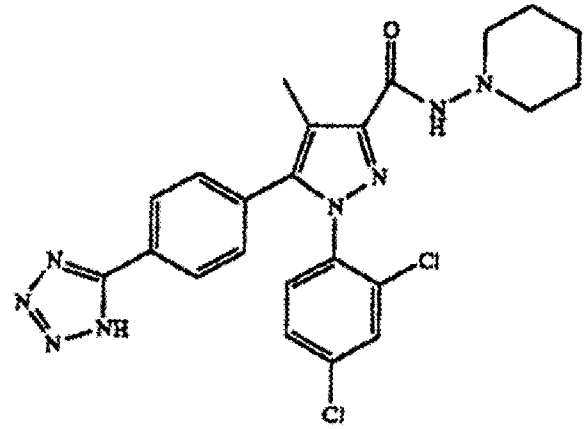"

and substitute:

--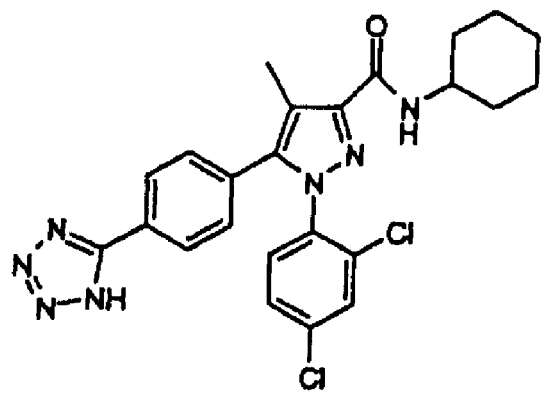--.

UNITED STATES PATENT AND TRADEMARK OFFICE
CERTIFICATE OF CORRECTION

PATENT NO. : 7,393,842 B2  Page 3 of 8
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 72:

Lines 20 – 34, delete:

" 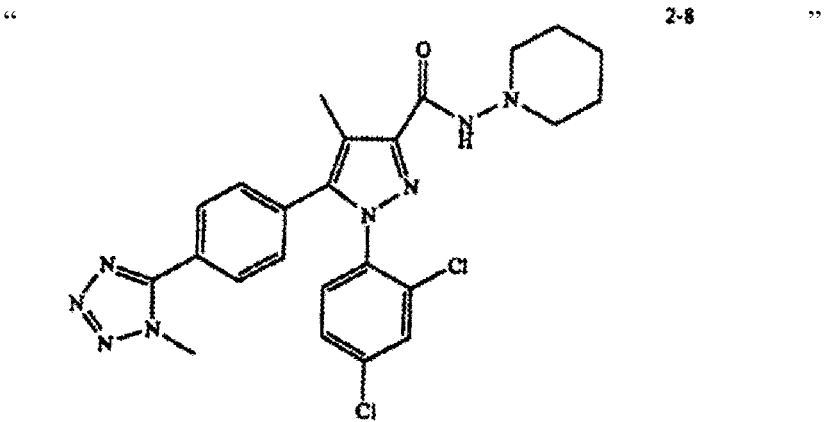 2-8 "

and substitute:

-- 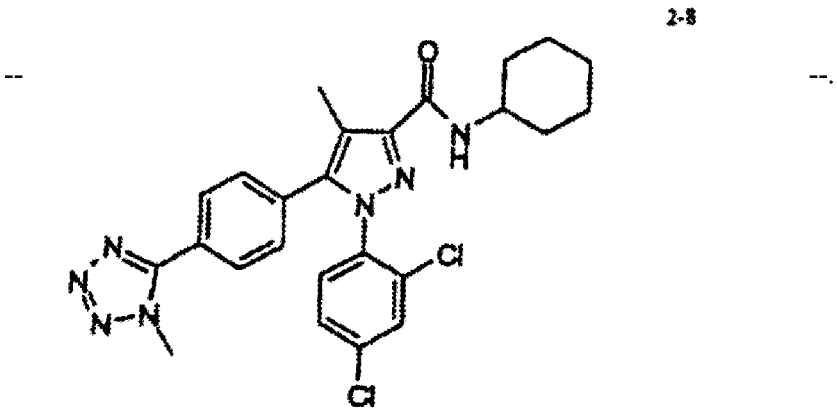 2-8 --.

UNITED STATES PATENT AND TRADEMARK OFFICE
CERTIFICATE OF CORRECTION

PATENT NO.       : 7,393,842 B2
APPLICATION NO.  : 10/790498
DATED            : July 1, 2008
INVENTOR(S)      : Makriyannis et al.

It is certified that error appears in the above-identified patent and that said Letters Patent is hereby corrected as shown below:

Column 72:

Lines 36 – 50, delete:

"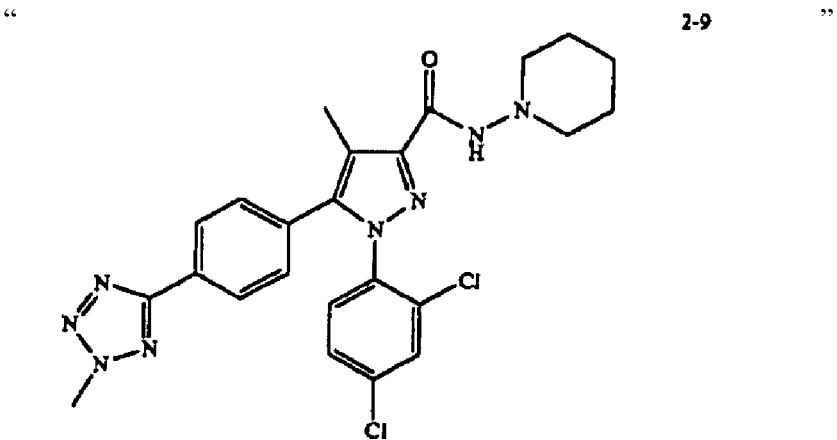 2-9 "

and substitute:

-- 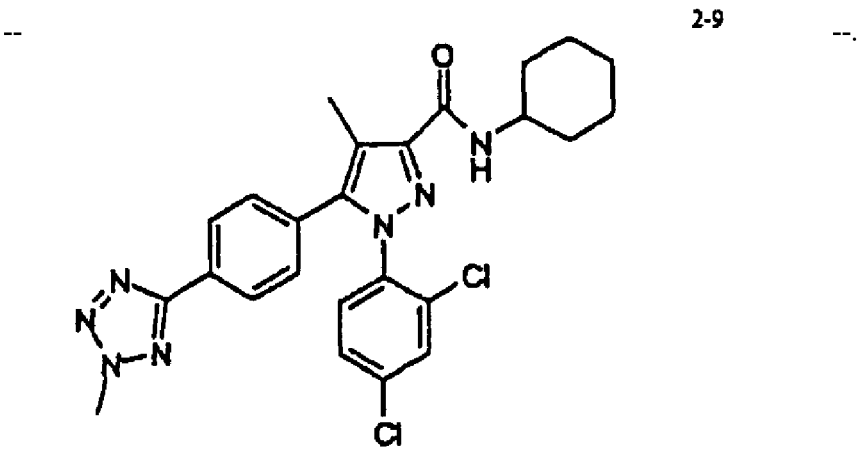 2-9 --.

UNITED STATES PATENT AND TRADEMARK OFFICE
CERTIFICATE OF CORRECTION

PATENT NO. : 7,393,842 B2  Page 5 of 8
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 72:

Lines 53 – 66, delete:

"  2-10  "

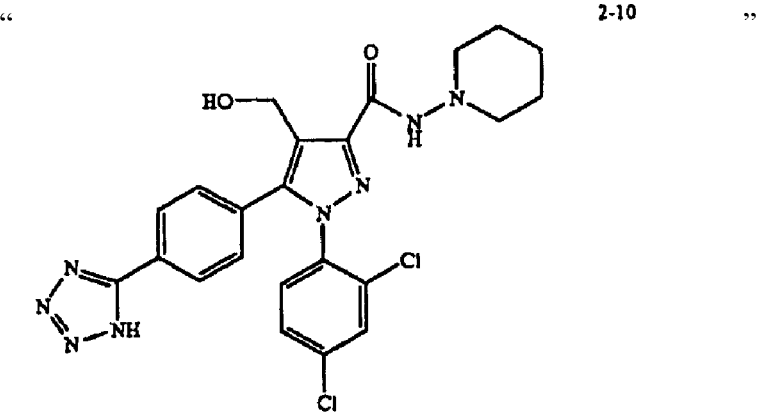

and substitute:

--  2-10  --.

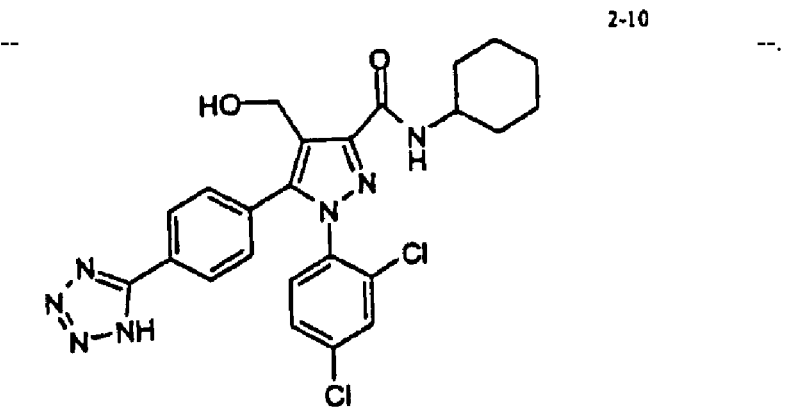

UNITED STATES PATENT AND TRADEMARK OFFICE
CERTIFICATE OF CORRECTION

PATENT NO. : 7,393,842 B2
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 73:

Lines 1 – 15, delete:

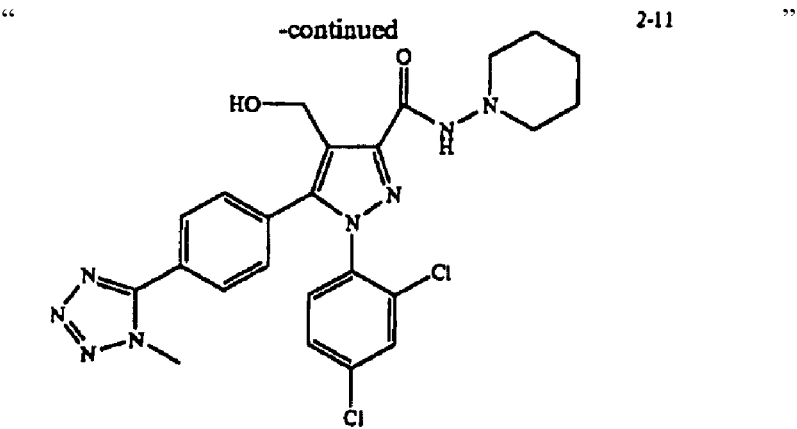

and substitute:

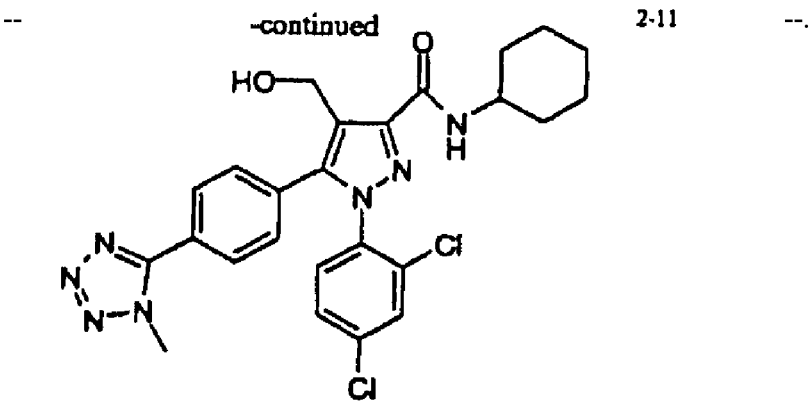

UNITED STATES PATENT AND TRADEMARK OFFICE
CERTIFICATE OF CORRECTION

PATENT NO.       : 7,393,842 B2
APPLICATION NO.  : 10/790498
DATED            : July 1, 2008
INVENTOR(S)      : Makriyannis et al.

It is certified that error appears in the above-identified patent and that said Letters Patent is hereby corrected as shown below:

Column 73:

Lines 14 – 28, delete:

"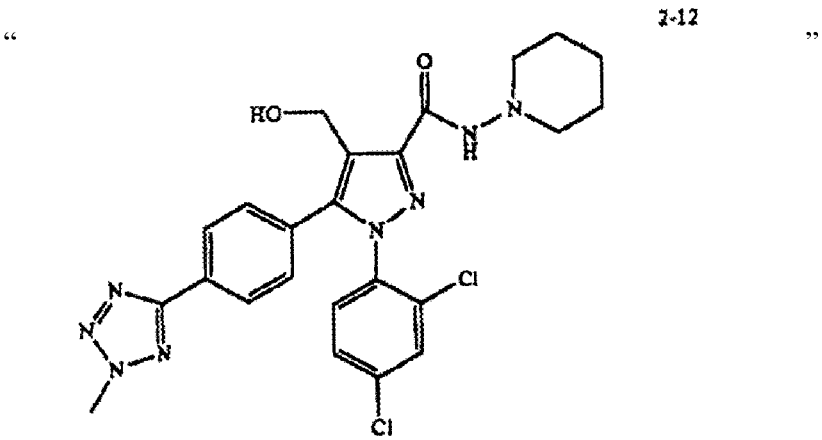"

UNITED STATES PATENT AND TRADEMARK OFFICE
CERTIFICATE OF CORRECTION

PATENT NO. : 7,393,842 B2
APPLICATION NO. : 10/790498
DATED : July 1, 2008
INVENTOR(S) : Makriyannis et al.

It is certified that error appears in the above-identified patent and that said Letters Patent is hereby corrected as shown below:

and substitute:

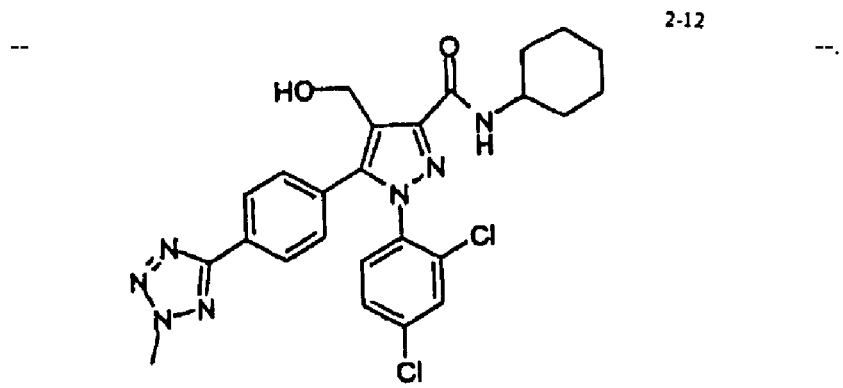

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,393,842 B2
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 51:

Line 59, delete "ON," and substitute --CN,--.

Column 52:

Line 25, delete "OH" and substitute --CH--.

Line 37, delete "OH" and substitute --CH--.

Line 66, delete "$X_1$," and substitute --$X_1$--.

Column 54:

Line 27, delete "$x_4$" and substitute --$X_4$--.

Column 55:

Line 36, delete "$coox_3$," and substitute --$COOX_3$--.

Line 42, delete "$X_1$," and substitute --$X_1$--.

UNITED STATES PATENT AND TRADEMARK OFFICE
CERTIFICATE OF CORRECTION

PATENT NO. : 7,393,842 B2  Page 2 of 6
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 72:

Lines 3 – 17, delete: " 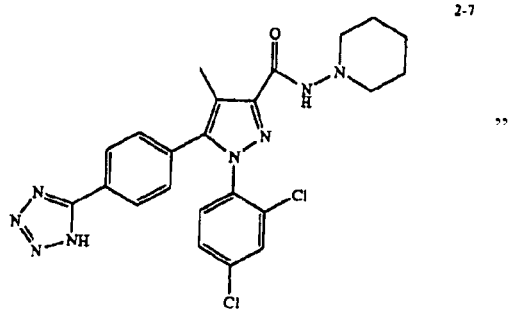 "

and substitute -- 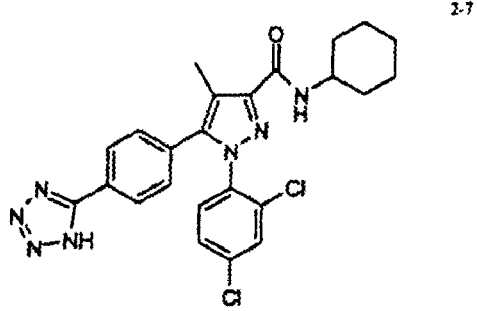 --

Column 72:

Lines 20 – 34, delete: " 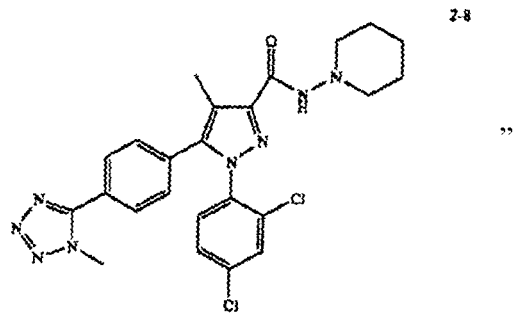 "

UNITED STATES PATENT AND TRADEMARK OFFICE
CERTIFICATE OF CORRECTION

PATENT NO. : 7,393,842 B2  Page 3 of 6
APPLICATION NO. : 10/790498
DATED : July 1, 2008
INVENTOR(S) : Makriyannis et al.

It is certified that error appears in the above-identified patent and that said Letters Patent is hereby corrected as shown below:

and substitute: -- 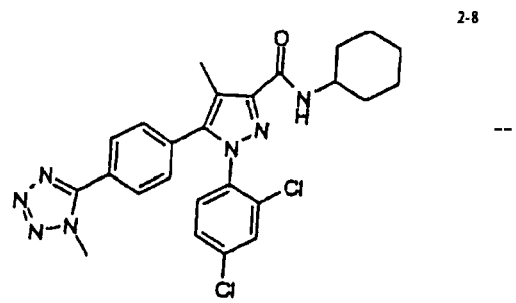 --

Column 72:

Lines 36 – 50, delete: " 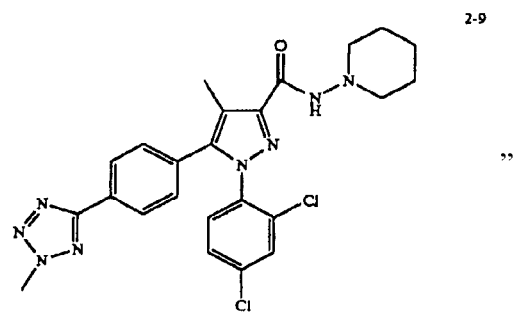 "

and substitute: -- 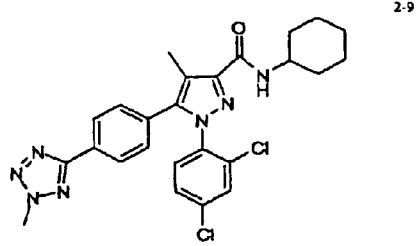 --

UNITED STATES PATENT AND TRADEMARK OFFICE
CERTIFICATE OF CORRECTION

PATENT NO. : 7,393,842 B2
APPLICATION NO. : 10/790498
DATED : July 1, 2008
INVENTOR(S) : Makriyannis et al.

It is certified that error appears in the above-identified patent and that said Letters Patent is hereby corrected as shown below:

Column 72:

Lines 53 – 66, delete: " 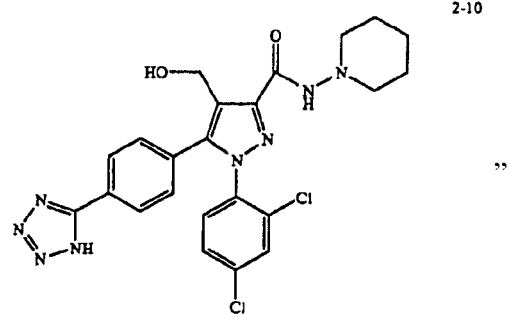 "

and substitute: -- 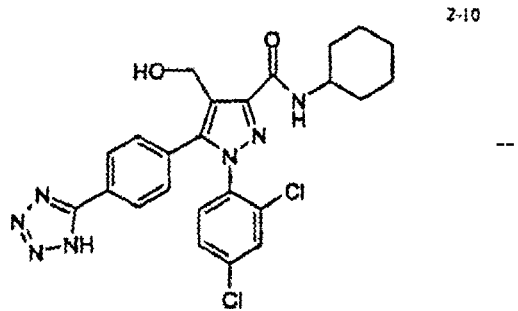 --

Column 73:

Lines 1 – 15, delete " 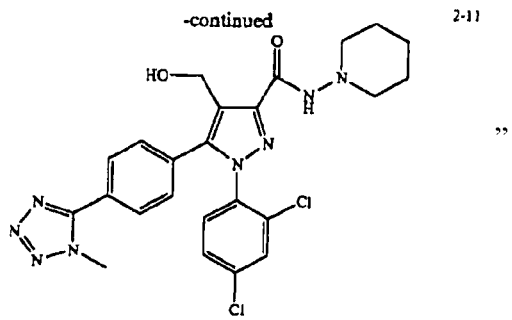 "

UNITED STATES PATENT AND TRADEMARK OFFICE
CERTIFICATE OF CORRECTION

PATENT NO. : 7,393,842 B2  Page 5 of 6
APPLICATION NO. : 10/790498
DATED : July 1, 2008
INVENTOR(S) : Makriyannis et al.

It is certified that error appears in the above-identified patent and that said Letters Patent is hereby corrected as shown below:

and substitute: -- 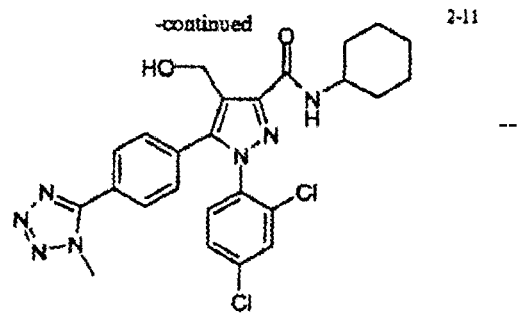 --

Column 73:

Lines 14 – 28, delete: " 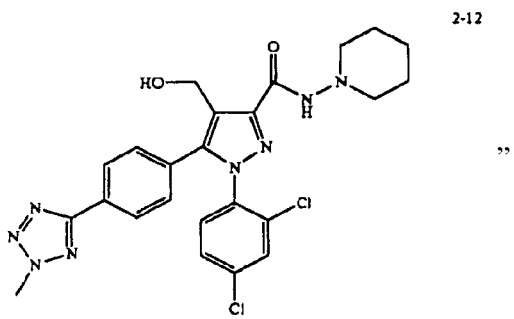 "

UNITED STATES PATENT AND TRADEMARK OFFICE
CERTIFICATE OF CORRECTION

PATENT NO.        : 7,393,842 B2
APPLICATION NO.   : 10/790498
DATED             : July 1, 2008
INVENTOR(S)       : Makriyannis et al.

It is certified that error appears in the above-identified patent and that said Letters Patent is hereby corrected as shown below:

and substitute: -- 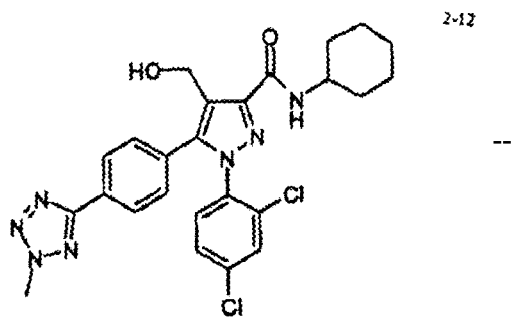 --

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,393,842 B2 | Page 1 of 1 |
| APPLICATION NO. | : 10/790498 | |
| DATED | : July 1, 2008 | |
| INVENTOR(S) | : Alexandros Makriyannis et al. | |

It is certified that error appears in the above-identified patent and that said Letters Patent is hereby corrected as shown below:

This certificate vacates the Certificate of Correction issued November 18, 2008. The certificate is a duplicate of the Certificate of Correction issued November 4, 2008. All requested changes were included in the Certificate of Correction issued November 4, 2008.

Signed and Sealed this

Ninth Day of December, 2008

JON W. DUDAS
*Director of the United States Patent and Trademark Office*